US009777060B2

(12) United States Patent
Hong et al.

(10) Patent No.: US 9,777,060 B2
(45) Date of Patent: Oct. 3, 2017

(54) ANTIBODY BINDING SPECIFICALLY TO HUMAN AND MOUSE L1CAM PROTEIN, AND USE THEREFOR

(71) Applicants: KANGWON NATIONAL UNIVERSITY University-Industry Cooperation Foundation, Chuncheon-si (KR); KOREA RESEARCH INSTITUTE OF BIOSCIENCE AND BIOTECHNOLOGY, Daejeon (KR)

(72) Inventors: Hyo Jeong Hong, Chuncheon-si (KR); In Soo Park, Goyang-si (KR); Seul Ki Cho, Busan (KR); Mun Sik Jeong, Chungcheongbuk-do (KR); Singh Rohit, Chuncheon-si (KR)

(73) Assignees: KANGWON NATIONAL UNIVERSITY University-Industry Cooperation Foundation, Chuncheon-si (KR); Korea Research Insititute of Bioscience and Biotechnology, Daejeon (KR)

( * ) Notice: Subject to any disclaimer, the term of this patent is extended or adjusted under 35 U.S.C. 154(b) by 219 days.

(21) Appl. No.: 14/714,647

(22) Filed: May 18, 2015

(65) Prior Publication Data
US 2015/0344571 A1  Dec. 3, 2015

Related U.S. Application Data

(63) Continuation-in-part of application No. PCT/KR2013/010474, filed on Nov. 18, 2013.

(30) Foreign Application Priority Data

Nov. 16, 2012  (KR) ........................ 10-2012-0130590

(51) Int. Cl.

| | | |
|---|---|---|
| A61K 39/395 | (2006.01) | |
| A61K 39/44 | (2006.01) | |
| G01N 33/53 | (2006.01) | |
| C07K 16/00 | (2006.01) | |
| C07K 16/46 | (2006.01) | |
| C07K 16/28 | (2006.01) | |
| C07H 21/04 | (2006.01) | |
| C12P 21/06 | (2006.01) | |
| C12N 15/87 | (2006.01) | |
| C12N 1/20 | (2006.01) | |
| C12N 15/74 | (2006.01) | |
| A61K 47/48 | (2006.01) | |
| G01N 33/574 | (2006.01) | |
| A61K 39/00 | (2006.01) | |

(52) U.S. Cl.
CPC .... *C07K 16/2803* (2013.01); *A61K 47/48569* (2013.01); *G01N 33/57492* (2013.01); *A61K 2039/505* (2013.01); *C07K 2317/56* (2013.01); *C07K 2317/565* (2013.01); *C07K 2317/567* (2013.01); *C07K 2317/92* (2013.01); *G01N 2333/70503* (2013.01); *G01N 2333/70596* (2013.01)

(58) Field of Classification Search
None
See application file for complete search history.

(56) References Cited

U.S. PATENT DOCUMENTS

| | | |
|---|---|---|
| 8,138,313 B2 | 3/2012 | Kelm et al. |
| 8,153,122 B2 | 4/2012 | Hong et al. |
| 2004/0115206 A1 | 6/2004 | Primiano et al. |

FOREIGN PATENT DOCUMENTS

| | | |
|---|---|---|
| KR | 10-0756051 B1 | 9/2007 |
| KR | 10-2009-0034242 A | 4/2009 |
| KR | 10-0931976 B1 | 12/2009 |
| KR | 10-2010-0064985 A | 6/2010 |
| WO | 2009/045075 A2 | 4/2009 |

OTHER PUBLICATIONS

Park et al. Isolation and characterization of human antibodies that recognize both hL1cam and mL1cam. Abstract A-79, 2nd Korea Research Institute of Bioscience and Biotechnology (KRIBB) Post Festival, Nov. 12, 2008. p. 11.*
Barbas et al. (1991) "Combinatorial immunoglobulin libraries on the surface of phage (Phabs): Rapid selection of antigen-specific fabs," Methods: A Companion to Methods in Enzymology. 2:119-124.
Bateman et al. (1996) "Outline structure of the human L1 cell adhesion molecule and the sites where mutations cause neurological disorders," EMBO J. 15:6050-6059.
Huszar et al. (2006) "Expression profile analysis in multiple human tumors identifies L1 (CD171) as a molecular marker for differential diagnosis and targeted therapy," Human Pathology. 37:1000-1008.

(Continued)

*Primary Examiner* — Maher Haddad
(74) *Attorney, Agent, or Firm* — Lathrop Gage LLP; Andrew T. Wilkins; Brian C. Trinque

(57) ABSTRACT

The present invention relates to a novel antibody specifically binding to human and mouse L1CAM, and more particularly, to an antibody binding to both human and mouse L1CAM with high affinity, which is prepared by modifying a sequence of an L1 cell adhesion molecule (L1CAM)-specific antibody comprising a heavy-chain variable region of SEQ ID NO. 1 and a light-chain variable region of SEQ ID NO. 5, a polynucleotide encoding the antibody, an expression vector comprising the polynucleotide, a transformant introduced with the vector, a pharmaceutical composition for preventing or treating cancer comprising the antibody, a method for treating cancer using the antibody, a composition for diagnosing cancer comprising the antibody, a kit for diagnosing cancer comprising the composition, a method for providing information for cancer diagnosis using the antibody, and an antibody-drug conjugate prepared by conjugating a drug to the antibody.

20 Claims, 23 Drawing Sheets

(56) References Cited

OTHER PUBLICATIONS

Knogler et al. (2006) "Evaluation of 177Lu-DOTA-labeled aglycosylated monoclonal anti-L1-CAM antibody chCE7: influence of the number of chelators on the in vitro and in vivo properties," Nucl. Med. Biol. 33(7):883-889.

Lee et al. (1997) "Specific Neural and Adrenal Medullary Antigens Detected by Antisera to Clonal PC12 Phenochromocytoma Cells," Proc. Natl. Acad. Sci. USA. 74:5021-5025.

Lee et al. (2012) "A chimeric antibody to L1 cell adhesion molecule shows therapeutic effect in an intrahepatic cholangiocarcinoma model," Exp. Mol. Med. 4:293-302.

Min et al. (2010) "L1 Cell Adhesion Molecule Is a Novel Therapeutic Target in Intrahepatic Cholangiocarcinoma ," Clin. Cancer Res. 16:3571-3580.

Raveh et al. (2009) "L1 cell adhesion molecule (L1CAM) in invasive tumors," Cancer Letters. 282:137-145.

Winter et al. (1994) "Making antibodies by phage display technology," Ann. Rev. Immunol. 12:433-455.

Zwick et al. (2001) "Identification and Characterization of a Peptide That Specifically Binds the Human, Broadly Neutralizing Anti-Human Immunodeficiency Virus Type 1 Antibody b12," Journal of Virology. 75(14):6692-6699.

International Search Report with Written Opinion corresponding to International Patent Application No. PCT/KR2013/010474, mailed Feb. 25, 2014.

* cited by examiner

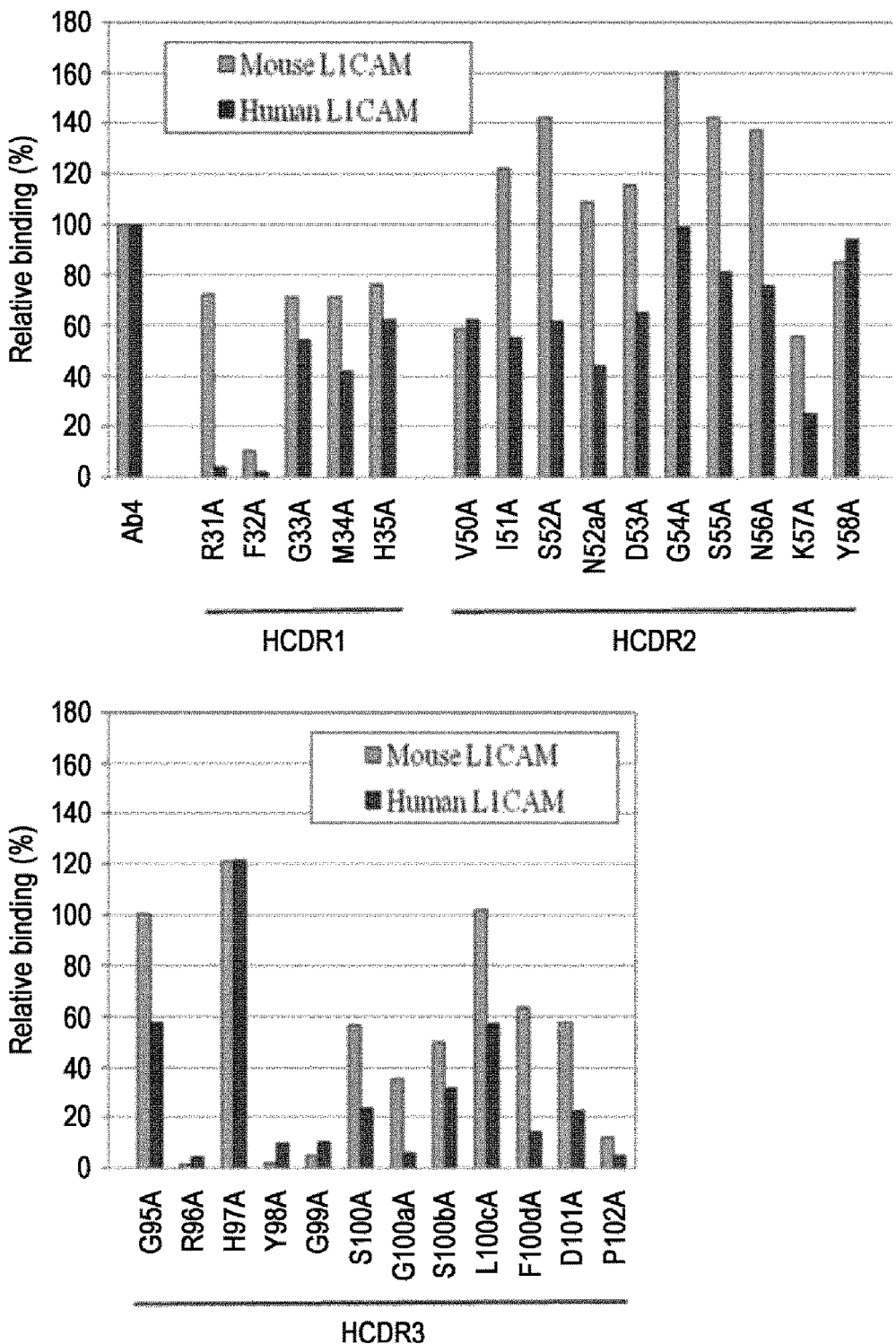
[FIG. 1a]

[FIG. 1b]
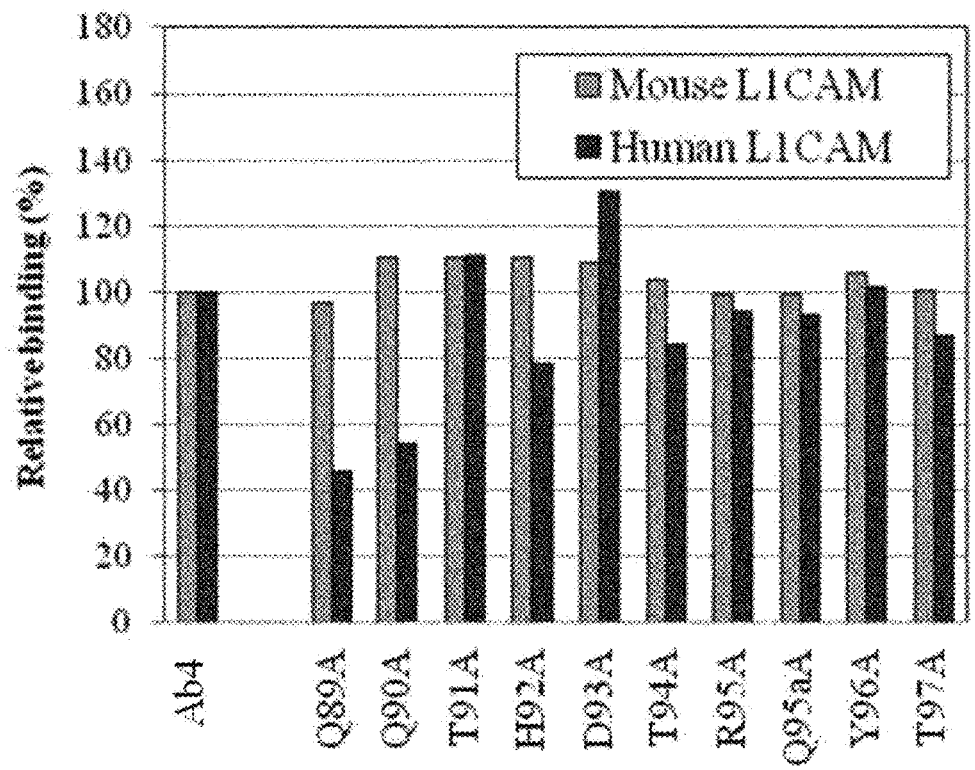
[FIG. 1c]
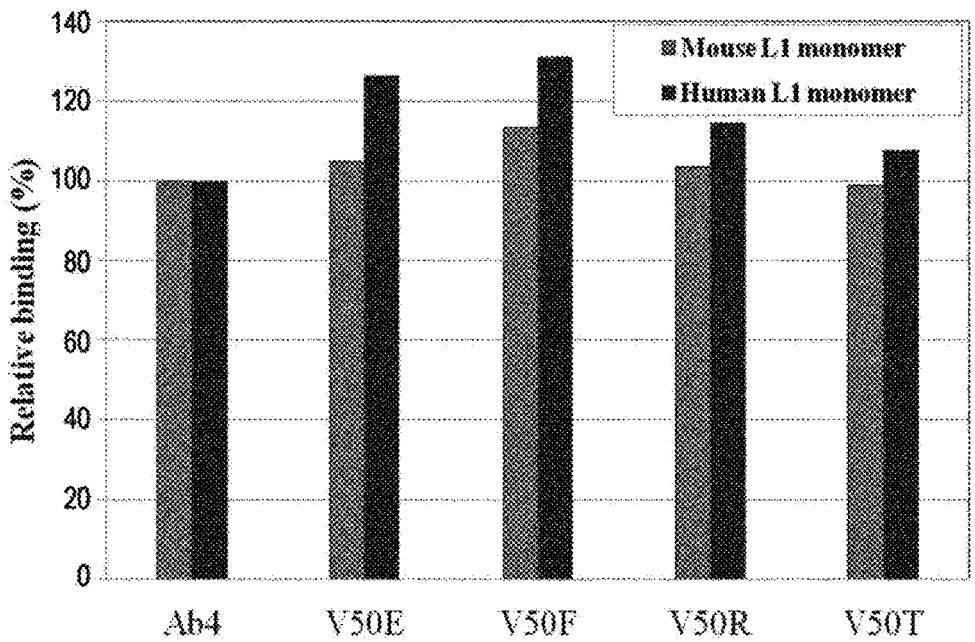

[FIG. 2a]
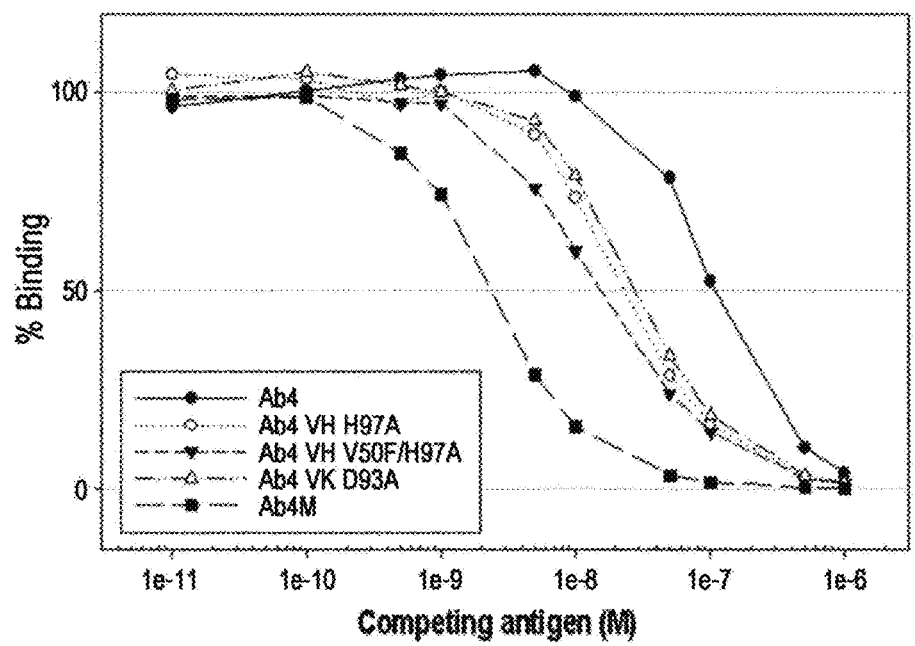
[FIG. 2b]
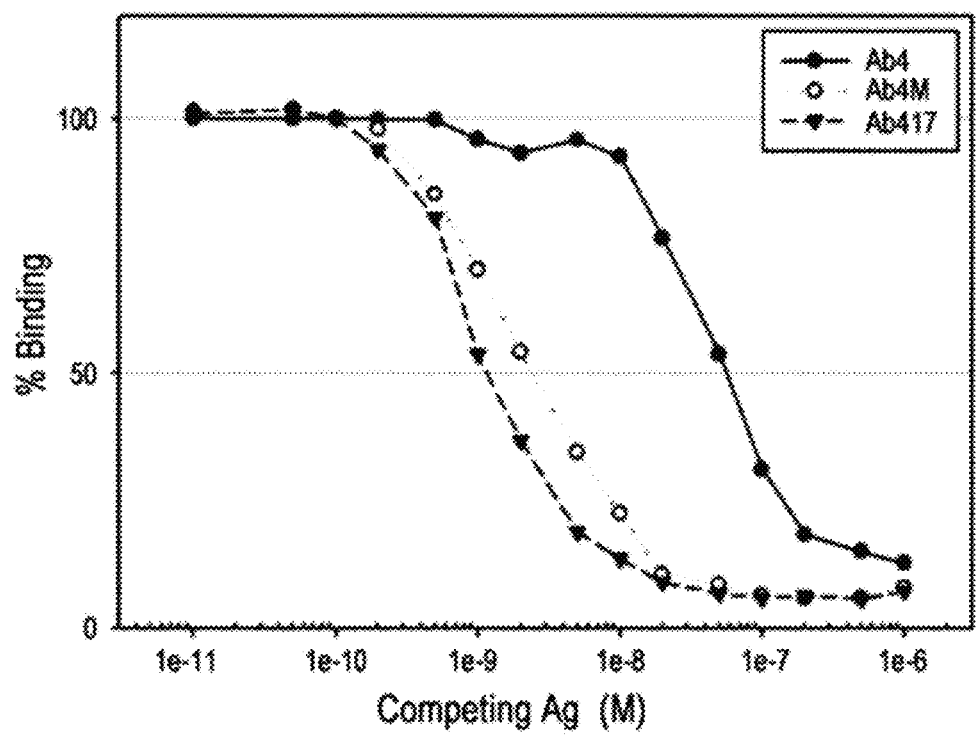

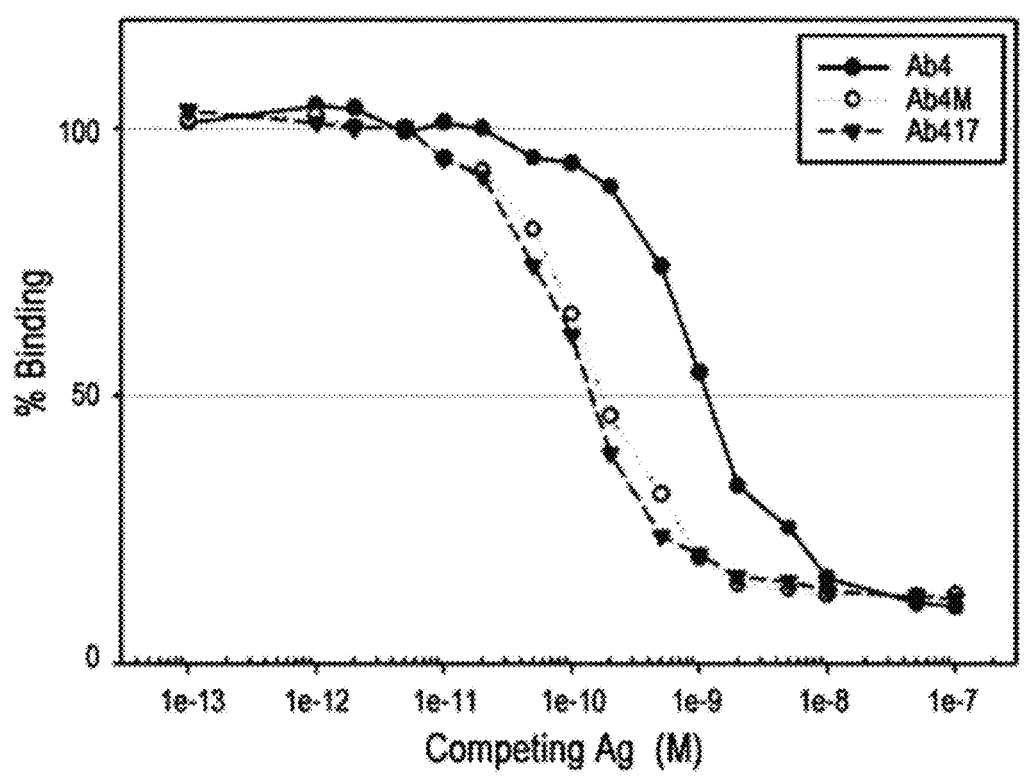
[FIG. 2c]

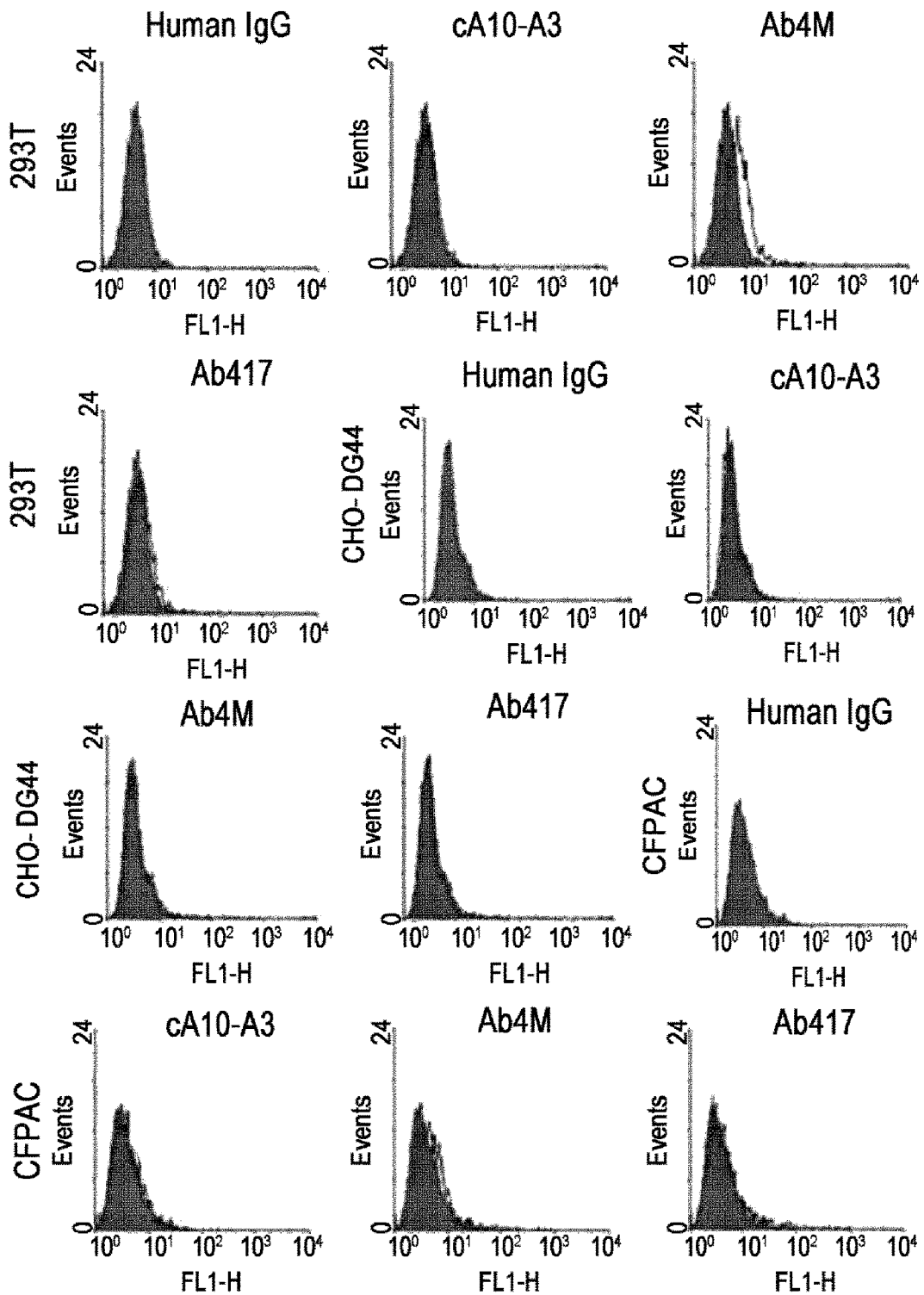
[FIG. 3a]

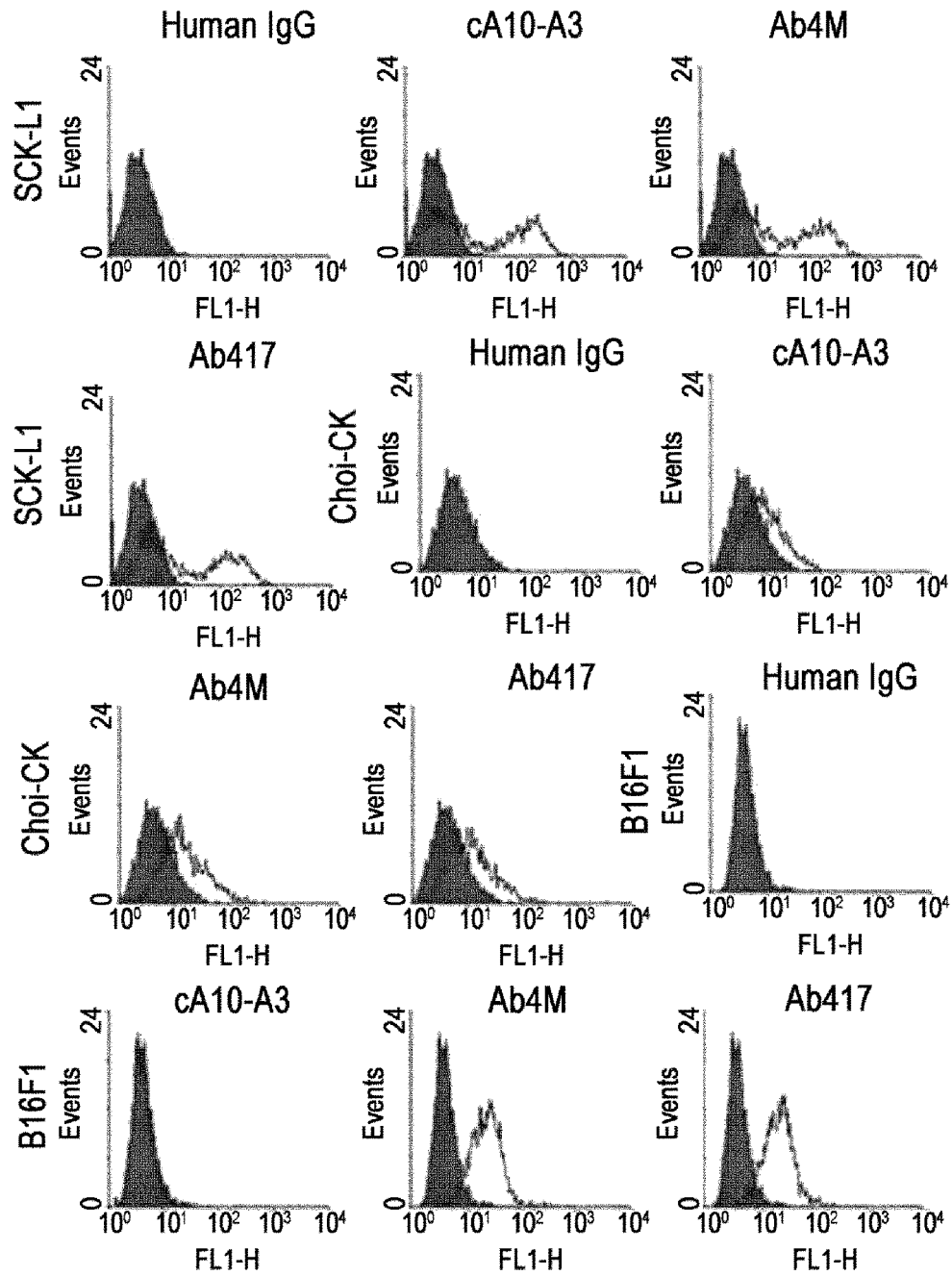
[FIG. 3b]

[FIG. 4a]
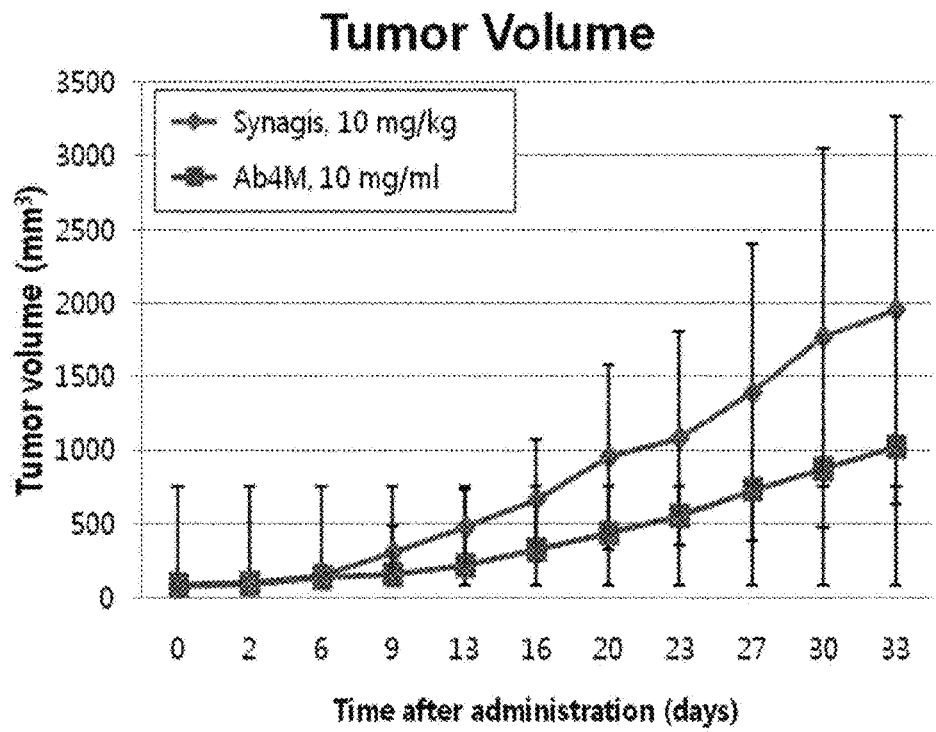
[FIG. 4b]
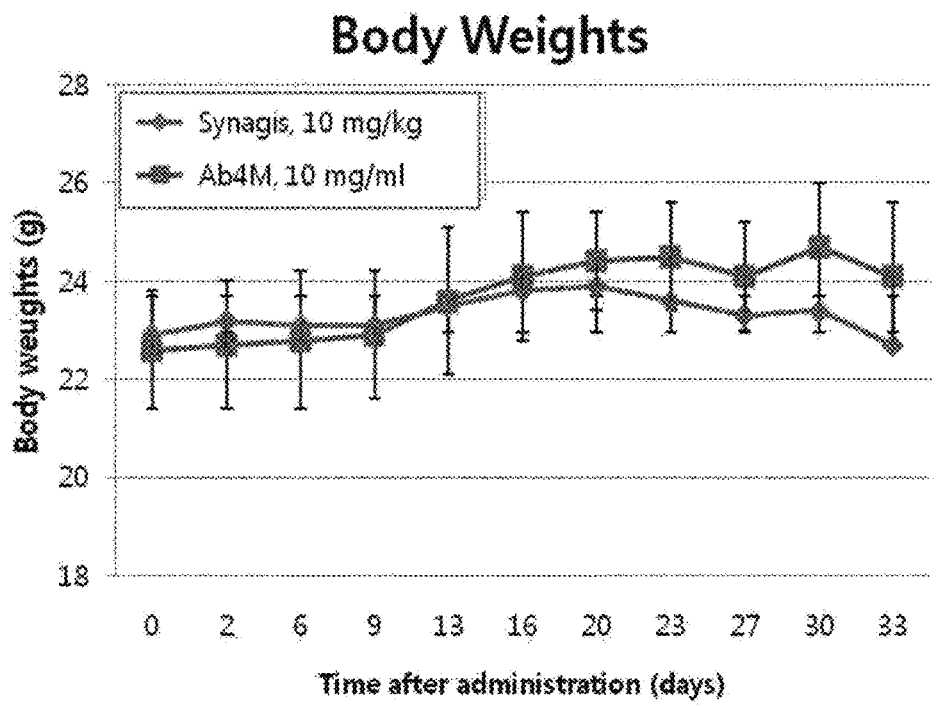

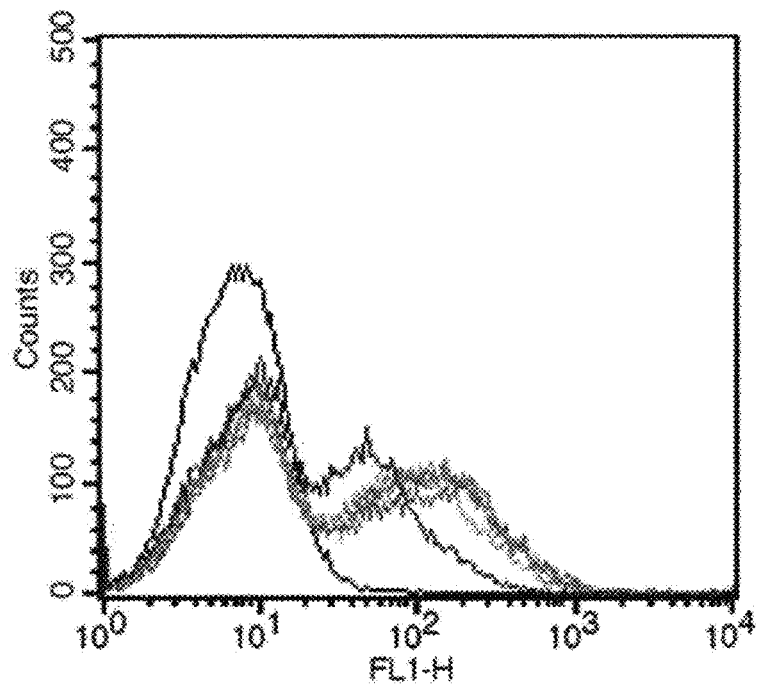
[FIG. 5a]
| Key | Name | Parameter | Gate | Concentration of hL1(Ig5)-Fc |
|---|---|---|---|---|
| — | 101006.013 | FL1-H | G1 | (control) |
| — | 101006.014 | FL1-H | G1 | $1 \times 10^{-5}$ M |
| — | 101006.015 | FL1-H | G1 | $5 \times 10^{-6}$ M |
| — | 101006.016 | FL1-H | G1 | $1 \times 10^{-6}$ M |
| — | 101006.017 | FL1-H | G1 | $5 \times 10^{-7}$ M |
| — | 101006.018 | FL1-H | G1 | $1 \times 10^{-7}$ M |
| — | 101006.019 | FL1-H | G1 | $1 \times 10^{-8}$ M |

[FIG. 5b]
1) Ab4M-18
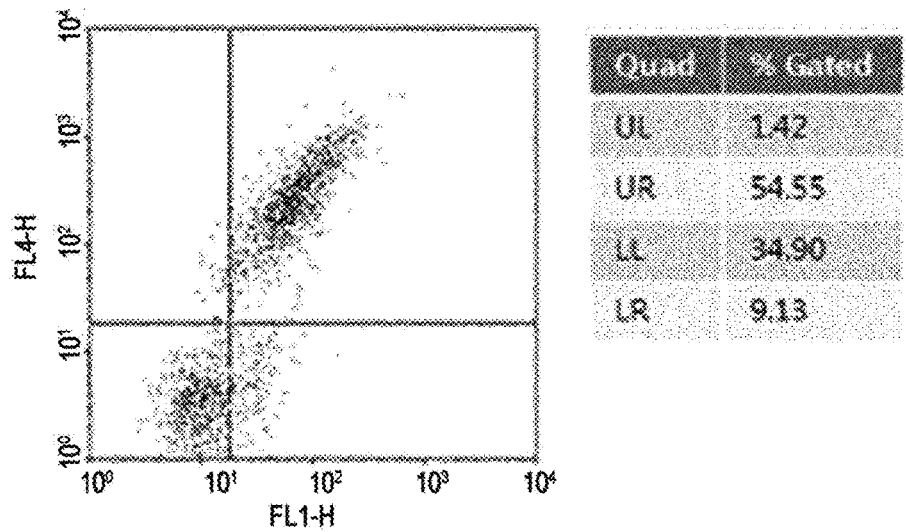
2) Ab4M
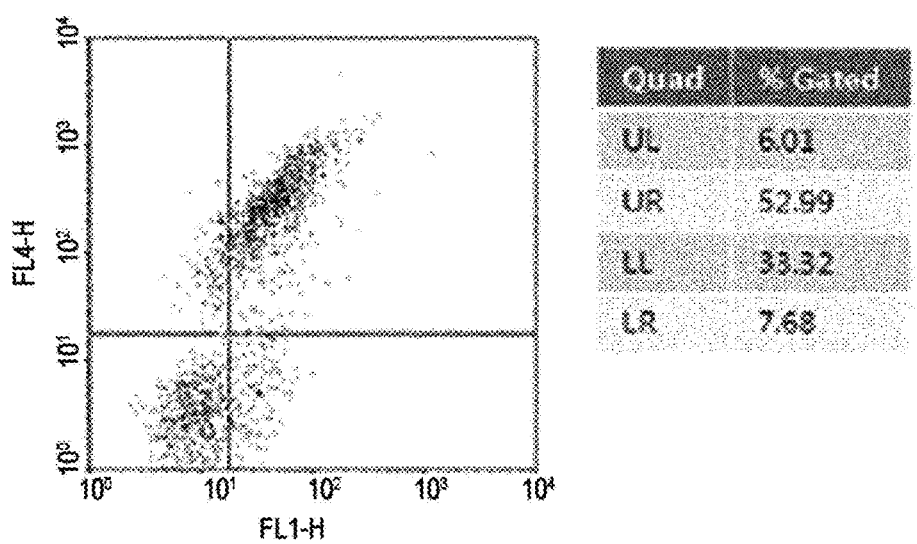

[FIG. 6a]
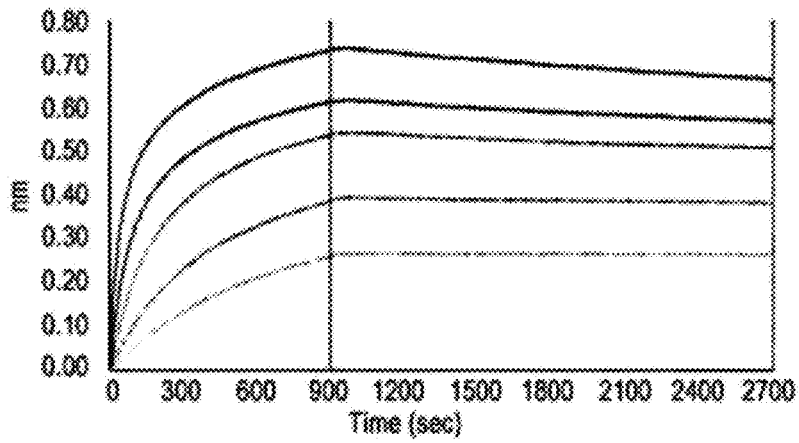
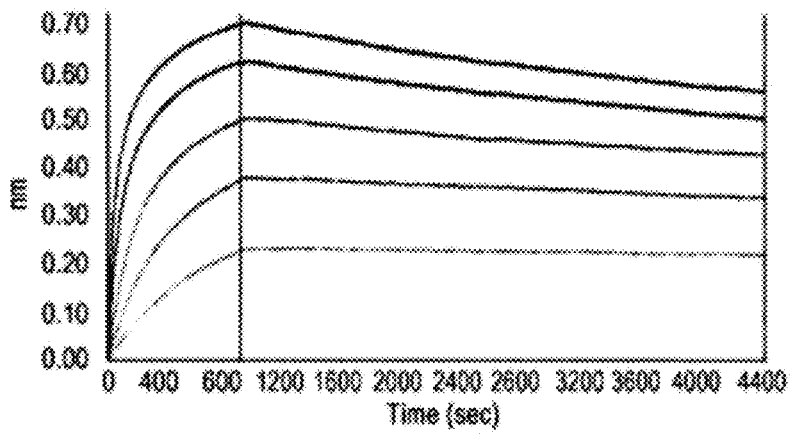
C Affinities of Ab417 and Ab4M antibodies for human L1CAM
| | $K_D$ (nM) | $K_{on}$ (1/Ms) | $K_{dis}$ (1/S) | Full $R^2$ |
|---|---|---|---|---|
| Ab4M | 0.33 | 1.30E+05 | 4.30E-05 | 0.99 |
| Ab417 | 0.18 | 1.27E+05 | 2.3E-05 | 0.99 |

[FIG. 6b]
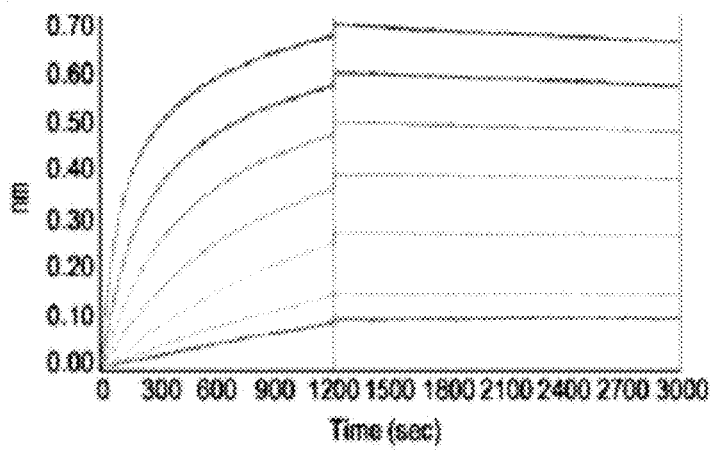
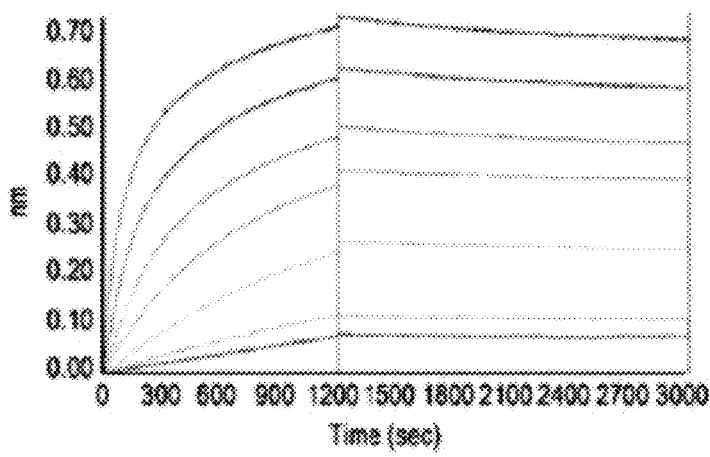
C  Affinities of Ab417 and Ab4M antibodies for mouse L1CAM
| | $K_D$ (pM) | $K_{on}$ (1/Ms) | $K_{off}$ (1/S) | Full $R^2$ |
|---|---|---|---|---|
| Ab4M | 89.3 | 2.49E+05 | 2.22E-05 | 0.99 |
| Ab417 | 34.8 | 2.33E+05 | 8.10E-06 | 0.99 |

[FIG. 7a]
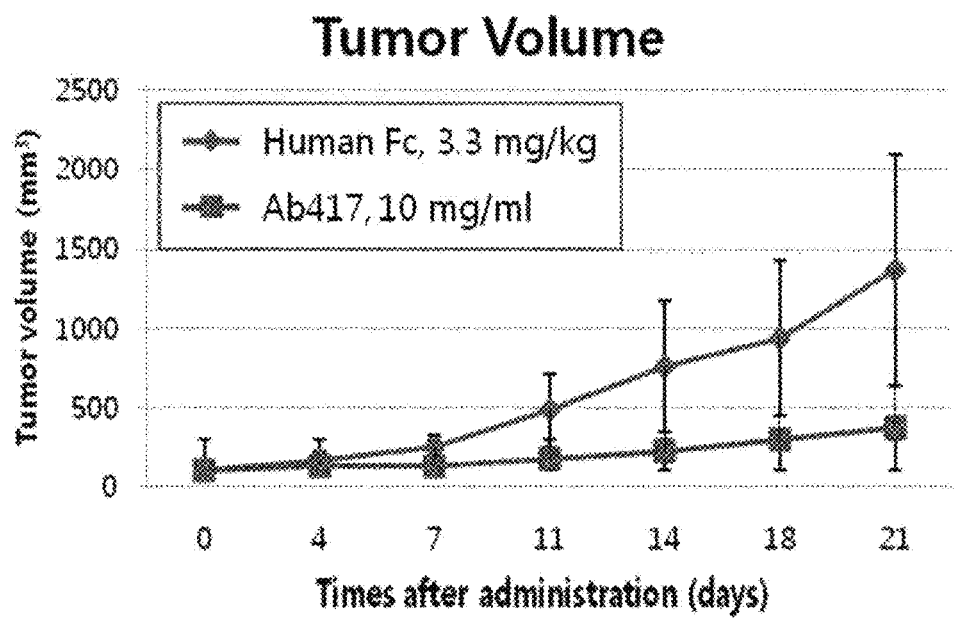

[FIG. 7b]
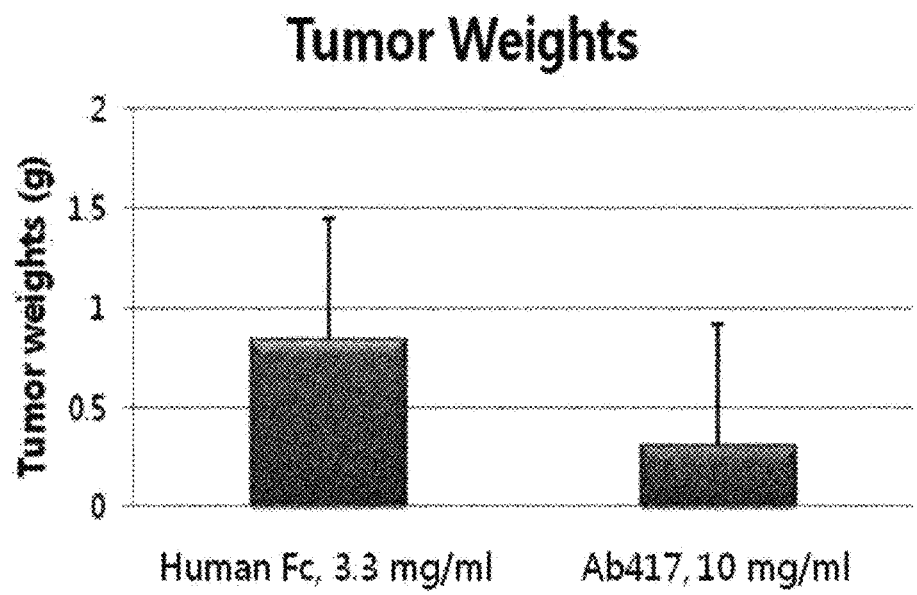
[FIG. 7c]
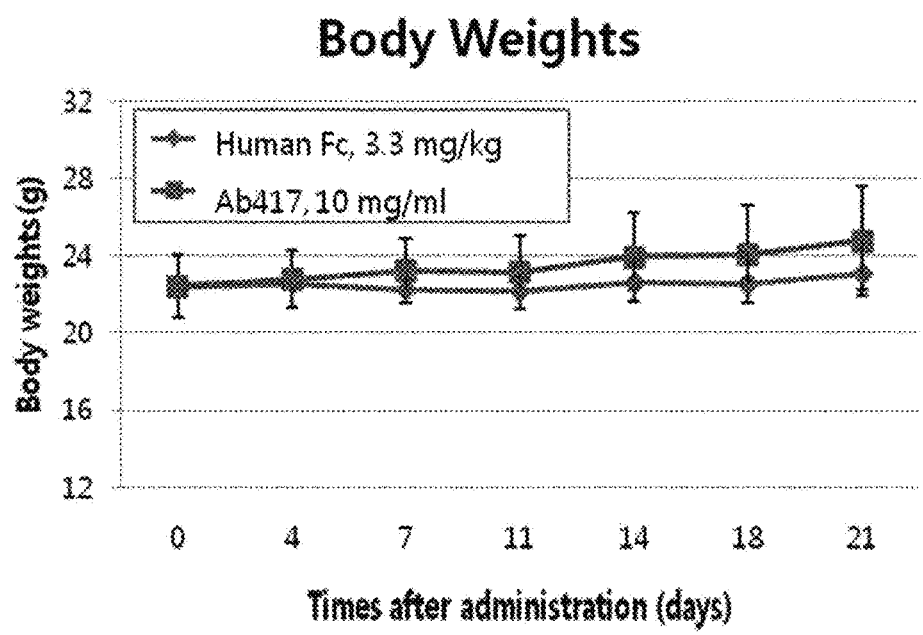

|  1 |  2 |  3 |  4 |  5 |  6 |  7 |  8 |  9 | 10 | 11 | 12 | 13 | 14 | 15 | 16 | 17 | 18 | 19 | 20 |
|---|---|---|---|---|---|---|---|---|---|---|---|---|---|---|---|---|---|---|---|
| E | V | Q | L | V | E | S | G | G | G | V | V | Q | P | G | R | S | L | R | L |
| GAA | GTG | CAG | CTG | GTG | GAA | AGC | GGC | GGC | GGC | GTG | GTG | CAG | CCG | GGC | CGC | AGC | CTG | CGC | CTG |

| 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|
| S | C | A | A | S | G | F | T | F | S | R | F | G | M | H | W | V | R | Q | A |
| AGC | TGC | GCG | GCG | AGC | GGC | TTT | ACC | TTT | AGC | CGC | TTT | GGC | ATG | CAT | TGG | GTG | CGC | CAG | GCG |

| 41 | 42 | 43 | 44 | 45 | 46 | 47 | 48 | 49 | 50 | 51 | 52 | 52a | 53 | 54 | 55 | 56 | 57 | 58 | 59 |
|---|---|---|---|---|---|---|---|---|---|---|---|---|---|---|---|---|---|---|---|
| P | G | K | G | L | E | W | V | A | F | I | S | N | D | G | S | N | K | Y | Y |
| CCG | GGC | AAA | GGC | CTG | GAA | TGG | GTG | GCG | TTT | ATT | AGC | AAC | GAT | GGC | AGC | AAC | AAA | TAT | TAT |

| 60 | 61 | 62 | 63 | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|---|---|
| A | D | S | V | K | G | R | F | T | I | S | R | D | N | S | K | N | T | L | Y |
| GCG | GAT | AGC | GTG | AAA | GGC | CGC | TTT | ACC | ATT | AGC | CGC | GAT | AAC | AGC | AAA | AAC | ACC | CTG | TAT |

| 80 | 81 | 82 | 82a | 82b | 82c | 83 | 84 | 85 | 86 | 87 | 88 | 89 | 90 | 91 | 92 | 93 | 94 | 95 | 96 |
|---|---|---|---|---|---|---|---|---|---|---|---|---|---|---|---|---|---|---|---|
| L | Q | M | N | S | L | R | P | E | D | T | A | V | Y | Y | C | A | R | G | R |
| CTG | CAG | ATG | AAC | AGC | CTG | CGC | CCG | GAA | GAT | ACC | GCG | GTG | TAT | TAT | TGC | GCG | CGC | GGC | CGC |

| 97 | 98 | 99 | 100 | 100a | 100b | 100c | 100d | 101 | 102 | 103 | 104 | 105 | 106 | 107 | 108 | 109 | 110 | 111 | 112 |
|---|---|---|---|---|---|---|---|---|---|---|---|---|---|---|---|---|---|---|---|
| A | Y | G | S | G | S | L | F | D | P | W | G | Q | G | T | L | V | T | V | S |
| GCG | TAT | GGC | AGC | GGC | AGC | CTG | TTT | GAT | CCG | TGG | GGC | CAG | GGC | ACC | CTG | GTG | ACC | GTG | AGC |

S
AGC

```
  1   2   3   4   5   6   7   8   9  10  11  12  13  14  15  16  17  18  19  20
  D   I   Q   L   T   Q   S   P   S   S   L   S   A   S   V   G   D   R   V   T
 GAT ATT CAG CTG ACC CAG AGC CCG AGC AGC CTG AGC GCG AGC GTG GGC GAT CGC GTG ACC 21  22  23  24  25  26  27  28  29  30  31  32  33  34  35  36  37  38  39  40
  I   T   C   R   A   S   R   T   I   S   I   Y   V   N   W   Y   R   Q   R   P
 ATT ACC TGC CGC GCG AGC CGC ACC ATT AGC ATT TAT GTG AAC TGG TAT CGC CAG CGC CCG 41  42  43  44  45  46  47  48  49  50  51  52  53  54  55  56  57  58  59  60
  G   K   A   P   E   S   L   I   Y   A   A   S   N   L   H   S   G   V   P   S
 GGC AAA GCG CCG GAA AGC CTG ATT TAT GCG GCG AGC AAC CTG CAT AGC GGC GTG CCG AGC 61  62  63  64  65  66  67  68  69  70  71  72  73  74  75  76  77  78  79  80
  R   F   S   G   S   G   S   G   T   D   F   T   L   T   I   S   S   L   Q   P
 CGC TTT AGC GGC AGC GGC AGC GGC ACC GAT TTT ACC CTG ACC ATT AGC AGC CTG CAG CCG 81  82  83  84  85  86  87  88  89  90  91  92  93  94  95  95a 96  97  98  99
  E   D   F   A   T   Y   Y   C   Q   Q   S   I   G   R   G   V   V   T   F   G
 GAA GAT TTT GCG ACC TAT TAT TGC CAG CAG AGC ATT GGC CGC GGC GTG GTG ACC TTT GGC 100 101 102 103 104 105 106 107
  Q   G   T   K   L   E   I   K
 CAG GGC ACC AAA CTG GAA ATT AAA
```

```
 1   2   3   4   5   6   7   8   9  10  11  12  13  14  15  16  17  18  19  20
 D   I   Q   L   T   Q   S   P   S   S   L   S   A   S   V   G   D   R   V   T
GAT ATT CAG CTG ACC CAG AGC CCG AGC AGC CTG AGC GCG AGC GTG GGC GAT CGC GTG ACC 21  22  23  24  25  26  27  28  29  30  31  32  33  34  35  36  37  38  39  40
 I   T   C   R   A   S   R   T   I   S   I   Y   V   N   W   Y   R   Q   R   P
ATT ACC TGC CGC GCG AGC CGC ACC ATT AGC ATT TAT GTG AAC TGG TAT CGC CAG CGC CCG 41  42  43  44  45  46  47  48  49  50  51  52  53  54  55  56  57  58  59  60
 G   K   A   P   E   S   L   I   Y   A   A   S   N   L   H   S   G   V   P   S
GGC AAA GCG CCG GAA AGC CTG ATT TAT GCG GCG AGC AAC CTG CAT AGC GGC GTG CCG AGC 61  62  63  64  65  66  67  68  69  70  71  72  73  74  75  76  77  78  79  80
 R   F   S   G   S   G   S   G   T   D   F   T   L   T   I   S   S   L   Q   P
CGC TTT AGC GGC AGC GGC AGC GGC ACC GAT TTT ACC CTG ACC ATT AGC AGC CTG CAG CCG 81  82  83  84  85  86  87  88  89  90  91  92  93  94  95  95a 96  97  98  99
 E   D   F   A   T   Y   Y   C   Q   Q   T   H   A   T   R   Q   Y   T   F   G
GAA GAT TTT GCG ACC TAT TAT TGC CAG CAG ACC CAC GCC ACC AGA CAG TAC ACC TTT GGC 100 101 102 103 104 105 106 107
 Q   G   T   K   L   E   I   K
CAG GGC ACC AAA CTG GAA ATT AAA
```

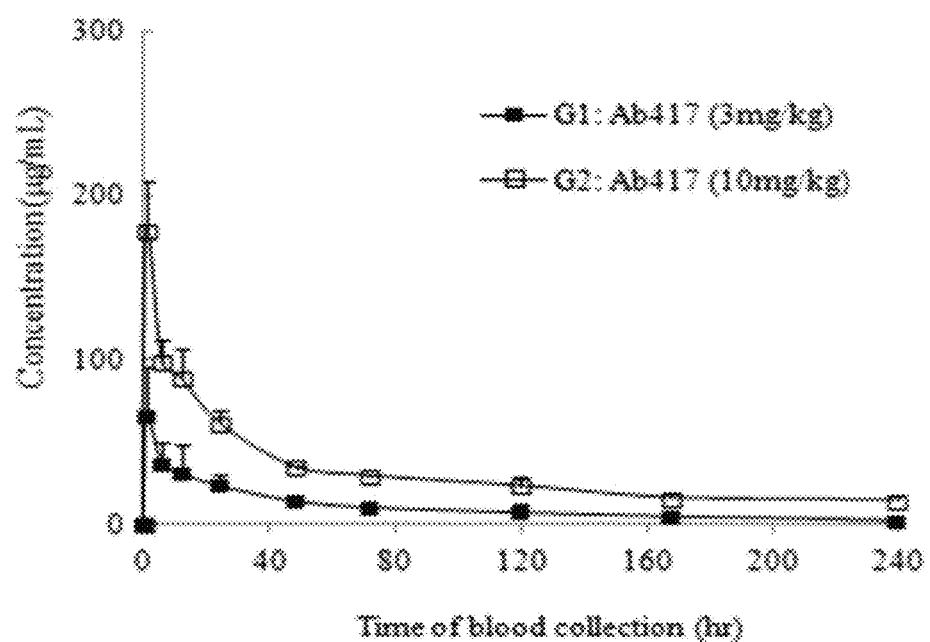

[FIG. 10]
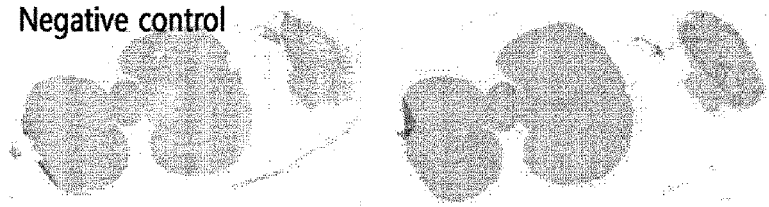
Brain-cerebrum and cerebellum
 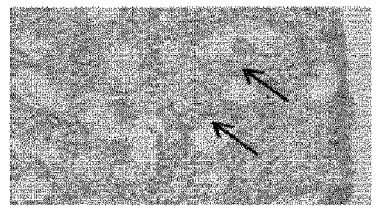
Salivary gland. peripheral nerve
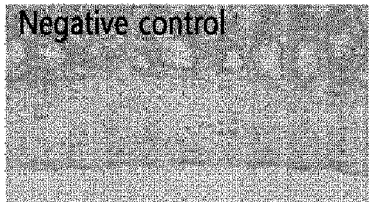 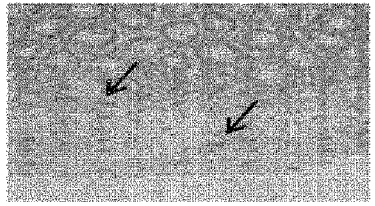
Colon. peripheral nerve
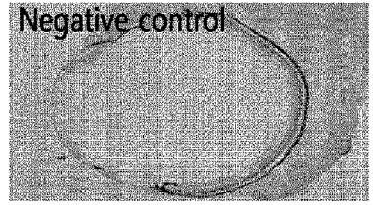 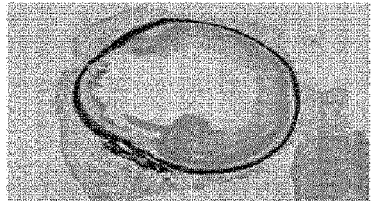
Eye. retina
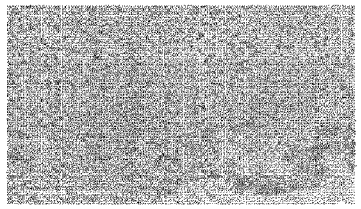 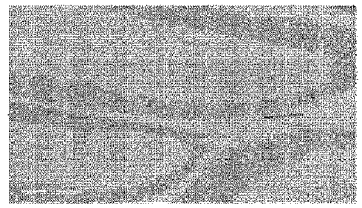
Brain. cerebrum      Cerebellum
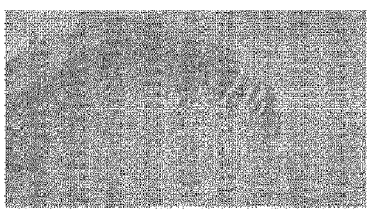 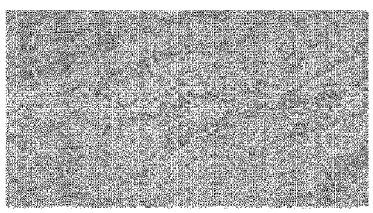
Spinal cord      Kidney tubules

[FIG. 11a]
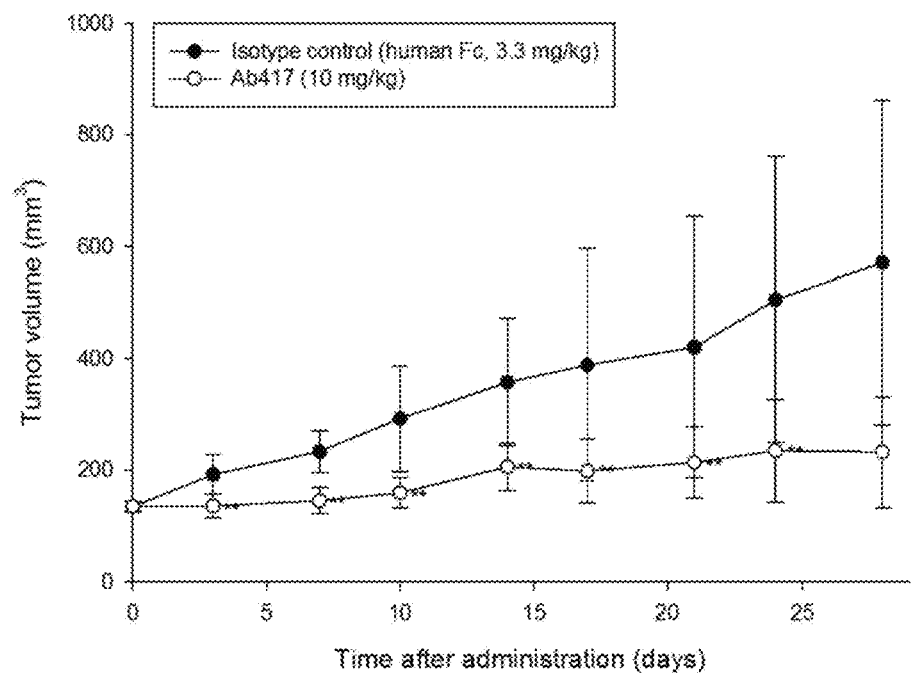
[FIG. 11b]
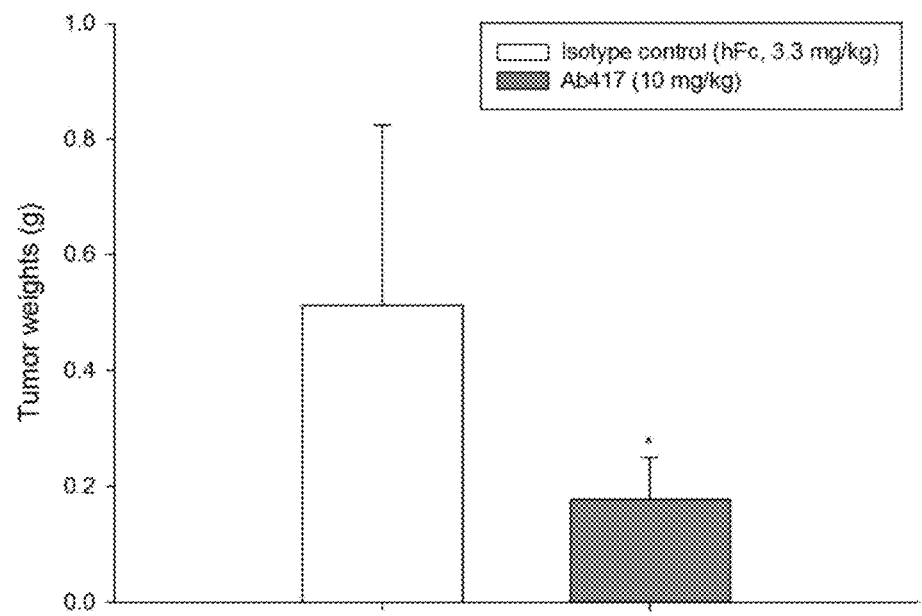

[FIG. 11c]
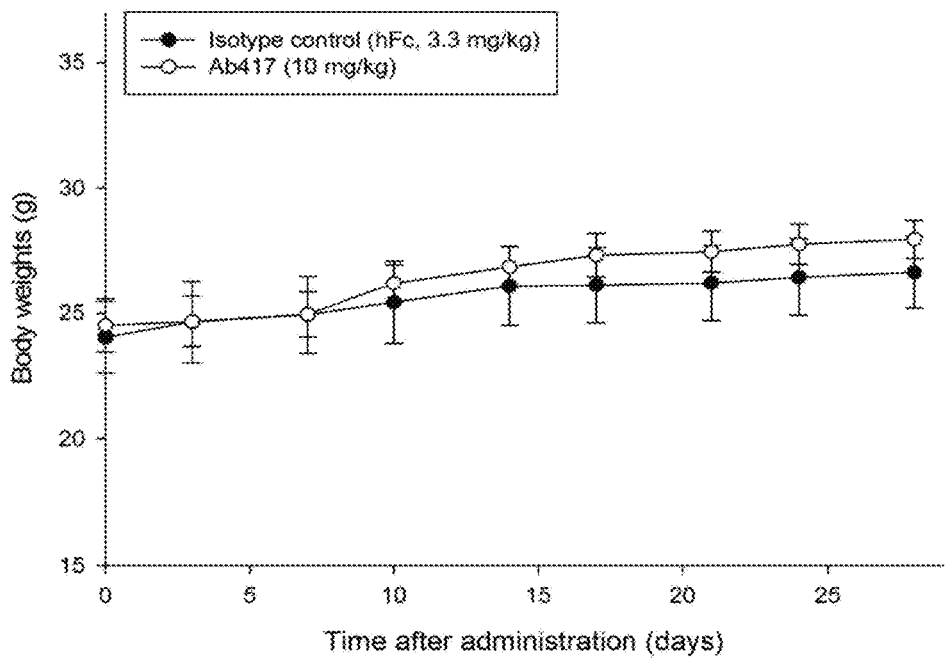
[FIG. 12a]
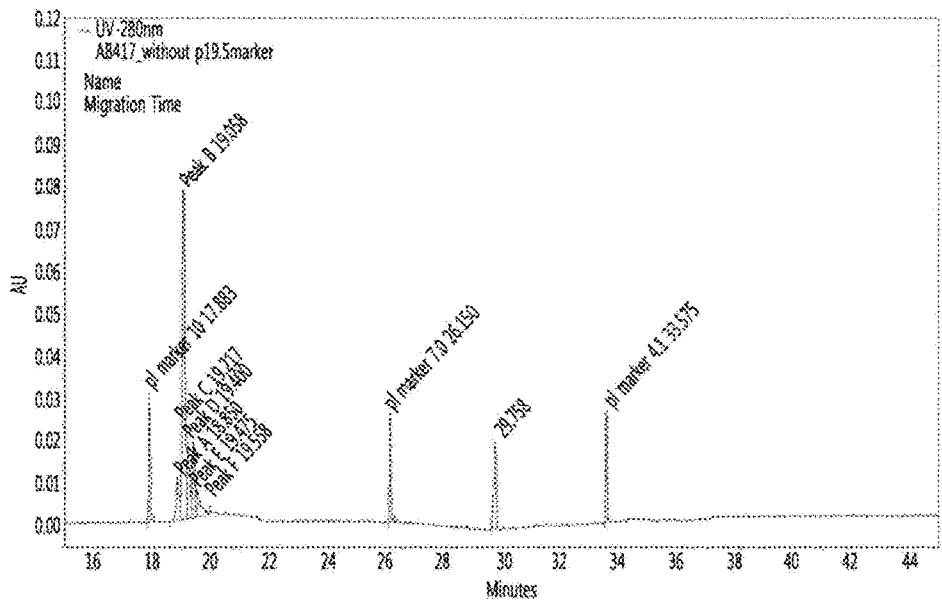

[FIG. 12b]
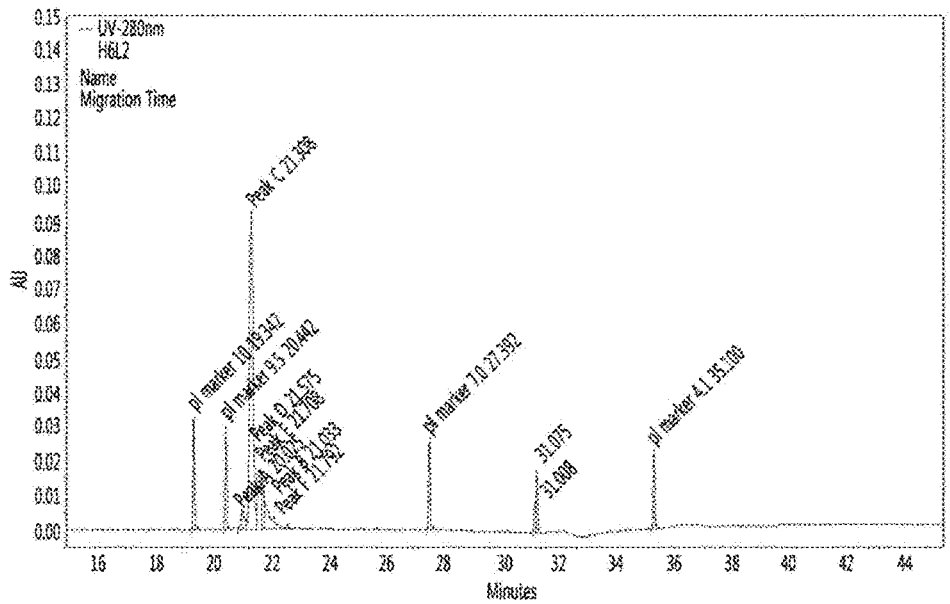
[FIG. 12c]
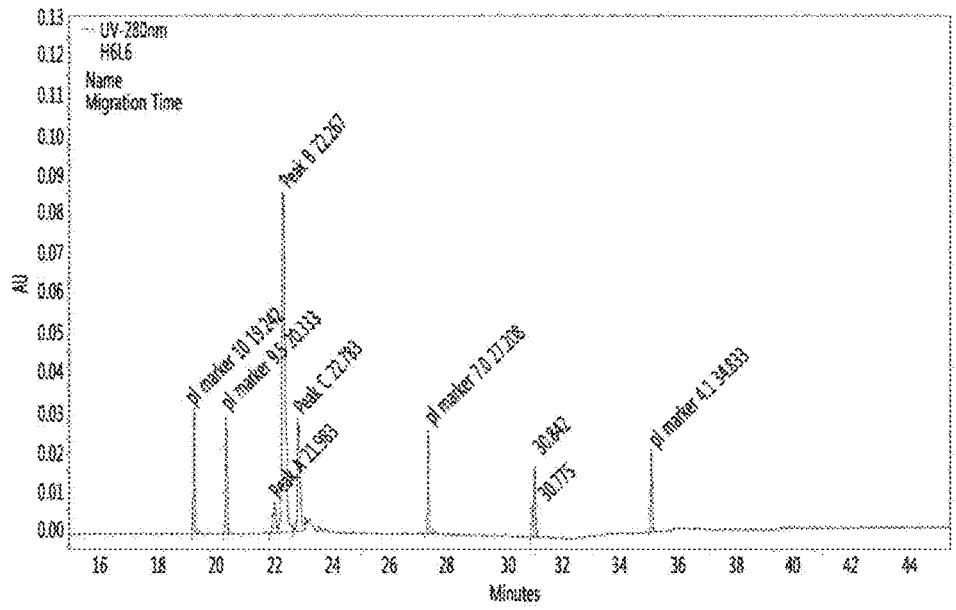

[FIG. 13a]
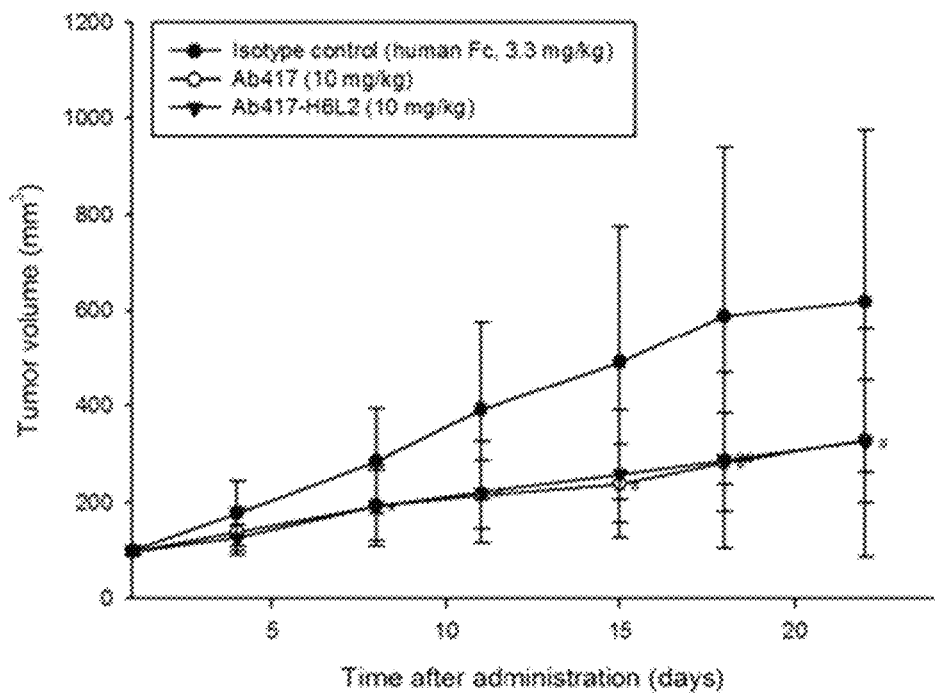
[FIG. 13b]
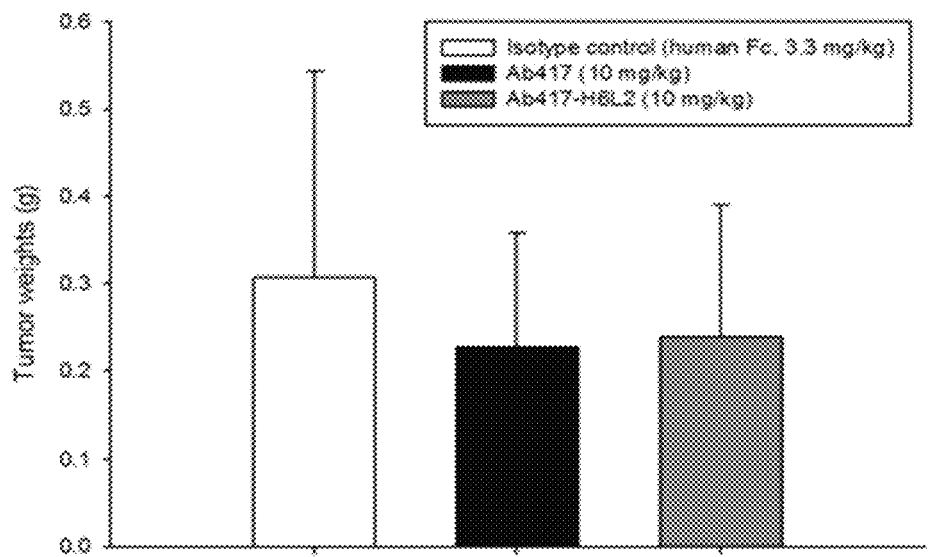

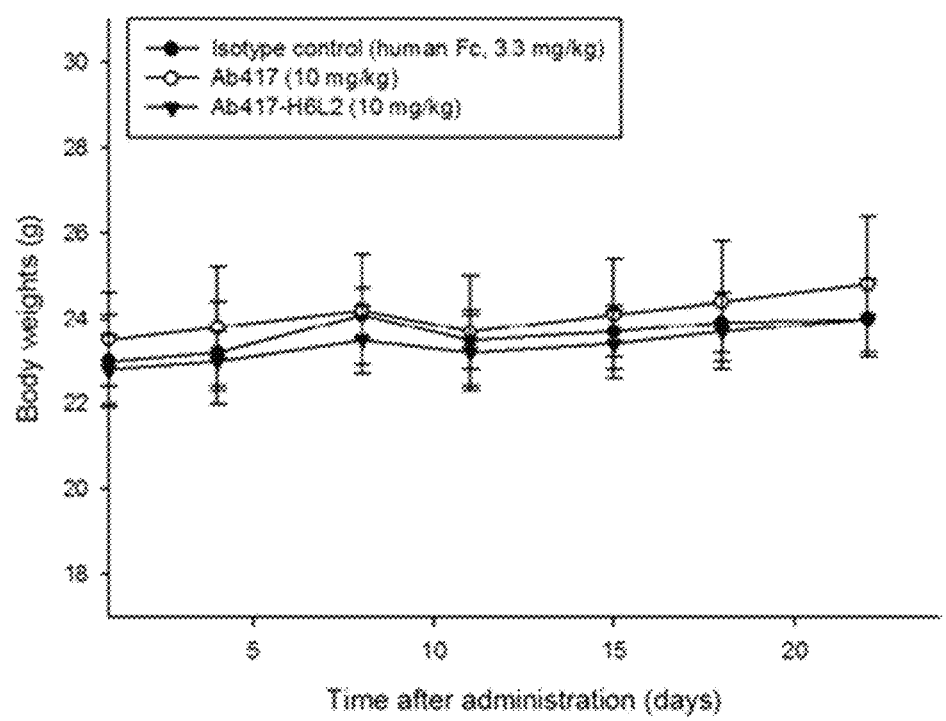
[FIG. 13c]

ANTIBODY BINDING SPECIFICALLY TO HUMAN AND MOUSE L1CAM PROTEIN, AND USE THEREFOR

BACKGROUND OF THE INVENTION

1. Field of the Invention

The present invention relates to a novel antibody specifically binding to human and mouse L1CAM, and more particularly, to an antibody binding to both human and mouse L1CAM with high affinity, which is prepared by modifying a sequence of an L1 cell adhesion molecule (L1CAM)-specific antibody including a heavy-chain variable region of SEQ ID NO. 1 and a light-chain variable region of SEQ ID NO. 5, a polynucleotide encoding the antibody, an expression vector including the polynucleotide, a transformant introduced with the vector, a pharmaceutical composition for preventing or treating cancer including the antibody, a method for treating cancer using the antibody, a composition for diagnosing cancer including the antibody, a kit for diagnosing cancer including the composition, a method for providing information for cancer diagnosis using the antibody, and an antibody-drug conjugate prepared by conjugating a drug to the antibody.

2. Description of the Related Art

L1 cell adhesion molecule (L1CAM, CD171) is one of the immunoglobulin superfamily cell adhesion molecules (CAMs) that mediate cell-to-cell adhesion on the cell surface and is a glycoprotein having a molecular weight of 200 to 220 kDa. L1CAM was first known as a protein that mediates neuron-neuron adhesion and is involved in neurite outgrowth and neuronal migration (Lee et al., PNAS 74, 5021, 1977; McGuire and Greene 15, 357, 1978). Human L1CAM is a type 1 integral membrane glycoprotein which is composed of 1,257 amino acids and spans the cell membrane once, and its amino terminal portion exists outside the cell membrane and its carboxyl terminal portion exists in the cytoplasm. The extracellular domain contains six immunoglobulin type 2 domains, five fibronectin III-like domains, and twenty N-glycosylation sites.

Besides the highest expression in the normal human brain, L1CAM expression is also found in some hematopoietic cells and renal cells, peripheral nerves, and ganglions, but not found in other normal cells (Huszar et al., Human Pathology 37, 1000-1008, 2006). Recently, it has been reported that L1CAM overexpression is found in cancer cells such as melanoma, neuroblastoma, ovarian cancer, colon cancer, pancreatic cancer, and endometrial cancer, L1CAM plays an important role in the growth and metastasis of cancer cells, and L1CAM overexpression is associated with poor prognosis of cancer. For this reason, L1CAM has been emerged as a target in cancer therapy (Raveh et al., Cancer Letters 282: 137-145, 2009).

There have been many reports regarding diagnosis and treatment of cancer using L1CAM antibodies. For example, EP Patent No. EP1172654 and U.S. Pat. No. 7,618,785 disclose a method for the diagnosis and prognosis of ovarian or endometrial tumors, characterized in that L1CAM antibodies are used to determine the presence and level of L1CAM in a patient sample on the basis that presence of L1CAM is an indication of the presence of an ovarian or endometrial tumor, and a method of treating the tumors by administering a complex of the L1CAM antibody and a cytotoxic drug to the patient. Further, US Patent Publication No. 2004/0115206 discloses a method for inhibiting cell growth or inducing cell death in tumor cells by contacting the tumor cells with an effective amount of an anti-L1CAM antibody capable of inhibiting cell growth or inducing cell death in the tumor cells. Furthermore, International Patent Publication No. WO2006/013051 provides a composition inhibiting the L1CAM protein being overexpressed in ovarian and endometrial carcinoma and its expression, and a method for preventing and treating ovarian and endometrial carcinoma using the composition. This patent describes that a composition including an anti-L1CAM antibody or a derivative thereof suppresses functions of ovarian and endometrial carcinoma and blocks the migration of the cancer cells, thereby realizing treatment of cancer. Further, the present inventors demonstrated that L1CAM is expressed in cholangiocarcinoma and involved in proliferation and migration of cholangiocarcinoma cells, and growth of cholangiocarcinoma cells is inhibited by monoclonal antibody against L1CAM, suggesting that there is an association between L1CAM and cholangiocarcinoma (Korean Patent NOS. 10-756051 and 10-0931976).

However, L1CAM antibodies that have been developed until now are mouse antibodies, and thus there is a disadvantage that the antibodies bind to human L1CAM, but do not bind to mouse L1CAM. Usually, nude mice transplanted with human cancer cells are used in animal tests for anti-cancer efficacy of antibodies. In this regard, since antibodies that bind to human L1CAM but do not bind to mouse L1CAM bind to only human cancer tissues, but do not bind to L1CAM expressed in some normal tissues of a mouse, their anti-cancer efficacy and toxicity could not be accurately evaluated, compared to clinical trials in cancer patients. In order to solve this problem, there has been a demand for antibodies that bind to both human and mouse L1CAM with high binding ability and exhibit excellent anti-cancer efficacy. Thus, the present inventors developed L1CAM-binding antibodies having binding capacity to human and mouse L1CAM (Korean Patent Publication No. 10-2010-0064985). However, it is still necessary to develop an L1CAM antibody that binds to both human and mouse L1CAM with improved binding capacity.

Accordingly, the present inventors have made intensive efforts to develop an antibody that is cross-reactive with mouse and human L1CAM and has excellent binding capacity to L1CAM. As a result, they prepared an antibody with greatly improved affinity for both human and mouse L1CAM, compared to the existing antibodies, via mutations in particular amino acids of heavy chain and light chain variable regions of Ab4, and they found that this antibody has excellent anti-cancer efficacy, thereby completing the present invention.

SUMMARY OF THE INVENTION

An object of the present invention is to provide a novel antibody that specifically binds to human and mouse L1CAM proteins.

Another object of the present invention is to provide a method for preparing the antibody.

Still another object of the present invention is to provide a polynucleotide encoding the antibody, an expression vector including the polynucleotide, and a transformant including the vector.

Still another object of the present invention is to provide a composition including the antibody.

Still another object of the present invention is to provide a pharmaceutical composition for preventing or treating cancer including the antibody.

Still another object of the present invention is to provide a method for treating cancer using the antibody.

Still another object of the present invention is to provide a composition for diagnosing cancer including the antibody.

Still another object of the present invention is to provide a method for diagnosing cancer, comprising detecting the L1CAM protein in a biological sample separated from an individual suspected of having cancer by using the antibody via antigen-antibody reaction.

Still another object of the present invention is to provide a kit for diagnosing cancer including the composition for diagnosing cancer.

Still another object of the present invention is to provide an antibody-drug conjugate prepared by conjugating a drug to the antibody.

BRIEF DESCRIPTION OF THE DRAWINGS

FIG. 1a shows binding affinities of alanine mutants for human and mouse L1CAM relative to that of Ab4 as measured by indirect ELISA, the alanine mutants being prepared by substitution of amino acid residues constituting CDR sequence of L1CAM-binding Ab4 antibody (substitution of alanine for amino acid residues constituting VH CDR1, 2 and 3, and VK CDR3 of Ab4 antibody, respectively).

FIG. 1b shows binding affinities of alanine mutants for human and mouse L1CAM relative to that of Ab4 as measured by indirect ELISA, the alanine mutants being prepared by substitution of amino acid residues constituting CDR sequence of L1CAM-binding Ab4 antibody (substitution of alanine for amino acid residues constituting VH CDR1, 2 and 3, and VK CDR3 of Ab4 antibody, respectively).

FIG. 1c shows antigen binding affinity of an alanine mutant relative to that of Ab4 as measured by indirect ELISA, the alanine mutants being prepared by substitution of amino acid residues constituting CDR sequence of L1CAM-binding Ab4 antibody (substitution of another amino acid residue for valine at position 50 of Ab4 VH).

FIG. 2a shows affinities of Ab4, Ab4M and Ab4 mutants for human L1CAM as a result of competitive ELISA for analyzing and comparing antigen binding affinities of Ab4, Ab4M and Ab417 antibodies for human and mouse L1CAM proteins, wherein affinity ($K_D$) of the antibody is defined as concentration of competing antigen which is required to cause 50% inhibition of binding capacity of the antibody to antigen.

FIG. 2b shows affinities of Ab4, Ab4M and Ab417 for human L1CAM as a result of competitive ELISA for analyzing and comparing antigen binding affinities of Ab4, Ab4M and Ab417 antibodies for human and mouse L1CAM proteins, wherein affinity ($K_D$) of the antibody is defined as concentration of competing antigen which is required to cause 50% inhibition of binding capacity of the antibody to antigen.

FIG. 2c shows affinities of Ab4, Ab4M and Ab417 for mouse L1CAM as a result of competitive ELISA for analyzing and comparing antigen binding affinities of Ab4, Ab4M and Ab417 antibodies for human and mouse L1CAM proteins, wherein affinity ($K_D$) of the antibody is defined as concentration of competing antigen which is required to cause 50% inhibition of binding capacity of the antibody to antigen.

FIG. 3a shows the results of flow cytometry for examining specificities of Ab4M and Ab417 antibodies for human and mouse L1CAM antigens, in which Human IgG was used as a negative control and chimeric A10-A3(cA10-A3) antibody binding to human L1CAM but not binding to mouse L1CAM was used as a positive control; Ab4M antibody hardly binds to L1CAM-negative cells, HEK293T, CFPAC and CHO-DG44.

FIG. 3b shows the results of flow cytometry for examining specificities of Ab4M and Ab417 antibodies for human and mouse L1CAM antigens, in which Human IgG was used as a negative control and chimeric A10-A3(cA10-A3) antibody binding to human L1CAM but not binding to mouse L1CAM was used as a positive control; Ab4M antibody obviously binds to L1CAM-positive cells, SCK-L1 and Choi-CK and B16F1.

FIG. 4a shows the results of examining anti-cancer effect of the Ab4M antibody using Synagis antibody as an isotype negative control in mouse cholangiocarcinoma models by measuring tumor volume.

FIG. 4b shows the result of examining anti-cancer effect of the Ab4M antibody using Synagis antibody as an isotype negative control in mouse cholangiocarcinoma models by measuring body weight of the mouse model.

FIG. 5a shows the result of FACS showing binding of yeast surface-displayed Ab4M scFv to an antigen Ig5-hFc ($1 \times 10^{-5}$ to $1 \times 10^{-8}$ M).

FIG. 5b shows the result of FACS showing expressions of Ab4M scFv and Ab4M-18 scFv on yeast surface and their binding capability to the antigen Ig5-hFc, in which a spot on the graph of FIG. 5b indicates one individual yeast cell, and the vertical axis indicates Cy5 fluorescence signals showing scFv expression and the horizontal axis indicates FITC fluorescence signals showing binding affinity of scFv for the antigen.

FIG. 6a shows the results of measuring affinities of Ab4M and Ab417 antibodies for human L1CAM by SPR using an Octet RED (ForteBio) system.

FIG. 6b shows the results of measuring affinities of Ab4M and Ab417 antibodies for mouse L1CAM by SPR using an Octet RED (ForteBio) system.

FIG. 7a shows the result of examining anti-cancer efficacy of Ab417 antibody in nude mouse cholangiocarcinoma models by measuring tumor volume.

FIG. 7b shows the result of examining anti-cancer efficacy of Ab417 antibody in nude mouse cholangiocarcinoma models by measuring tumor weight at 21 days.

FIG. 7c shows the result of examining anti-cancer efficacy of Ab417 antibody in nude mouse cholangiocarcinoma models by measuring body weight of the nude mouse model.

FIG. 8a shows heavy-chain variable region (SEQ ID NO. 12) of Ab4M or Ab417 antibody, which is an L1CAM-binding antibody of the present invention; numbering is according to Kabat and CDRs are underlined.

FIG. 8b shows light-chain variable region (SEQ ID NO. 14) of Ab417 antibody, which is an L1CAM-binding antibody of the present invention; numbering is according to Kabat and CDRs are underlined.

FIG. 8c shows light-chain variable region (SEQ ID NO. 13) of Ab4M antibody, which is an L1CAM-binding antibody of the present invention; numbering is according to Kabat and CDRs are underlined.

FIG. 9 shows the pharmacokinetic result of Ab417 antibody.

FIG. 10 shows the result of immunohistochemistry of a normal mouse tissue using Ab417 antibody.

FIG. 11a shows changes in the tumor volume of TFK-1 xenograft model after administration of Ab417 or hFc (human Fc) antibody ($p<0.01$, Significant difference from the isotype control group by Dunnett's t-test).

FIG. 11b shows the tumor weights of TFK-1 xenograft model after administration of Ab417 or hFc antibody (*p<0.05, Significant difference from the isotype control group by Dunnett's t-test).

FIG. 11c shows changes in the body weights of TFK-1 xenograft model after administration of Ab417 or hFc antibody.

FIG. 12a shows the result of analyzing isoelectric point (pI) of Ab417 antibody.

FIG. 12b shows the result of analyzing isoelectric point (pI) of Ab417-H6L2 antibody.

FIG. 12c shows the result of analyzing isoelectric point (pI) of Ab417-H6L6 antibody.

FIG. 13a shows changes in the tumor volume of Choi-CK xenograft model after administration of Ab417, Ab417-H6L2 or hFc antibody (*p<0.05, Significant difference from the isotype control group by Dunnett's t-test).

FIG. 13b shows the tumor weights of Choi-CK xenograft model after administration of Ab417, Ab417-H6L2 or hFc antibody.

FIG. 13c shows changes in the body weights of Choi-CK xenograft model after administration of Ab417, Ab417-H6L2 or hFc antibody.

DETAILED DESCRIPTION OF THE PREFERRED EMBODIMENTS

In an aspect, the present invention provides a novel antibody that specifically binds to both human and mouse L1CAM (L1 cell adhesion molecule) proteins.

In the present invention, mutation sites capable of improving binding affinity for an antigen thereof, physical properties, or/and purification efficiency were identified in an antibody specifically binding to L1CAM, which includes a heavy-chain variable region containing a heavy chain CDR1 of SEQ ID NO. 2; a heavy chain CDR2 of SEQ ID NO. 3; and a heavy chain CDR3 of SEQ ID NO. 4 and a light-chain variable region containing a light chain CDR1 of SEQ ID NO. 6; a light chain CDR2 of SEQ ID NO. 7; and a light chain CDR3 of SEQ ID NO. 8, preferably, a heavy-chain variable region of SEQ ID NO. 1 and a light-chain variable region of SEQ ID NO. 5, thereby developing a novel antibody effectively binding to L1CAM.

As used herein, the term "L1CAM (L1 cell adhesion molecule)" refers to one of integral membrane glycoproteins belonging to the immunoglobulin superfamily cell adhesion molecules (CAMs). Information about the L1CAM protein may be obtained from the known database such as GenBank at National Center for Biotechnology Information (NCBI), and an example thereof may be an L1CAM protein with Accession No. AA136448, but is not limited thereto.

The L1CAM is found in neurons, hematopoietic cells, renal cells, etc. (Bateman et al, EMBO J. 15:6050-6059; 1996) and known to be involved in neuronal migration, neurite outgrowth, and cell migration. Its association with cancer is also known. Specifically, it has been reported that L1CAM is expressed in various cancers such as melanoma, neuroblastoma, ovarian cancer and colon cancer, plays an important role in the growth and metastasis of cancer cells, and L1CAM overexpression is associated with poor prognosis of cancer (Raveh et al., Cancer Letters 282: 137-145, 2009). An antibody that specifically recognizes the L1CAM protein may be used for the diagnosis, and prevention or treatment of diseases such as cancer in which L1CAM is overexpressed, and therefore, the present inventors developed an antibody binding to human and mouse L1CAM proteins with high affinity. Since the antibody of the present invention binds to both human and mouse L1CAM proteins with high affinity, it may be effectively used in clinical studies using mouse models and diagnosis of diseases in which L1CAM protein is overexpressed. Also, the antibody exhibits a remarkable inhibitory effect on cancer growth, thereby being effectively used in the prevention or treatment of cancer.

As used herein, the term "antibody" means a protein molecule which includes an immunoglobulin molecule immunologically reactive to a certain antigen, serving as a receptor specifically recognizing the antigen, and is intended to encompass polyclonal antibodies, monoclonal antibodies, whole antibodies and antibody fragments. In addition, the antibody encompasses chimeric antibodies (e.g., humanized murine antibodies), bivalent or bispecific molecules (e.g., bispecific antibodies), diabodies, triabodies, and tetrabodies. The term includes also single chain antibodies retaining the FcRn binding function, SCAP, derivatives of antibody constant region, and artificial antibodies based on protein scaffold. A whole antibody consists of two full-length light chains and two full-length heavy chains, with disulfide bonds between the light and heavy chains. The whole antibody includes IgA, IgD, IgE, IgM and IgG, and IgG is further divided into subtypes of IgG1, IgG2, IgG3 and IgG4. The antibody fragment refers to a fragment which retains the antigen-binding function, and may include Fd, Fab, Fab', F(ab')$_2$, and Fv. Fd means a portion of the heavy chain which is included in the Fab fragment. Fab is composed of one variable region of each of the heavy and the light chain, the constant domain of the light chain, and the first constant domain (CH1 domain) of the heavy chain, with an antigen binding site. Fab' is different from Fab in that it has a hinge region including one or more cysteine residues at the C-terminus of the CH1 domain of the heavy chain. F(ab')$_2$ antibody is produced by a disulfide bond between the cysteine residues of the hinge region of Fab'. Fv (variable fragment) is the smallest antibody fragment composed of one variable region of each of the heavy and the light chain. Disulfide Fv (dsFv) is formed by linking the variable region of the heavy chain to the variable region of the light chain via a disulfide bond. Single chain Fv (scFV) is formed by covalently linking the respective variable regions of the heavy and the light chain by a peptide linker. These antibody fragments may be obtained using proteases (for example, digestion of a whole antibody with papain or pepsin affords Fab or F(ab')$_2$, respectively), and preferably, they may be constructed by genetic recombination technology.

As used herein, the term "monoclonal antibody" refers to an antibody molecule with a uniform molecular composition, obtained from a substantially identical population of antibodies, which shows binding specificity and affinity for a particular epitope.

Typically, an immunoglobulin has heavy and light chains, each heavy chain and light chain includes constant and variable regions (also known as "domain"). The variable region of each of the light and the heavy chain includes three hypervariable regions, also called complementarity-determining regions (hereinafter referred to as "CDRs"), and four framework regions. CDRs function to bind to an epitope of an antigen. CDRs on each chain start from the N-terminus and are arranged sequentially as CDR1, CDR2, and CDR3. They are discriminated by the chain on which they are positioned.

As used herein, the term "human antibody" is a molecule which consists entirely of the amino acid sequence of all components of human immunoglobulin, including complementarity-determining regions and framework regions.

Human antibodies are generally used in the therapy of human diseases, and have at least three potential advantages. First, human antibodies more preferably interact with the human immune system to more effectively destroy target cells by, for example, complement-dependent cytotoxicity (CDC) or antibody-dependent cell-mediated cytotoxicity (ADCC). Another advantage is that the human immune system does not recognize human antibodies as foreign molecules. Moreover, the half-lives of human antibodies are similar to those of naturally occurring antibodies in the human circulatory system even when they are administered in smaller doses or with less frequency. In an embodiment of the present invention, prepared was a human monoclonal antibody specifically binding to the L1CAM protein, of which all amino acid sequences are composed of the amino acid sequences of human immunoglobulin. Since the human monoclonal antibody has the heavy chain and light chain domains derived from human, it shows low immunogenicity. Therefore, the antibody may be effectively used for the treatment of cancer.

Further, if the antibody of the present invention includes a constant domain, it may be derived from IgG, IgA, IgD, IgE, IgM, or combinations or hybrids thereof.

As used herein, the term "combination" means that a polypeptide encoding single-chain immunoglobulin constant region of the same origin is linked to a single-chain polypeptide of a different origin to form a dimer or multimer. For example, a dimer or multimer may be formed from two or more constant domains selected from the group consisting of constant domains of IgG, IgA, IgD, IgE and IgM.

As used herein, the term "hybrid" means that sequences encoding two or more heavy-chain constant domains of different origins are present in a single-chain immunoglobulin heavy-chain constant domain. For example, domain hybrids may be composed of one to four domains selected from the group consisting of CH1, CH2, CH3 and CH4 of IgG, IgA, IgD, IgE and IgM.

As used herein, the term "antibody specifically binding to L1CAM (L1 cell adhesion molecule)" refers to an antibody that binds to L1CAM protein to inhibit activity of the L1CAM protein. With respect to the objects of the present invention, the antibody specifically binding to L1CAM is an antibody binding to Ig5 region of L1CAM, but is not limited thereto.

The antibody specifically binding to L1CAM of the present invention has a property of binding to both human and mouse L1CAM proteins with high affinity. Unlike the antibody of the present invention, an antibody specifically binding to only human protein does not bind to L1CAM protein which is expressed in some mouse normal tissues other than human cancer cells in a mouse model transplanted with human cancer cells expressing L1CAM (Xenograft model). Therefore, there are disadvantages that anti-cancer efficacy cannot be accurately evaluated and a toxicity test should be performed in primates such as monkey other than mouse. Accordingly, the antibody of the present invention is advantageous in that it binds to both human and mouse L1CAM proteins with high affinity and thus can be used in an anti-cancer efficacy test in xenograft models under circumstance similar to human clinical trials and also used in a toxicity test in rodents, leading to cost savings in preclinical studies.

In order to increase affinity for human or/and mouse L1CAM, the antibody specifically binding to L1CAM is an antibody which has substitution(s) of 1, 2, 3, 4, 5, 6, 7, 8, 9, 10, 11, 12 or 13 amino acid residue(s) in an antibody including a heavy-chain variable region containing a heavy chain CDR1 of SEQ ID NO. 2; a heavy chain CDR2 of SEQ ID NO. 3; and a heavy chain CDR3 of SEQ ID NO. 4 and a light-chain variable region containing a light chain CDR1 of SEQ ID NO. 6; a light chain CDR2 of SEQ ID NO. 7; and a light chain CDR3 of SEQ ID NO. 8, preferably, a heavy-chain amino acid sequence of SEQ ID NO. 1 and a light-chain amino acid sequence of SEQ ID NO. 5.

Specifically, the antibody may be an antibody binding to human L1CAM (L1 cell adhesion molecule) protein, which includes a heavy-chain variable region containing (i) a heavy chain CDR1 of SEQ ID NO. 2; (ii) a heavy chain CDR2 selected from a heavy chain CDR2 of SEQ ID NO. 3, a heavy chain CDR2 (SEQ ID NO. 9) having a substitution of phenylalanine for valine as an amino acid at position 1 of the heavy chain CDR2 of SEQ ID NO. 3, and a heavy chain CDR2 (SEQ IS NO. 16) having a substitution of phenylalanine for valine as an amino acid at position 1 and a substitution of glutamic acid for aspartic acid at position 5 of the heavy chain CDR2 of SEQ ID NO. 3; and (iii) any one of a heavy chain CDR3 of SEQ ID NO. 4 and a heavy chain CDR3 (SEQ ID NO. 10) having a substitution of alanine for histidine as an amino acid at position 3 of the heavy chain CDR3 of SEQ ID NO. 4; and a light-chain variable region containing (iv) a light chain CDR1 of SEQ ID NO. 6 or a light chain CDR1 (SEQ ID NO. 17) having a substitution of serine for isoleucine as an amino acid at position 8 of the light chain CDR1 of SEQ ID NO. 6; (v) a light chain CDR2 of SEQ ID NO. 7; and (vi) a light chain CDR3 selected from the group consisting of a light chain CDR3 of SEQ ID NO. 8, a light chain CDR3 (SEQ ID NO. 11) having a substitution of alanine for aspartic acid as an amino acid at position 5 of the light chain CDR3 of SEQ ID NO. 8, and a light chain CDR3 of SEQ ID NO. 15, except for an antibody including a heavy-chain variable region containing a heavy chain CDR1 of SEQ ID NO. 2; a heavy chain CDR2 of SEQ ID NO. 3; and a heavy chain CDR3 of SEQ ID NO. 4 and a light chain CDR1 of SEQ ID NO. 6; a light chain CDR2 of SEQ ID NO. 7; and a light chain CDR3 of SEQ ID NO. 8.

More preferably, the antibody may be an antibody binding to human L1CAM (L1 cell adhesion molecule) protein, which includes a heavy-chain variable region containing (i) a heavy chain CDR1 of SEQ ID NO. 2; (ii) a heavy chain CDR2 of SEQ ID NO. 9, or a heavy chain CDR2 (SEQ ID NO. 16) having a substitution of glutamic acid for aspartic acid as an amino acid at position 5 of the heavy chain CDR2 of SEQ ID NO. 9; and (iii) a heavy chain CDR3 of SEQ ID NO. 10; and a light-chain variable region containing (iv) a light chain CDR1 of SEQ ID NO. 6 or a light chain CDR1 (SEQ ID NO. 17) having a substitution of serine for isoleucine as an amino acid at position 8 of the light chain CDR1 of SEQ ID NO. 6; (v) a light chain CDR2 of SEQ ID NO. 7; and (vi) light chain CDR3 of a light chain CDR3 of SEQ ID NO. 11 or a light chain CDR3 of SEQ ID NO. 15.

Here, the heavy-chain variable region of the framework region (FR) of the antibody may preferably include any one FR1 of a heavy chain framework region 1 (FR1) of SEQ ID NO. 22 and FR1 (SEQ ID NO. 26) having a substitution of glycine for arginine as an amino acid at position 16 of SEQ ID NO. 22; FR2 of SEQ ID NO. 23; any one FR3 of SEQ ID NO. 24 or FR3 (SEQ ID NO. 27) having a substitution of alanine for lysine as an amino acid at position 10 and a substitution of alanine for proline as an amino acid at position 22 of FR3 of SEQ ID NO. 24; and FR4 of SEQ ID NO. 25, and the light-chain variable region may include FR1 of SEQ ID NO. 28; a light chain FR2 of SEQ ID NO. 29 or a light chain FR2 having a substitution of glutamine for arginine as an amino acid at position 3, a substitution of lysine for arginine as an amino acid at position 5, and a substitution of glutamine for lysine as an amino acid at position 8 of SEQ ID NO. 29 (SEQ ID NO. 32); or a light chain FR3 of SEQ ID NO. 30 or a light chain FR3 (SEQ ID NO. 33) having a substitution of isoleucine for valine as an amino acid at position 19 and a substitution of alanine for glycine as an amino acid at position 28 of SEQ ID NO. 30; and a light chain FR4 of SEQ ID NO. 31.

Hereinafter, the above described antibody of the present invention will be described in more detail below.

The antibody specifically binding to L1CAM of the present invention may be preferably an antibody specifically binding to L1CAM (L1 cell adhesion molecule), which include a heavy-chain variable region of SEQ ID NO. 1 and a light-chain variable region of SEQ ID NO. 5. The antibody may be an antibody including one or more mutations selected from the group consisting of a substitution of phenylalanine (F) for valine (V) as an amino acid residue at position 50 and a substitution of alanine (A) for histidine (H) as an amino acid residue at position 101 of the heavy-chain variable region of SEQ ID NO. 1, and a substitution of alanine (A) for aspartic acid (D) as an amino acid residue at position 93 of the light-chain variable region.

The antibody including the heavy chain amino acid sequence of SEQ ID NO. 1 and the light chain amino acid sequence of SEQ ID NO. 5 of the present invention is a monoclonal antibody binding to L1CAM, which was developed by the present inventors and disclosed in Korean Patent Publication No. 10-2010-0064985. In the present specification, the antibody is designated as Ab4. The Ab4 antibody includes a heavy-chain variable region containing a heavy chain CDR1 of SEQ ID NO. 2; a heavy chain CDR2 of SEQ ID NO. 3; and a heavy chain CDR3 of SEQ ID NO. 4 and a light chain CDR1 of SEQ ID NO. 6; a light chain CDR2 of SEQ ID NO. 7; and a light chain CDR3 of SEQ ID NO. 8, and includes a heavy-chain variable region containing a heavy chain FR1 of SEQ ID NO. 22; a heavy chain FR2 of SEQ ID NO. 23; a heavy chain FR3 of SEQ ID NO. 24; and a heavy chain FR4 of SEQ ID NO. 25, and a light chain FR1 of SEQ ID NO. 28; a light chain FR2 of SEQ ID NO. 29; a light chain FR3 of SEQ ID NO. 30; and a light chain FR4 of SEQ ID NO. 31.

In order to develop an antibody showing higher affinity than the Ab4 antibody, the present inventors identified particular amino acids capable of improving affinity among many amino acids of Ab4, and they developed an antibody having binding affinity which is up to 40 times higher than the known Ab4 by mutations of a part of the amino acids constituting the heavy chain and light-chain variable regions.

In the heavy chain amino acid sequence of SEQ ID NO. 1 and the light chain amino acid sequence of SEQ ID NO. 5 of the Ab4 antibody, the amino acid residues capable of improving affinity for L1CAM protein are valine (positioned in heavy chain CDR2) which is an amino acid residue at position 50 of the heavy-chain variable region (SEQ ID NO. 1) of Ab4, histidine (positioned in heavy chain CDR3) which is an amino acid residue at position 97 of the heavy-chain variable region of Ab4 according to Kabat numbering and corresponds to the amino acid residue at position 101 of SEQ ID NO. 1, and aspartic acid (positioned in light chain CDR3) which is an amino acid residue at position 93 of the light-chain variable region (SEQ ID NO. 2) of Ab4, but are not limited thereto.

The valine which is an amino acid residue at position 50 of the heavy-chain variable region of the Ab4 antibody is positioned in heavy chain CDR2 and is replaced by phenylalanine (Phe) so as to show higher affinity for both human and mouse L1CAM. In an embodiment of the present invention, when the valine as an amino acid residue at position 50 of the Ab4 antibody was replaced by alanine, the antibody showed remarkably reduced binding affinity for both human and mouse L1CAM proteins, compared to the wild-type Ab4 antibody as a control group. In contrast, when the valine was replaced by phenylalanine, the antibody showed high binding affinity for both human and mouse L1CAM proteins (FIGS. 1a and 1c; and FIG. 2). The Ab4 antibody mutant having a substitution of phenylalanine for valine at position 50 of the heavy-chain variable region of the Ab4 antibody was designated as 'V50F', and this antibody includes a heavy-chain variable region containing a heavy chain CDR1 of SEQ ID NO. 2; a heavy chain CDR2 of SEQ ID NO. 9; and a heavy chain CDR3 of SEQ ID NO. 4 and a light-chain variable region containing a light chain CDR1 of SEQ ID NO. 6; a light chain CDR2 of SEQ ID NO. 7; and a light chain CDR3 of SEQ ID NO. 8.

Further, the histidine which is an amino acid residue at position 97 of heavy-chain variable region (SEQ ID NO. 1) of the Ab4 antibody according to Kabat numbering corresponds to the amino acid residue at position 101 of SEQ ID NO. 1 and is positioned in heavy chain CDR3 of the heavy-chain variable region of the Ab4 antibody. The histidine is replaced by alanine so as to show higher affinity for both human and mouse L1CAM. In an embodiment of the present invention, an antibody was having a substitution of alanine for histidine at position 97 of heavy-chain variable region according to Kabat numbering and designated as 'H97A'. The replacement of histidine by alanine increased binding affinity for both human and mouse L1CAM proteins, unlike other 26 amino acid residues of HCDR1 to 3 (FIG. 1a). This H97A antibody includes a heavy-chain variable region containing a heavy chain CDR1 of SEQ ID NO. 2; a heavy chain CDR2 of SEQ ID NO. 3; and a heavy chain CDR3 of SEQ ID NO. 10 and a light-chain variable region containing a light chain CDR1 of SEQ ID NO. 6; a light chain CDR2 of SEQ ID NO. 7; and a light chain CDR3 of SEQ ID NO. 8, and provides affinity for human L1CAM. In this regard, an association/dissociation constant ($K_D$ value) for human L1CAM was $2.9 \times 10^{-8}$ M, as measured by competitive ELISA.

Further, when valine and histidine of the heavy-chain variable region of the Ab4 antibody are replaced by phenylalanine and alanine, respectively, the antibody exhibits high affinity for L1CAM, compared to Ab4. This antibody prepared by replacement of both the amino acid residues was designated as 'V50F/H97A', and this V50F/H97A antibody includes a heavy-chain variable region containing a heavy chain CDR1 of SEQ ID NO. 2; a heavy chain CDR2 of SEQ ID NO. 9; and a heavy chain CDR3 of SEQ ID NO. 10 and a light chain CDR1 of SEQ ID NO. 6; a light chain CDR2 of SEQ ID NO. 7; and a light chain CDR3 of SEQ ID NO. 8. This V50F/H97A antibody provides affinity for human L1CAM. In this regard, an association/dissociation constant ($K_D$ value) for human L1CAM was $1.8 \times 10^{-8}$ M, as measured by competitive ELISA.

The aspartic acid which is an amino acid residue at position 93 of the light-chain variable region of the Ab4 antibody is positioned in light chain CDR3 (LCDR3) and is replaced by alanine so as to show higher affinity for both human and mouse L1CAM. In particular, replacement of aspartic acid by alanine remarkably increased affinity for human L1CAM (FIG. 1b). In an embodiment of the present invention, an antibody having a substitution of alanine for aspartic acid at position 93 of the light-chain variable region was designated as 'D93A'. This D93A antibody includes a heavy-chain variable region containing a heavy chain CDR1 of SEQ ID NO. 2; a heavy chain CDR2 of SEQ ID NO. 3; and a heavy chain CDR3 of SEQ ID NO. 4 and a light chain CDR1 of SEQ ID NO. 6; a light chain CDR2 of SEQ ID NO. 7; and a light chain CDR3 of SEQ ID NO. 11, and provides affinity for human L1CAM. In this regard, an association/dissociation constant ($K_D$ value) for human L1CAM was $3.0 \times 10^{-8}$ M, as measured by competitive ELISA.

Further, the antibody specifically binding to L1CAM of the present invention may be an antibody having a substitution of phenylalanine for valine as an amino acid residue at position 50 and a substitution of alanine for histidine as an amino acid residue at position 101 of SEQ ID NO. 1 which is the heavy-chain variable region of the Ab4 antibody, and a substitution of alanine for aspartic acid as an amino acid residue at position 93 of SEQ ID NO. 5 which is the light-chain variable region. This antibody may include a heavy-chain variable region containing a heavy chain CDR1 of SEQ ID NO. 2; a heavy chain CDR2 of SEQ ID NO. 9; and a heavy chain CDR3 of SEQ ID NO. 10 and a light chain CDR1 of SEQ ID NO. 6; a light chain CDR2 of SEQ ID NO. 7; and a light chain CDR3 of SEQ ID NO. 11.

Further, the antibody specifically binding to L1CAM of the present invention may further include one or more mutations selected from the group consisting of a substitution of isoleucine for valine at position 75 of the light-chain variable region and a substitution of alanine for glycine at position 84 of the light-chain variable region of the frame work region, in addition to the three amino acid residues at CDRs of the heavy-chain variable region of SEQ ID NO. 1 and the light-chain variable region of SEQ ID NO. 5. The valine at position 75 and the glycine at position 84 of the light-chain variable region are amino acid residues positioned in FR3 of the antibody. When the amino acid residues are replaced by isoleucine and alanine, respectively, antigen binding capacity to L1CAM protein may be further improved. FR3 prepared by replacement of both two residues by isoleucine and alanine has an amino acid sequence of SEQ ID NO. 33.

Preferably, the antibody specifically binding to L1CAM which includes a heavy-chain variable region of SEQ ID NO. 1 and a light-chain variable region of SEQ ID NO. 5 may be an antibody having a substitution of phenylalanine for valine as an amino acid residue at position 50 of the heavy-chain variable region of SEQ ID NO. 1 and a substitution of alanine for histidine as an amino acid residue at position 101 of the heavy-chain variable region of SEQ ID NO. 1, and a substitution of alanine for aspartic acid as an amino acid residue at position 93 of the light-chain variable region of SEQ ID NO. 5, and by additional substitution of isoleucine for valine as an amino acid residue at position 75 of the light-chain variable region of SEQ ID NO. 5 and a substitution of alanine for glycine as an amino acid residue at position 84 of the light-chain variable region.

The antibody may include a heavy-chain variable region containing a heavy chain CDR1 of SEQ ID NO. 2; a heavy chain CDR2 of SEQ ID NO. 9; and a heavy chain CDR3 of SEQ ID NO. 10 and a light chain CDR1 of SEQ ID NO. 6; a light chain CDR2 of SEQ ID NO. 7; and a light chain CDR3 of SEQ ID NO. 11, and the heavy chain framework region (FR) thereof may include a heavy-chain variable region containing a heavy chain FR1 of SEQ ID NO. 22; a heavy chain FR2 of SEQ ID NO. 23; a heavy chain FR3 of SEQ ID NO. 24; and a heavy chain FR4 of SEQ ID NO. 25, and a light chain FR1 of SEQ ID NO. 28; a light chain FR2 of SEQ ID NO. 29; a light chain FR3 of SEQ ID NO. 30; and a light chain FR4 of SEQ ID NO. 31, or a heavy-chain variable region containing a heavy chain FR1 of SEQ ID NO. 22; a heavy chain FR2 of SEQ ID NO. 23; a heavy chain FR3 of SEQ ID NO. 24; and a heavy chain FR4 of SEQ ID NO. 25, and a light chain FR1 of SEQ ID NO. 28; a light chain FR2 of SEQ ID NO. 29; a light chain FR3 of SEQ ID NO. 33; and a light chain FR4 of SEQ ID NO. 31, and for example, the antibody may include a heavy-chain variable region of SEQ ID NO. 12 and a light-chain variable region of SEQ ID NO. 13.

In one embodiment of the present invention, the antibody including the heavy-chain variable region of SEQ ID NO. 12 and the light-chain variable region of SEQ ID NO. 13 was designated as 'Ab4M'. This Ab4M antibody provides affinity for human and mouse L1CAM. In this regard, the affinity ($K_D$ value) of Ab4M for human L1CAM was $2.9 \times 10^{-9}$ M and its affinity ($K_D$ value) for mouse L1CAM was $2.2 \times 10^{-10}$ M, as measured by competitive ELISA, indicating that the Ab4M antibody provides remarkably improved affinity for both human and mouse L1CAM proteins, as compared to the results that the affinity ($K_D$ value) of Ab4 for human L1CAM was $1.3 \times 10^{-7}$ M and its affinity ($K_D$ value) for mouse L1CAM was $1.7 \times 10^{-9}$ M, as measured by competitive ELISA.

Further, the present inventors identified an optimal light chain CDR3 sequence (SEQ ID NO. 15) capable of further improving affinity of the Ab4M antibody, and developed an antibody of which expression and affinity are improved, compared to Ab4M antibody, designated as Ab417.

The antibody of which expression and affinity are further improved, compared to Ab4M antibody may include a heavy-chain variable region containing a heavy chain CDR1 of SEQ ID NO. 2; a heavy chain CDR2 of SEQ ID NO. 9; and a heavy chain CDR3 of SEQ ID NO. 10 and a light chain CDR1 of SEQ ID NO. 6; a light chain CDR2 of SEQ ID NO. 7; and a light chain CDR3 of SEQ ID NO. 15, and the heavy chain framework region (FR) thereof may include a heavy-chain variable region containing a heavy chain FR1 of SEQ ID NO. 22; a heavy chain FR2 of SEQ ID NO. 23; a heavy chain FR3 of SEQ ID NO. 24; and a heavy chain FR4 of SEQ ID NO. 25, and a light chain FR1 of SEQ ID NO. 28; a light chain FR2 of SEQ ID NO. 29; a light chain FR3 of SEQ ID NO. 30; and a light chain FR4 of SEQ ID NO. 31, or a heavy-chain variable region containing a heavy chain FR1 of SEQ ID NO. 22; a heavy chain FR2 of SEQ ID NO. 23; a heavy chain FR3 of SEQ ID NO. 24; and a heavy chain FR4 of SEQ ID NO. 25, and a light chain FR1 of SEQ ID NO. 28; a light chain FR2 of SEQ ID NO. 29; a light chain FR3 of SEQ ID NO. 33; and a light chain FR4 of SEQ ID NO. 31, but is not limited thereto. For example, this antibody may include a heavy-chain variable region of SEQ ID NO. 12 and a light-chain variable region of SEQ ID NO. 14. This antibody provides affinity for human and mouse L1CAM. In this regard, its affinity ($K_D$ value) for human L1CAM was $0.18 \times 10^{-9}$ M and its affinity ($K_D$ value) for mouse L1CAM was 34.8 pM, as measured by SPR. Further, the affinity ($K_D$ value) of Ab417 for human L1CAM was $1.2 \times 10^{-9}$ M and its affinity ($K_D$ value) for mouse L1CAM was $2.1 \times 10^{-10}$ M, as measured by competitive ELISA.

Further, the present inventors identified mutation sites capable of maintaining or improving binding affinity for an antigen thereof and improving productivity or physical properties thereof in the Ab417 antibody showing excellent affinity for human and mouse L1CAM proteins and excellent anti-cancer activity.

Specifically, the mutations sites may include one or more of a substitution of glycine for arginine as an amino acid residue at position 16; a substitution of glutamic acid for aspartic acid as an amino acid residue at position 54; a substitution of alanine for lysine as an amino acid residue at position 76; and a substitution of alanine for proline as an amino acid residue at position 88, based on the heavy-chain variable region of SEQ ID NO. 12; and one or more of a substitution of glutamic acid for isoleucine as an amino acid residue at position 31; a substitution of glutamine for arginine as an amino acid residue at position 37; a substitution of lysine for arginine as an amino acid residue at position 39; and a substitution of glutamine for lysine as an amino acid residue at position 42, based on the light-chain variable region of SEQ ID NO. 14.

The heavy-chain variable region for maintaining or improving binding affinity for an antigen thereof and improving productivity or physical properties thereof in the Ab417 antibody may be preferably a heavy-chain variable region (SEQ ID NO. 20) prepared by a substitution of glycine for arginine as an amino acid residue at position 16, a substitution of alanine for lysine as an amino acid residue at position 76, and a substitution of alanine for proline as an amino acid residue at position 88, based on the heavy-chain variable region of SEQ ID NO. 12; or a heavy-chain variable region (SEQ ID NO. 18) having a substitution of glycine for arginine as an amino acid residue at position 16, a substitution of alanine for lysine as an amino acid residue at position 76, a substitution of alanine for proline as an amino acid residue at position 88, and a substitution of glutamic acid for aspartic acid as an amino acid residue at position 54, based on the heavy-chain variable region of SEQ ID NO. 12. Among the residues capable of improving productivity and physical properties, the amino acid arginine at position 16 is positioned in heavy chain FR1, which may be represented by an FR1 sequence (SEQ ID NO. 26) having a substitution of glycine for arginine as an amino acid residue at position 16 of SEQ ID NO. 22. Further, the amino acid lysine at position 76 and the amino acid proline at position 88 are positioned in FR3, which may be represented by a sequence (SEQ ID NO. 27) having a substitution of alanine for lysine as an amino acid residue at position 10 and a substitution of alanine for proline as an amino acid residue at position 22 of FR3 of SEQ ID NO. 24. In the present invention, the heavy-chain variable region of SEQ ID NO. 20 was designated as 'H5', and the heavy-chain variable region of SEQ ID NO. 18 was designated as 'H6'.

Further, the light-chain variable region for maintaining or improving binding affinity for an antigen thereof and improving productivity or physical properties thereof in the Ab417 antibody may be preferably a light-chain variable region (SEQ ID NO. 19) having a substitution of serine for isoleucine as an amino acid residue at position 31, a light-chain variable region (SEQ ID NO. 21) having a substitution of glutamine for arginine as an amino acid residue at position 37, a substitution of lysine for arginine as an amino acid residue at position 39, and a substitution of glutamine for lysine as an amino acid residue at position 42, or a light-chain variable region having a substitution of serine for isoleucine as an amino acid residue at position 31, a substitution of glutamine for arginine as an amino acid residue at position 37, a substitution of lysine for arginine as an amino acid residue at position 39, and a substitution of glutamine for lysine as an amino acid residue at position 42, based on the light-chain variable region of SEQ ID NO. 14 (SEQ ID NO. 34). Here, since the amino acid isoleucine at position 31 is positioned in LCDR1, this substitution corresponds to a substitution of serine for isoleucine as an amino acid at position 8 of LCDR1 of SEQ ID NO. 6, and it has an amino acid sequence of SEQ ID NO. 17. Further, since the amino acid arginine at position 37, the amino acid arginine at position 39, and the amino acid lysine at position 42 are positioned in light chain FR2, the substitutions correspond to a substitution of glutamine for arginine as an amino acid at position 3, a substitution of lysine for arginine as an amino acid at position 5, and a substitution of glutamine for lysine as an amino acid at position 8 of light chain FR2 of SEQ ID NO. 29, and it has an amino acid sequence of SEQ ID NO. 32.

In the present invention, the light-chain variable region of SEQ ID NO. 19 was designated as 'L2', the light-chain variable region of SEQ ID NO. 21 was designated as 'L1', and the light-chain variable region of SEQ ID NO. 34 was designated as 'L6'.

The antibody that is prepared by mutation of the Ab417 antibody to improve productivity and physical properties may be preferably an antibody that includes a heavy-chain variable region containing a heavy chain CDR1 represented by SEQ ID NO. 2, a heavy chain CDR2 represented by SEQ ID NO. 16, and a heavy chain CDR3 represented by SEQ ID NO. 10, and a light-chain variable region containing a light chain CDR1 represented by SEQ ID NO. 17, a light chain CDR2 represented by SEQ ID NO. 7, and a light chain CDR3 represented by SEQ ID NO. 15, and more preferably, an antibody that includes a heavy-chain variable region (H6) of SEQ ID NO. 18 and a light-chain variable region (L2) of SEQ ID NO. 19. In an embodiment of the present invention, the antibody including the heavy-chain variable region of SEQ ID NO. 18 and the light-chain variable region of SEQ ID NO. 19 was designated as 'Ab417-H6L2'.

The antibody that is prepared by mutation of the Ab417 antibody to improve productivity and physical properties may be preferably an antibody that includes a heavy-chain variable region containing a heavy chain CDR1 represented by SEQ ID NO. 2, a heavy chain CDR2 represented by SEQ ID NO. 16, and a heavy chain CDR3 represented by SEQ ID NO. 10, and a light-chain variable region containing a light chain CDR1 represented by SEQ ID NO. 17, a light chain CDR2 represented by SEQ ID NO. 7, and a light chain CDR3 represented by SEQ ID NO. 15, and more preferably, an antibody that includes a heavy-chain variable region (H6) of SEQ ID NO. 18 and a light-chain variable region (L6) of SEQ ID NO. 34. This antibody was designated as 'Ab417-H6L6'.

The antibody that is prepared by mutation of the Ab417 antibody to improve productivity and physical properties may be preferably an antibody that includes a heavy-chain variable region containing a heavy chain CDR1 represented by SEQ ID NO. 2, a heavy chain CDR2 represented by SEQ ID NO. 9, and a heavy chain CDR3 represented by SEQ ID NO. 10, and a light-chain variable region containing a light chain CDR1 represented by SEQ ID NO. 6, a light chain CDR2 represented by SEQ ID NO. 7, and a light chain CDR3 represented by SEQ ID NO. 15, and more preferably, an antibody that includes a heavy-chain variable region of SEQ ID NO. 20 and a light-chain variable region of SEQ ID NO. 21.

The antibody that is prepared by mutation of the Ab417 antibody to improve productivity and physical properties may be preferably an antibody that includes a heavy-chain variable region containing a heavy chain CDR1 represented by SEQ ID NO. 2, a heavy chain CDR2 represented by SEQ ID NO. 9, and a heavy chain CDR3 represented by SEQ ID NO. 10, and a light-chain variable region containing a light chain CDR1 represented by SEQ ID NO. 17, a light chain CDR2 represented by SEQ ID NO. 7, and a light chain CDR3 represented by SEQ ID NO. 15, and more preferably, an antibody that includes a heavy-chain variable region (H5) of SEQ ID NO. 20 and a light-chain variable region (L2) of SEQ ID NO. 19. This antibody was designated as 'Ab417-H5L2'.

The various L1CAM-binding antibodies of the present invention provide high affinity for human and mouse L1CAM, compared to the existing antibody, thereby specifically binding to L1CAM with high affinity. Therefore, the antibody of the present invention may be used in any application employing L1CAM antigen recognition.

In an embodiment of the present invention, various substitutions of the amino acids of the human and mouse L1CAM-binding antibody, Ab4 were performed to found that substitution (H97A) of alanine for histidine as an amino acid residue at position 97 of the heavy-chain variable region (SEQ ID NO. 1) according to kabat numbering (amino acid residue at position 101 of SEQ ID NO. 1), substitution (V50F) of phenylalanine for valine as an amino acid residue at position 50 of the heavy-chain variable region, and substitution (D93A) of alanine for aspartic acid as an amino acid residue at position 93 of the light-chain variable region (SEQ ID NO. 5) are important in the improvement of affinity for L1CAM (FIG. 1). In particular, the Ab4M antibody, which was prepared by additional substitution of isoleucine for valine as an amino acid residue at position 75 of the light-chain variable region and a substitution of alanine for glycine as an amino acid residue at position 84 of the light-chain variable region in addition to substitutions of H97A, V50F, D93A, was found to have specificity for both human and mouse L1CAM, and about 45 times higher binding affinity than the existing antibody Ab4 (FIGS. 2 to 3). Further, as this antibody recognizes L1CAM protein, it exhibits toxicity to cancer cells via ADCC and anti-cancer effects without body-weight loss (FIGS. 4 to 5). To further improve affinity of the Ab4M antibody with high affinity, additional mutations in the light chain CDR3 of the Ab4M antibody were carried out to develop the Ab417 antibody of the present invention which has more improved affinity than the Ab4M antibody. This antibody showed two times higher human L1CAM affinity than the Ab4M antibody, and also it was highly expressed (FIGS. 6 to 7). Furthermore, it was found that the Ab417 antibody recognizes L1CAM protein, thereby showing toxicity against cancer cells via ADCC and anti-cancer effects without body-weight loss (FIG. 8). To improve physical properties or/and productivity of Ab417, the heavy chain and light-chain variable regions of Ab417 were modified to prepare a heavy chain variable region (H6) having R16G, K76A and P88A; a light chain variable region (L2) having I31A; and a light chain variable region (L6) having R37Q, R39K and K42Q. The productivity and physical properties of Ab417-H6L2 and Ab417-H6L6 were examined. As a result, Ab417-H6L2 had antigen-binding affinity for L1CAM being similar to Ab417 and showed excellent productivity and physical properties. Ab417-H6L6 also had antigen-binding affinity being similar to Ab417 and showed improved physical properties (Example 6). These results suggest that the antibody of the present invention may be effectively used in the fields requiring L1CAM recognition, for example, diagnosis and treatment of diseases having L1CAM overexpression.

In another aspect, the present invention provides a method for preparing the antibody.

The antibody of the present invention may be easily prepared using a well-known technique of preparing antibodies. For example, a preparation method of monoclonal antibody may be carried out by preparing hybridoma using B lymphocyte derived from immunized animals (Koeher and Milstein, 1976, Nature, 256:495), or by using phage display technology, but is not limited thereto. A preparation method of polyclonal antibody may be easily carried out by using a known technique of preparing antibodies.

Antibody library using phage display technology is a method in which antibody genes are directly obtained from B lymphocyte without preparing hybridoma to express antibodies on the phage surface. The use of phage display technology enables conventional difficulties associated with formation of monoclonal antibodies by B-cell immortalization to be avoided. A general phage display technology includes: 1) incorporating an oligonucleotide having a random sequence into the gene site which corresponds to the N-terminal of phage coat protein pIII (or pIV); 2) expressing fused protein of a part of natural coat protein and polypeptide encoded by the oligonucleotide with random sequence; 3) treating an acceptor bound to the polypeptide encoded by the oligonucleotide; 4) eluting peptide-phage particles bound to the acceptor using a molecule having a low pH or bonding competitiveness; 5) amplifying the eluted phage in host cells by a panning process; 6) repeating the previous process to obtain a desired level; and 7) identifying a sequence of active peptide from DNA sequences of phage clones selected by panning.

Preferably, the preparation of the monoclonal antibody of the present invention may be implemented using a phage display technology. The preparation method of the present invention may be stepwise conducted by those skilled in the art with reference to the known phage display technology, for example, Barbas et al. (METHODS: A Companion to Methods in Enzymology 2: 119, 1991 and J. Virol. 2001 July; 75(14):6692-9), and Winter et al. (Ann. Rev. Immunol. 12:433, 1994). The phage useful for constructing an antibody library may be a filamentous phage which may be exemplified by fd, M13, f1, If1, Ike, Zj/Z, Ff, Xf, Pf1 or Pf3, but is not limited thereto. Examples of the vector that may be used to display exogenous genes on the surface of the filamentous phage include phage vectors such as fUSE5, fAFF1, fd-CAT1 and fdtetDOG, or phagemid vectors such as pHEN1, pComb3, pComb8 or pSEX, but are not limited thereto. A helper phage, which is used to supply a wild-type version of the coat proteins that are required for the successful reinfection of recombinant phage for amplification, may be exemplified by M13K07 or VSCM13, but is not limited thereto.

Further, a yeast display technology is to express proteins on the surface of yeast cells. Since yeast has a eukaryotic protein expression system, post-translational modification occurs in the proteins expressed by this technology, thereby obtaining recombinant proteins closer to human proteins, compared to use of phage or ribosome display technology. Further, the yeast display technology has advantages that clone selection and quantitative analysis can be performed at the same time because clones are selected by FACS (fluorescence-activated cell sorting). In general, a yeast display technology of scFv antibody includes the steps of: 1) inserting a scFv library and a tag sequence to the C-terminus of the yeast cell wall protein Aga2p via a short amino acid linker; 2) linking Aga2 and scFv antibody gene to the yeast cell wall protein Aga1 via disulfide bonds to express the gene on the yeast cell surface; 3) binding an antigen to the scFv antibody library expressed on the yeast surface; 4) treating fluorescence-conjugated secondary antibody which is able to specifically recognize the antigen and the tag; 5)

selecting yeast cells that express the antigen-specific scFv antibody by FACS; and 6) obtaining DNA sequence information of the clones selected by FACS so as to determine an antibody variable region sequence having high antigen binding capacity.

A polynucleotide encoding the hybridoma-derived monoclonal antibody or phage display clone according to the present invention may be readily isolated and sequenced using a typical process. For example, oligonucleotide primers which are designed to specifically amplify heavy- and light-chain coding regions from a hybridoma or phage template DNA may be employed. Once the polynucleotide is isolated, it may be inserted into an expression vector which may be then introduced into a host cell. The resulting host cell (i.e., transformant) can produce the monoclonal antibody of interest. Accordingly, the preparation method of the human monoclonal antibody of the present invention may comprise amplifying a polynucleotide coding for the human monoclonal antibody in the expression vector carrying the polynucleotide coding for the human monoclonal antibody, but is not limited thereto.

In still another aspect, the present invention provides a polynucleotide encoding the antibody, an expression vector including the polynucleotide, and a transformant introduced with the vector.

The antibody is the same as described above.

The expression vector including the polynucleotide encoding the antibody provided in the present invention may include, but is not limited to, a vector that allows the replication and/or expression of the polynucleotide in eukaryotic or prokaryotic cells such as mammalian cells (e.g., humans, monkeys, rabbits, rats, hamsters, mice, etc.), plant cells, yeast cells, insect cells and bacterial cells (e.g., *E. coli*). Preferably, the vector may be a vector that is operably linked to a suitable promoter so as to induce the expression of the polynucleotide in the host cell, and includes at least one selection marker. For example, the polynucleotide may be introduced into a phage, a plasmid, a cosmid, a mini-chromosome, a virus, or a retroviral vector.

The expression vector including the polynucleotide encoding the antibody may be an expression vector including respective polynucleotides encoding the heavy chain or the light chain of the antibody, respectively, or an expression vector including both the polynucleotides encoding the heavy chain and the light chain of the antibody.

Examples of the transformant introduced with the expression vector provided in the present invention may include, but are not limited to, bacterial cells such as *E. coli, streptomyces, Salmonella typhimurium*; yeast cells; fungi such as *Pichia pastoria*; insect cells such as *drosophila, spodoptera* Sf9; animal cells such as CHO (Chinese hamster ovary cells), SP2/0 (mouse myeloma), human lymphoblastoid, COS, NSO (mouse myeloma), 293T, Bowes melanoma cells, HT-1080, BHK (baby hamster kidney cells), HEK (human embryonic kidney cells), and PERC.6 (human retina cell); and plant cells which are transformed by introduction of the expression vector.

As used herein, the term "introduction" means the delivery of the vector including the polynucleotide encoding the antibody into host cells. The introduction may be carried out using various methods well known in the art, including calcium phosphate-DNA co-precipitation, DEAE-dextran-mediated transfection, polybrene-mediated transfection, electroporation, microinjection, liposome fusion, lipofectamine transfection, and protoplast fusion. Transduction refers to a process whereby a desired material is transferred to cells via viral particles on the basis of infection. In addition, the delivery of a vector into host cells may be achieved by gene bombardment. In the present invention, introduction may be used interchangeably with transformation.

In still another aspect, the present invention provides an antibody-drug conjugate by binding a drug to the antibody.

The antibody is the same as described above.

As used herein, the term "antibody-drug conjugate" means a material which is prepared by conjugating a drug to the antibody using target specificity, no toxicity during circulation in blood, and pharmacokinetic advantage of the antibody. Generally, this antibody-drug conjugate includes three components of monoclonal antibody-linker-drug, and this conjugate may increase therapeutic effects by delivering a drug to a cell targeted by the antibody, in particular, a cancer cell.

As used herein, the term "drug" refers to a material which is directly or indirectly conjugated to the antibody so as to bring about treatment of diseases targeted by the antibody. The drug capable of binding to the antibody includes radionuclides, drugs, lymphokines, toxins and bispecific antibodies. Examples of the radionuclide include $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, $^{186}$Re, but are not limited thereto. Examples of the drug or toxin include etoposide, teniposide, adriamycin, daunomycin, carminomycin, aminopterin, dactinomycin, mitomycin, cis-platinum and cis-platinum analogues, bleomycins, esperamicins, 5-fluorouracil, melphalan, and other nitrogen mustards, but the drug or toxin capable of binding to the antibody of the present invention is not limited to these examples.

The antibody-drug conjugate may be prepared by various methods of preparing antibody-drug conjugates, which are known in the art.

In still another aspect, the present invention provides a composition including the antibody. The antibody is the same as described above. The composition may be used for preventing or treating cancer or for diagnosing cancer.

In still another aspect, the present invention provides a pharmaceutical composition for preventing or treating cancer, including the antibody.

Since the antibody binds to L1CAM protein with high affinity, the L1CAM protein being known to be overexpressed in cancers and to play an important role in growth and metastasis of cancer, it brings out inhibition, neutralization or cytotoxicity of L1CAM protein, leading to prevention or treatment of diseases having L1CAM overexpression. The antibody is the same as described above.

As used herein, the term "cancer" is not particularly limited as long as it is preventable or treatable with the antibody of the present invention. Examples of the cancer may include cholangiocarcinoma, esophageal cancer, stomach cancer, large intestine cancer, rectal cancer, oral cancer, pharynx cancer, larynx cancer, lung cancer, colon cancer, breast cancer, uterine cervical cancer, endometrial cancer, ovarian cancer, prostate cancer, testis cancer, bladder cancer, renal cancer, liver cancer, pancreatic cancer, bone cancer, connective tissue cancer, skin cancer, brain cancer, thyroid cancer, leukemia, Hodgkin's disease, lymphoma and multiple myeloid blood cancer. As used herein, the term "prevention" is intended to refer to any action resulting in the suppression or delay of the onset of cancer owing to the administration of the composition, and the term "treatment" is intended to refer to any action resulting in an improvement in the symptoms of cancer or the beneficial alteration of the symptoms owing to the administration of the composition.

The pharmaceutical composition may further include a pharmaceutically acceptable carrier.

As used herein, the term "pharmaceutically acceptable carrier" refers to a carrier or diluent that does not cause significant irritation to an organism and does not abrogate the biological activity and properties of the administered compound. For liquid formulation, the pharmaceutically acceptable carriers should be sterilized and suitable to living bodies. For example, it may include a saline solution, sterilized water, a Ringer's solution, a buffered saline solution, an albumin injection solution, a dextrose solution, a malto dextrin solution, glycerol, ethanol, or the mixture of one or more of the above ingredients. If necessary, other common additives can be added, such as antioxidants, buffers, bacteriostatic agents or the like. Also, diluting agents, dispersing agents, surfactants, binders or lubricants may be further added to formulate the composition to injection formulations such as an aqueous solution, a suspension, and an emulsion, pills, capsules, granules, or tablets.

The pharmaceutical composition may be in various oral or non-oral dosage forms. The pharmaceutical composition may be formulated in combination with a diluent or excipient such as a filler, a thickener, a binder, a wetting agent, a disintegrant, a surfactant, etc. Solid preparations intended for oral administration may be in the form of tablets, pills, powders, granules, capsules or the like. In regards to these solid agents, the compound of the present invention is formulated in combination with at least one excipient such as starch, calcium carbonate, sucrose, lactose, or gelatin. In addition to a simple excipient, a lubricant such as magnesium stearate, talc, etc. may be used. Among liquid preparations intended for oral administration are suspensions, solutions for internal use, emulsion, syrups or the like. In addition to a simple diluent such as water or liquid paraffin, various excipients, for example, wetting agents, sweeteners, aromatics, preservatives or the like may be contained in the liquid preparations. Also, the pharmaceutical composition of the present invention may be in a parenteral dosage form such as sterile aqueous solutions, non-aqueous solvents, suspensions, emulsions, lyophilized preparations, suppositories. Propylene glycol, polyethylene glycol, vegetable oils such as olive oil, and injectable esters such as ethyl oleate may be used for the non-aqueous solvents and suspensions. The base materials of suppositories include Witepsol, macrogol, Tween 61, cacao butter, laurin butter, and glycerogelatin.

The pharmaceutical composition may have any one formulation selected from the group consisting of tablets, pills, powders, granules, capsules, suspensions, solutions for internal use, emulsion, syrups, sterile aqueous solutions, non-aqueous solvents, suspensions, emulsions, lyophilized preparations, and suppositories.

The composition of the present invention is administered in a pharmaceutically effective amount.

As used herein, the term "pharmaceutically effective amount" refers to an amount sufficient for treating disease in a reasonable ratio of advantage/risk, which can be applicable to medical treatment. The level of the effective dosage can be determined according to the kind and severity, age, gender of a subject, the type of cancer, drug activity, sensitivity to the drug, the time of administration, the route of administration, the rate of excretion, treatment duration, or elements including drugs that are concurrently administered, or other elements well-known in the medical field. The composition the present invention may be administered singly or in combination with other therapeutic agents, or may be also administered with conventional therapeutic agents in a sequential or simultaneous manner. Also, the composition may be administered in a single dose or may be divided into multiple doses. It is important to administer the composition in the minimum amount that can exhibit the maximum effect without causing side effects, in view of all the above-described factors, and it can be easily determined by those skilled in the art.

In an embodiment of the present invention, Ab4M and Ab417 as representative antibody mutants of the Ab4 antibody were found to effectively inhibit cancer growth without body-weight loss, thereby being used for the prevention and treatment of cancer (FIGS. 4, 7, and 11).

In still another aspect, the present invention provides a method for treating cancer using the antibody.

The antibody and cancer are the same as described above.

The method for treating cancer may be a method for treating cancer comprising administering the pharmaceutical composition including the antibody and the pharmaceutically acceptable carrier to a subject having cancer or suspected of having cancer. The pharmaceutically acceptable carrier is as described above. The method for treating cancer may be preferably a method for treating cancer comprising administering the composition including the antibody to a subject having cancer.

The subject may be mammals, such as cow, pig, sheep, chicken, dog, human, etc., and birds, and it may include any subject, of which cancer can be treated by administration of the composition of the present invention, without limitation.

The composition may be administered in single or multiple doses in a pharmaceutically effective amount. In this regard, the composition may be administered in a form of solutions, powders, aerosols, capsules, enteric-coated tablets or capsules or suppositories. Administration modes include intraperitoneally, intravenously, intramuscularly, subcutaneously, intradermally, orally, topically, intranasally, intrapulmonarily and intrarectally, but are not limited thereto. However, since peptides are digested upon oral administration, active ingredients of a composition for oral administration should be coated or formulated for protection against degradation in the stomach. In addition, the pharmaceutical composition may be administered using a certain apparatus capable of transporting the active ingredients into a target cell.

In still another aspect, the present invention provides a method for providing information for cancer diagnosis, comprising detecting antigen-antibody reaction between L1CAM protein and the antibody in a biological sample separated from a subject suspected of having cancer. This method may be also a method for diagnosing cancer.

The antibody, cancer, subject, and L1CAM protein are the same as described above. L1CAM protein is known to be overexpressed in various cancers, and thus the antibody of the present invention may be effectively used for diagnosis of cancer, in which L1CAM protein is overexpressed.

In the method for providing information for cancer diagnosis, L1CAM protein may be detected by reacting the L1CAM-specific human monoclonal antibody of the present invention with a biological sample separated from a subject suspected of having cancer, and then detecting formation of an antigen-antibody complex. Consequently, information for cancer diagnosis may be provided.

In detail, the method may be a method for providing information for cancer diagnosis or a method for diagnosing cancer, comprising (a) treating a biological sample separated from a subject suspected of having cancer with the antibody so as to detect L1CAM protein by antigen-antibody reaction; (b) comparing the level of L1CAM protein detected in (a) with that of a control group, and determining the subject as a cancer patient when the level of L1CAM protein is higher than that of the control group.

As used herein, the term "biological sample" may be tissues, cells, whole blood, serum, plasmic fluid, autoptical samples of tissue (brain, skin, lymph node, spinal cord), supernatant of cell culture, disruptive eukaryotic cells, bacterial expression systems, etc., but is not limited thereto. Existence of L1CAM protein or cancer may be detected by reacting a manipulated or non-manipulated biological sample with the antibody of the present invention.

As used herein, the term "antigen-antibody complex" refers to a combination material of L1CAM protein antigen in the sample and the monoclonal antibody recognizing the antigen of the present invention. Formation of such antigen-antibody complex may be detected by any method selected from the group consisting of a colormetric method, an electrochemical method, a fluorimetric method, luminometry, a particle counting method, visual assessment and a scintillation counting method. However, the method is not limited to the above examples and has a variety of applications.

Various labels may be used for detecting an antigen-antibody complex in the present invention. Specific examples thereof may be selected from the group consisting of enzymes, fluorescent substances, ligands, luminescent substances, microparticles, and radioactive isotopes, but are not limited thereto.

Examples of a detection label include acetylcholine esterase, alkaline phosphatase, β-D-galactosidase, horseradish peroxidase, and β-lactamase as an enzyme; fluorescein, $Eu^{3+}$, $Eu^{3+}$ chelate and cryptate as a fluorescent; biotin-derivatives as a ligand; acridinium ester, isoluminol derivatives as a luminescent; colloidal gold, colored latex as a microparticle; and $^{57}Co$, $^{3}H$, $^{125}I$, $^{125}I$-Bolton Hunter reagent as a radioactive isotopes.

Preferably, the antigen-antibody complex may be detected by using Enzyme-linked immunosorbent assay (ELISA). ELISA techniques include various ELISA methods such as a direct ELISA using a labeled antibody which recognizes an antigen adhered to a support body; an indirect ELISA using a labeled secondary antibody which recognizes a captured antibody of an antigen-antibody complex wherein the antigen adhered to a support body; a direct sandwich ELISA using another labeled antibody which recognizes an antigen of an antigen-antibody complex adhered to a support body; and an indirect sandwich ELISA using another labeled secondary antibody which recognizes an antibody, after reacting with the antibody which recognizes an antigen of an antigen-antibody complex adhered to a support body.

The monoclonal antibody may have a detectable label. Otherwise, the antigen-antibody complex may be detected by treating another antibody which can capture the monoclonal antibody and has a detectable label.

In still another aspect, the present invention provides a composition for diagnosing cancer, including the antibody. The antibody and cancer are the same as described above. The diagnostic composition including the L1CAM protein-specific antibody of the present invention may be used to diagnose a disease which is associated with expression or expression level of L1CAM protein, for example, cancer.

In still another aspect, the present invention provides a kit for diagnosing cancer, including the composition for diagnosing cancer.

The composition and cancer are the same as described above. Further, the kit for diagnosing cancer may further include one or more kinds of a composition, a solution, or an apparatus, which are suitable for the analysis method.

Hereinafter, the present invention will be described in more detail with reference to the following Examples. However, these Examples are for illustrative purposes only, and the invention is not intended to be limited by these Examples.

Example 1. Preparation of Human and Mouse L1CAM-Binding Antibody Ab4

Human and mouse L1CAM-binding antibody Ab4 and a preparation procedure thereof are disclosed in Korean Patent Publication No. 10-2010-0064985, and the preparation procedure thereof is as follows.

(Example 1-1) Preparation of Human L1CAM Antigen and Human L1CAM-Fc Antigen

To prepare human L1CAM antigen, an expression plasmid pJK-dhfr2-L1-monomer (Korean Patent No. 10-0931976) including cDNA encoding an extracellular domain of human L1CAM (amino acid residues at positions 1-1112; hereinafter, referred to as 'human L1CAM') was transfected to HEK293T cells cultured in 10% fetal bovine serum-containing DMEM (Hyclone, USA) medium using lipofectamine 2000 (Invitrogene, USA), and cultured in a 5% $CO_2$ incubator at 37° C. for 4-6 hours. Then, the medium was replaced by serum-free CD293 (Gibco, USA) medium. While the cells were cultured in a 5% $CO_2$ incubator at 37° C., the medium was replaced by a fresh medium every three days. The supernatant was collected three times, and then affinity column chromatography was performed using a column which was prepared by binding A10-A3 antibody to CNBr sepharose (Amersham Phamacia, UK).

To prepare human L1CAM-Fc antigen, a pJK-dhfr2-L1-monomer (Korean Patent No. 10-0931976) containing a sequence of an extracellular domain of human L1CAM (amino acid residues at positions 1-1112) was subjected to polymerase chain reaction (PCR), and the resulting DNA fragment was treated with EcoRI and XhoI, and then cloned into EcoRI and XhoI sites of pJK-dhfr2-Fc, and the prepared plasmid was designated as pJK-dhfr2-hL1Fc.

To express human L1CAM-Fc, pJK-dhfr2-hL1Fc was transfected to HEK293T cells, and then cultured in serum-free medium. The culture supernatant was subjected to affinity chromatography using a protein G column (Upstate, USA) to purify the protein.

(Example 1-2) Preparation of Mouse L1CAM Antigen and Mouse L1CAM-Fc Antigen

To prepare an extracellular domain of mouse L1CAM (hereinafter, referred to as 'mouse L1CAM'), mouse L1CAM was synthesized from a pJK-dhfr-mL1-Fc expression vector, and S1 tag was synthesized from a pJEX2T vector. These two DNA fragments were recombined by PCR. The recombined DNA fragment was cloned into the EcoRI and XhoI sites of the pJK-dhfr-mL1-Fc expression vector, and the resulting mouse L1CAM monomer expression vector was designated as pJK-dhfr-mL1-S1. This plasmid was transfected to HEK293T, and then cultured in serum-free medium. The supernatant was collected and subjected to affinity column chromatography using a column which was prepared by binding KR127 antibody to CNBr sepharose (Amersham Phamacia, UK).

A mouse L1CAM-FC antigen was prepared in the form of a fusion protein of the extracellular domain of mouse L1CAM and Fc region of human IgG1. First, stem cell-type L1CAM cDNA (identical to cancer type) was obtained from the mouse stem cell line SH-J1 through amplification by RT-PCR and cloning and sequencing. To prepare a vector expressing only the extracellular domain of mouse L1CAM, a DNA fragment corresponding to positions 1-1113 in the amino acid sequence of mouse L1CAM was amplified by polymerase chain reaction, and the resulting DNA fragment was isolated and purified using an agarose gel purification kit (iNtRON, Korea), and then cloned to EcoRI and XhoI sites of pJK-dhfr2-Fc which is a vector having Fc of human antibody IgG1. The resulting expression vector DNA was designated as pJK-dhfr-mL1-Fc. This plasmid was transfected to HEK293T cells, and then cultured in serum-free medium. The culture supernatant was subjected to affinity chromatography using a protein G column (Upstate, USA) to purify mouse L1CAM-Fc.

(Example 1-3) Development of Ab4 Antibody Binding to Both Human and Mouse L1CAM

To develop an antibody that recognizes both human L1CAM and mouse L1CAM at the same time, human L1CAM was used as an antigen in the first and second rounds of panning, and mouse L1CAM-Fc in the third round of panning. As a result, positive clones for human L1CAM began to accumulate in the second round of panning, and clones binding to both human L1CAM and mouse L1CAM were obtained in the third round of panning.

After the third round of panning, the eluted phages were diluted $10^4$, $10^5$, and $10^6$ times, and infected to *E. coli* TG1, and plated on a 2YTA solid medium, followed by incubation in a 37° C. incubator overnight. 125 colonies were randomly selected and inoculated in 5 ml of 2YTA liquid medium, respectively and cultured in the 37° C. incubator under shaking until absorbance of each clone at 600 nm reached between 0.7 and 0.8. Next, IPTG was added at a final concentration of 1 mM, and the clones were cultured in the 37° C. incubator under shaking overnight. Then, the culture supernatants were recovered and subjected to indirect ELISA for detecting the antibody that recognizes both human L1CAM and mouse L1CAM.

21 clones binding to human L1CAM and mouse L1CAM were selected and their plasmid DNAs were isolated and digested with a restriction enzyme BstNI (Roche). Grouping of the clones was performed according to the size of fragments, and 6 clones having different fragment sizes (Ab4, Ab6, Ab8, Ab10, Ab12, and Ab13) were selected, followed by sequencing. As a result, it was found that the clones were different from each other.

To analyze binding capacity of the 6 different clones for human L1CAM and mouse L1CAM, indirect ELISA was performed. As a result, Ab4 was found to show the highest antigen binding capacity.

Next, to convert the Fab-type Ab4 into whole IgGγ1, heavy-chain variable region and light-chain variable region were amplified from Ab4 by polymerase chain reaction, and separated on 1.5% agarose gel (Cambrex), followed by purification using a Zymo gel extraction kit (Zymoresearch, USA). Further, to express and produce the antibody in animal cells, leader sequences of heavy chain and light chain were synthesized from pdCMV-dhfrC (Korean Patent Publication No. 10-2010-0064985) by PCR, and separated and purified using 1.5% agarose gel (Cambrex) and the Zymo gel extraction kit (Zymoresearch, USA). Next, the heavy chain leader sequence and heavy-chain variable region, and the light chain leader sequence and light-chain variable region were ligated by recombination PCR, respectively and separated and purified using 1.5% agarose gel (Cambrex) and the Zymo gel extraction kit (Zymoresearch, USA). Thereafter, the heavy chain was digested with the restriction enzymes, EcoRI (Roche) and ApaI (Roche), and the light chain was digested with the restriction enzymes, HindIII (Roche) and BsiWI (Roche), and they were cloned upstream of the heavy chain and the light chain constant regions of pdCMV-dhfrC vector which was digested with the same enzymes and then purified, respectively. The resultant was designated as pdCMV-dhfrC-Ab4. The present inventors deposited the pdCMV-dhfrC-Ab4 expression vector in Genbank of Korea Institute of Bioscience and Biotechnology (Deposit No. KCTC11431BP) on Nov. 21, 2008.

The Ab4 antibody thus obtained is an antibody having high binding capacity for both human and mouse L1CAM, and including a heavy-chain variable region of SEQ ID NO. 1 and a light-chain variable region of SEQ ID NO. 5.

(Example 1-4) Epitope Analysis of Ab4 Antibody

The extracellular domain of L1CAM includes 11 domains of 6 Ig-like domains (Ig1, Ig2, Ig3, Ig4, Ig5, and Ig6) and 5 FnIII domains (Fn1, Fn2, Fn3, Fn4, and Fn5). To examine a domain to which Ab4 bind, human L1CAM-Fc and L1Ig (1-6)Fc, L1Ig(1-5)Fc, L1Ig(1-4)Fc, L1Ig(1-3)Fc, and L1Fn (1-5)Fc proteins which are L1CAM-deleted mutants described in Korean Patent Application No. 10-2006-0107428 were subjected to 8% SDS-PAGE (polyacrylamide gel electrophoresis), and transferred to a PVDF membrane (Millipore) for Western blotting. In this regard, Ab4 antibody was used as a primary antibody, and anti-hIgG(Fc)-HRP (Pierce, 1/5000) was used as a secondary antibody, and an ECL reagent (Amersham Biosciences) was used for detection. As a result, the Ab4 antibody bound to L1Fc, L1Ig(1-6)Fc, and L1Ig(1-5)Fc, but did not bind to L1Ig(1-4)Fc, L1Ig(1-3)Fc, and L1Fn(1-5)Fc. These results indicate that Ab4 binds to the fifth immunoglobulin domain, Ig5 of L1CAM.

Example 2. Improvement of Binding Affinity of Ab4 Antibody

To improve human L1CAM-binding affinity of the Ab4 antibody prepared in Example 1, effects of the respective amino acids constituting the variable region of the Ab4 antibody on the binding capacity of Ab4 antibody were examined. To this end, respective amino acids constituting HCDR1 (SEQ ID NO. 2), HCDR2 (SEQ ID NO. 3), HCDR3 (SEQ ID NO. 4) of the heavy-chain variable region (hereinafter, referred to as 'VH', SEQ ID NO. 1) and LCDR3 (SEQ ID NO. 8) of the light-chain variable region (hereinafter, referred to as SEQ ID NO. 5) of Ab4 antibody were replaced by alanine, and then binding capacities of respective mutants for human L1CAM and mouse L1CAM were compared with that of the existing Ab4 antibody by ELISA as follows.

(Example 2-1) Preparation of Alanine Substitution Mutant of HCDRs and Analysis of Antigen Binding Capacity Primers were prepared to replace the respective amino acid residues constituting HCDR of Ab4 antibody with alanine by polymerase chain reaction, and reaction products were electrophoresed on a 1.5% agarose gel. Bands containing DNAs were cut out and purified using the Zymo gel extraction kit (Zymoresearch). Both ends of the purified DNAs were digested with restriction enzymes EcoRI and ApaI (Roche), and DNA of the pdCMV-dhfrC-Ab4 vector (Accession No. KCTC11431BP), into which the DNA fragments were inserted, was also digested with the same restriction enzymes. Two DNA fragments were ligated using DNA T4 ligase (TaKaRa), and the plasmid DNAs thus prepared were transformed into *E. coli* DH5α for amplification.

The expression vectors of respective mutants were obtained in a large amount, and transfected to human embryonic kidney HEK293T cells using Lipofectamine 2000 (invitrogen), followed by culture. The transfected cells produce and secrete whole antibodies out of the cells, and the culture supernatants were collected and subjected to indirect ELISA as follows. 96-well plates (MaxiSorp, Nunc) were coated using the purified extracellular domain of human L1CAM (hereinafter, referred to as 'human L1CAM') and the extracellular domain of purified mouse L1CAM (hereinafter, referred to as 'mouse L1CAM') as antigens, which were diluted in a buffer solution (15 mM $Na_2CO_3$, 34.84 mM $NaHCO_3$, pH 9.6) at a concentration of 100 ng/well, at 4° C. overnight. Next day, the plate was washed with 0.05% PBS-T buffer solution twice. Difco skim milk (BD) was dissolved in 0.05% PBS-T buffer solution at a concentration of 2%, and 200 μl thereof was added to each well, followed by incubation at 37° C. for 1 hour. Then, the wells were washed with 0.05% PBS-T buffer solution twice. To the plate, 100 μl of the supernatant was added and allowed to react at 37° C. for 1 hour. Then, the wells were washed with 0.05% PBS-T buffer solution three times to remove non-antigen bound antibodies. Goat anti-human IgG(Fc)-HRP (Pierce, 1/5000) that specifically recognizes the Fc region of human antibody was added as a secondary antibody, and allowed to react at 37° C. for 1 hour. Then, the wells were washed with 0.05% PBS-T buffer solution four times to remove the remaining secondary antibodies.

To examine the affinity by color development, 100 μl of a solution (BD OptEIA, BD) containing TMB as a substrate of the HRP enzyme which was covalently linked to the secondary antibody was added to each well, and incubated at room temperature for 5 minutes. Then, 50 μl of 2.5 M $H_2SO_4$ solution was added to each well to terminate the enzymatic reaction. After terminating the reaction, absorbance was measured at 450 nm (VERSAmax microplate reader, Molecular Devices).

As shown in FIG. 1a, the results of indirect ELISA showed that the mutant (hereinafter, referred to as 'H97A') prepared by substituting alanine for histidine at position 97 according to Kabat numbering (amino acid residue at position 101 of SEQ ID NO. 1) in the heavy-chain variable region mutant had increased binding affinity for both human and mouse L1CAM, compared to Ab4 antibody.

(Example 2-2) Preparation of Alanine Substitution Mutant of LCDR3 and Analysis of Antigen Binding Capacity Primers were prepared to replace the respective amino acid residues constituting LCDR3 of Ab4 antibody with alanine by polymerase chain reaction, and reaction products were electrophoresed on a 1.5% agarose gel. Bands containing DNAs were cut out and purified using the Zymo gel extraction kit (Zymoresearch).

Both ends of the purified DNAs were digested with restriction enzymes BsiWI and HindIII (Roche), and DNA of the pdCMV-dhfrC-Ab4 vector, into which the DNA fragments were inserted, was also digested with the same restriction enzymes. Two DNA fragments were ligated using DNA T4 ligase (TaKaRa), and the plasmid DNAs thus prepared were transformed into *E. coli* DH5α for amplification.

Next, the respective mutants was transfected into HEK293T cells in the same manner as in Example 2-1, and whole IgG was recovered from cell culture and used for ELISA.

As shown in FIG. 1b, the mutant (D93A) prepared by substituting alanine for aspartic acid as an amino acid residue at position 93 had increased binding affinity for both human and mouse L1CAM, compared to Ab4 antibody.

(Example 2-3) Preparation of Ab4 Mutant (Ab4M) with Increased Antigen Binding Affinity The amino acid sequences of VH and VK of Ab4 antibody were compared with human antibody VH germline sequence VH3-30 and VL germline sequence VK1-39 from which Ab4 antibody was derived.

Through this procedure, an Ab4-V75I/G84A mutant was prepared by substituting isoleucine (I) and alanine (A) for valine (V) at position 75 and glycine at position 84 of the light-chain variable region FR3 of the existing Ab4 antibody, respectively.

The V50A mutant of Ab4 VH showed lower antigen binding capacity than Ab4 in Example 2-1 (FIG. 1a). To examine amino acid residues capable of increasing antigen binding capacity other than alanine, antibodies including a heavy chain mutant prepared by substituting glutamic acid (V50E), phenylalanine (V50F), arginine (V50R), or threonine threonine (V50T) for valine as an amino acid residue at position 50 of Ab4 VH and a light chain mutant of V75I/G84A sequence were prepared and expressed in the same manner as in Example 2-1, and their antigen binding capacity for human and mouse L1CAM were analyzed. The results are shown in FIG. 1c.

As shown in FIG. 1c, the phenylalanine substitution mutant (V50F) showed remarkably increased antigen binding capacity for both human and mouse L1CAM, unlike other mutants.

Additionally, to further improve the antigen binding capacity of the V50F mutant, D93A mutation of VK and H97A mutation of VH which showed higher antigen binding capacity than Ab4 in Examples 2-1 and 2-2 were included to prepare a mutant having mutations of V75I, G84A, D93A of VK; and V50F, H97A of VH in Ab4 antibody and this mutant was designated as 'Ab4M'. Further, an expression vector having the Ab4M sequence was designated as pdCMV-dhfrC-Ab4M.

Example 3. Characterization of Ab4M Antibody (Example 3-1) Purification of Antibody To compare the antigen binding affinity between Ab4 antibody and Ab4M antibody prepared in Example 2, the antibody was purified. Further, H97A mutant (VH H97A) and V50F/H97A mutant (VH V50F/H97A) of VH and D93A mutant (VK D93A) of VK of Ab4 were also purified. Plasmid DNAs of expression vectors of these antibodies were obtained in a large amount, and expressed in HEK293T cells in the same manner as in Example 2-1, respectively. The cell cultures were centrifuged to collect only supernatants. The collected supernatants were purified by affinity chromatography. The respective supernatants were applied to a column packed with protein A-coupled beads, and Ab4M antibodies were released from protein A using a 0.1 M citric acid solution (pH 3.2), and 1.0 M Tris solution (pH 8.0) was immediately added to the released antibodies for neutralization to maintain the structures of the antibodies. The purified antibodies were subjected to 10% SDS-PAGE and Coomassie staining, so as to confirm that each of the heavy chain and light chains was well expressed and they were assembled as a whole IgG.

(Example 3-2) Measurement of Affinity of Antibody

The affinities of the purified antibodies for human L1CAM were measured by competitive ELISA. Human L1CAM was prepared at a density of $1\times10^{-6}$ M and serially diluted to $1\times10^{-11}$ M using a PBS buffer solution. Respective antibodies were prepared by diluting them in PBS buffer solution at particular concentrations according to their binding capacity. The antigens and antibodies thus diluted were reacted with each other at the same volume ratio, and allowed to react at room temperature for 2 hours.

96-well plates (MaxiSorp, Nunc) were coated using the purified human L1CAM which were diluted in a buffer solution (15 mM $Na_2CO_3$, 34.84 mM $NaHCO_3$, pH 9.6) at a concentration of 100 ng/well, at 4° C. overnight. Next day, the wells were washed with 0.05% PBS-T buffer solution twice. Difco skim milk (BD) was dissolved in 0.05% PBS-T buffer solution at a concentration of 2%, and 200 μl thereof was added to each well, followed by incubation at room temperature for 1 hour. Then, the wells were washed with 0.05% PBS-T buffer solution twice. To the plate, 100 μl it of the antigen/antibody reactant that were reacted for 2 hours was added and allowed to react at room temperature for 1 hour. Then, the wells were washed with 0.05% PBS-T buffer solution three times to remove non-antigen bound antibodies. Goat anti-human IgG(Fc)-HRP (Pierce, 1/5000) that specifically recognizes the Fc region of human antibody was added as a secondary antibody, and allowed to react at room temperature for 1 hour. Then, the wells were washed with 0.05% PBS-T buffer solution four times to remove the remaining secondary antibodies. To examine the affinity by color development, 100 μl of a solution (BD OptEIA, BD) containing TMB as a substrate of the enzyme HRP which was covalently linked to the secondary antibody was added to each well, and incubated at room temperature for 5 minutes. Then, 50 μl of 2.5 M $H_2SO_4$ solution was added to each well to terminate the enzymatic reaction. After terminating the reaction, absorbance was measured at 450 nm (VERSAmax microplate reader, Molecular Devices). The results are shown in FIG. 2.

As shown in FIG. 2a, affinity of Ab4 for human L1CAM was $1.3\times10^{-7}$ M, affinity of VH H97A mutant of Ab4 was $2.9\times10^{-8}$ M, affinity of VH V50F/H97A mutant was $1.8\times10^{-8}$ M, affinity of VK D93A mutant was $3.0\times10^{-8}$ M, and affinity of Ab4M was $2.9\times10^{-9}$ M, suggesting that all the mutants of the Ab4 antibody of the present invention showed excellent affinity, and among them, Ab4M showed about 45 times higher affinity than Ab4 so as to have excellent binding affinity for human L1CAM.

As shown in FIG. 2b, affinities of Ab4 and Ab4M for human L1CAM were measured, and the results showed that their affinity were $1.3\times10^{-7}$ M and $2.9\times10^{-9}$ M respectively and Ab4M showed about 45-folds higher affinity than Ab4.

As shown in FIG. 2c, affinities of Ab4 and Ab4M for mouse L1CAM were measured, and the results showed that their affinity were $1.7\times10^{-9}$ M and $2.2\times10^{-10}$ M respectively and Ab4M showed about 8-folds higher affinity than Ab4, indicating that the Ab4M antibody of the present invention has excellent binding affinity for both human and mouse L1CAM, compared to Ab4 antibody.

(Example 3-3) Analysis of Antigen-Binding Specificity of Ab4M

In order to examine whether the Ab4M antibody selectively binds to human and mouse L1CAM, flow cytometry was performed using various types of cells. In this regard, as a comparative antibody, a chimeric A10-A3 antibody (cA10-A3, Lee et al., EMM 4:293-302, 2012) which binds to human L1CAM but does not bind to mouse L1CAM was used.

As cells expressing no human L1CAM, HEK293T, pancreatic cancer cell line CFPAC (ATCC No. CRL-1918) and CHO-DG44 (ATCC No. PTA-3356) were cultured. As a cell expressing human L1CAM, a cholangiocarcinoma cell line, Choi-CK (Min et al., Clin Cancer Res. 16:3571-80, 2010) was cultured. As a cell overexpressing human L1CAM, a cholangiocarcinoma cell line, SCK-L1 (Min et al., Clin Cancer Res. 16:3571-80, 2010) was cultured. As a cell expressing mouse L1CAM, a melanoma cell line, B16F1 (ATCC No. CRL-6323) was cultured. The cultured cells were harvested using a dissociation buffer (GIBCO, invitrogen), and then resuspended in 1% PBA solution, and placed in ice for 20 minutes. Then, the cells were added to 96-well RV plate (Bioneer) at a density of $2\times10^5$ cells per well.

The purified Ab4M antibody was diluted in PBS solution at a concentration of 10 μg/ml, and 1 μg thereof was added to each well and mixed well with the cells. The plate was placed in ice for 1 hour. In this regard, human IgG antibody (Pierce) as a negative control of Ab4M was treated under the same conditions. As a secondary antibody, 0.5 μg of an antibody (Sigma) which specifically binds to the Fc region of human IgG and is covalently linked with FITC was added to and mixed in each well, and then the plate was wrapped with foil to block light, and allowed to react in ice for 1 hour. A staining reagent PI was treated thereto at a ratio of 1:100 to evaluate cell viability. After all reactions were completed, FITC and PI fluorescent signals were detected in the cells, and the results are shown in FIG. 3.

As shown in FIG. 3, the results showed that Ab4M antibody hardly binds to L1CAM-negative cells, HEK293T, CFPAC and CHO-DG44, and obviously binds to L1CAM-positive cells, SCK-L1 and Choi-CK and B16F1. The results also showed that the control group, cA10-A3 antibody not binding to mouse L1CAM but specifically binding to human L1CAM did not bind to the mouse melanoma cell line B166F1 but bound to the human cell line expressing L1CAM, suggesting that the Ab4M antibody of the present invention is an antibody specifically binding to both human and mouse L1CAM.

(Example 3-4) Analysis of Tumor Growth-Inhibitory Effect of Ab4M

To examine anti-tumor effects of the Ab4M antibody, human-derived cholangiocarcinoma cell line Choi-CK was injected to a nude mouse (BALB/c Slc-nu, SPF, Central. Lab. Animal Inc.) to produce a tumor, and then the tumor of about 100 $mm^3$ was transplanted in nude mice. 1 week later, each 10 mice were injected intravenously (i.v.) with Ab4M antibody or a negative control Synagis antibody at a dose of 10 mg/kg three times a week for 4 weeks, and the tumor size and the body weight of the mice were measured and shown in FIGS. 5a and 5b, respectively.

As shown in FIG. 4, Ab4M antibody very effectively inhibited tumor growth without reducing the body weight of the nude mice.

Example 4. Preparation of Ab417 Antibody

To further improve affinity of Ab4M antibody for L1CAM, the mutants of Vκ (LCDR3 of Ab4M were displayed on the yeast surface in the form of scFv, and then the mutants having higher affinity were separated.

(Example 4-1) Yeast Surface Display of Ab4M scFv scFv of Ab4M was prepared and cloned into a yeast display expression vector (pYD1, invitrogen). VH and VK of Ab4M antibody were synthesized by PCR, and a nucleotide sequence encoding (Gly-Gly-Gly-Gly-Ser)$_3$ in the existing scFv sequence was synthesized, and then these DNA fragments were ligated by recombination PCR to prepare the scFv gene. pYD1 DNA was digested with SphI and EcoRI, and then separated in an agarose gel, and the resulting DNA fragment and the previously synthesized scFv DNA were transformed into a yeast strain EBY100 (Invitrogrn) at a ratio of 1:5, and ligated in the yeast by homologous recombination. The yeast transformant obtained by transformation was inoculated in a medium containing galactose, and cultured for 18 to 36 hours to express Ab4M antibody in the form of scFv.

36 hours after, yeast cells were collected and washed with 0.1% PBA buffer solution prepared by adding 0.1% BSA to 1×PBS buffer solution, and Ig5 domain-hFc fusion protein of human L1CAM which was serially diluted from $1 \times 10^{-5}$ to $1 \times 10^{-8}$ M was added thereto, and allowed to react at room temperature for 1 hour. After reaction, the yeast cells were washed with 0.1% PBA buffer solution, and then reacted with an antigen-specific antibody, goat-anti-human IgG(Fc)-FITC at a ratio of 1:5000 at room temperature for 1 hour. After reaction, the yeast cells were washed with 0.1% PBA buffer solution, and then FITC signals were measured in FACS Calibur (BD) to determine antigen binding capacity of the Ab4M antibody in the form of scFv. The results are shown in FIG. 5a.

As a result, as the antigen concentration was increased, binding of Ab4M antibody of the scFv form was stronger, suggesting that Ab4M antibody is expressed well in the form of scFv, and scFv of Ab4M maintains antigen binding capacity (FIG. 5a).

(Example 4-2) Mutation and Yeast Surface Display of Ab4M scFv Sequence

To obtain Ab4M mutants having high affinity, 7 amino acid residues (T91, H92, A93, T94, R95, Q95a, and Y96) which were expected to directly interact with antigen were selected from amino acids constituting LCDR3, and randomly substituted (T91, H92, A93, T94, R95, Q95a, and Y96). Primers (IDT, USA) for replacing codons encoding 7 amino acids with XYZ (X encodes 38% G, 19% A, 26% T, 17% C; Y encodes 31% G, 34% A, 17% T, 18% C; Z encodes 24% G, 76% C) were synthesized to perform PCR. In this regard, to increase accuracy of PCR, Prime STAR polymerase (TAKARA) was used.

PCR was performed by pre-denaturation of the template DNA at 94° C. for 5 minutes. Next, 25 cycles consisting of denaturation at 94° C. for 30 seconds, annealing of the primers and the template DNA at 55° C. for 30 seconds, and then DNA elongation at 72° C. for 30 seconds were repeated. After 25 cycles, DNA elongation was further allowed at 72° C. for 7 minutes. A DNA fragment obtained by PCR and a yeast display expression vector digested with SphI and EcoRI were transformed into yeast EBY100. The transformed yeast cells were diluted 10, $10^2$, $10^5$, $10^{10}$ times, and plated on a tryptophan-free medium and incubated at 30° C. for 2 days to count the number of colonies formed. Diversity of the library thus obtained was $2 \times 10^9$.

To select mutants having binding affinity for human L1CAM from the library, MACS (magnetic-activated cell sorting) was performed. The transformants were inoculated in a galactose-containing medium and cultured for 18 to 36 hours to display scFv on the yeast surface. Then, the yeast cells were collected and washed with 0.1% PBA buffer solution, and then Ig5-hFc of human L1CAM diluted at $1 \times 10^{-7}$ M was added thereto, and allowed to react at room temperature for 1 hour. After reaction, the yeast cells were washed with 0.1% PBA buffer solution and mixed with antigen-specific Protein G magnetic beads (NEB), and then allowed to react at 4° C. for 1 hour. The reacted mutants showed a magnetic property due to magnetic beads. Therefore, when these mutant were applied to a column (MACS Separation Columns, Miltenyl Biotec) that was fixed in a magnetic support (QuadroMACS™ Separation Unit, Miltenyl Biotec), only the mutants having binding capacity to human L1CAM antigen bound to the column. The column was separated from the support to obtain only the mutants bound. The number of the mutants having binding capacity to human L1CAM was $1.37 \times 10^7$.

To select mutants having higher binding capacity to human L1CAM than Ab4M from these mutants, FACS sorting was performed. Since FACS experiment of Example 3-1 showed that Ab4M scFv had antigen binding capacity until the concentration of human L1CAM was $1 \times 10^{-8}$ M, the concentration of the antigen to be used was determined as $5 \times 10^{-9}$ M. The mutants obtained by MACS were expressed as scFv in the same manner as above, and the yeast cells were collected and bound to the antigens at a concentration of $5 \times 10^{-9}$ M, followed by FITC staining and sorting by FACS Aria (BD). In this regard, to select only the mutants having improved affinity, gate was determined to sort the mutants having the top 0.1% binding affinity from the total mutants. Sorting was performed twice, and from the resulting mutants, 48 mutants having different sequences were finally obtained.

Each of 48 mutants was expressed, and their antigen binding capacity and yeast surface display of scFv were analyzed. Each of 48 yeast clones was expressed and $5 \times 10^6$ yeast cells were collected and washed with 0.1% PBA twice. $1 \times 10^{-8}$ M of Ig5-hFc of human L1CAM as an antigen was added thereto and the cells were suspended well and left at room temperature for 1 hour, and allowed for binding of scFv and antigen. The cells were washed with 0.1% PBA twice. To examine surface display of scFv, V5 tag-specific rabbit antibody (abcam, 1.00 mg/ml) was bound to the yeast, and stained with anti-mouse IgG-Cy5 antibody (abcam, 0.50 mg/ml) which recognizes the antibody.

To examine the antigen binding capacity, Ig5-hFc ($1 \times 10^{-8}$ M) was bound, followed by staining with anti-human IgG (Fc)-FITC (Pierce, mg/ml). They were reacted at 4° C. for 1 hour and then washed with 0.1% PBA three times. After reaction, the yeast cells were collected and suspended in 0.1% PBA, followed by FACS in FACS Calibur (BD). As a result of FACS, the mutant showing expression similar to Ab4M scFv expression but having improved antigen binding capacity was found, which was designated as 'Ab4M-18'.

scFv expression level and antigen binding capacity were compared between Ab4M and Ab4M-18, and shown in FIG. 5b. Specifically, in FIG. 6b, the increasing value on the vertical axis represents higher expression level, and the increasing value on the horizontal axis represents higher antigen binding capacity. That is, since high populations in Up-Right (UR) quadrant may indicate high expression and high antibody binding capacity, and Ab4M-18 scFv showed higher populations in Up-Right (UR) quadrant than Ab4M scFv, suggesting improvement in antibody binding capacity. These results suggest that Ab4M-18 has excellent antibody binding capacity and expression level, compared to Ab4M.

*Example 4-3) Codon Optimization and Increased Expression Level of Ab4M-18 Antibody To increase the expression level of Ab4M-18 antibody in mammalian cells, codons of heavy chain and light chain of Ab4M-18 antibody were optimized for mammalian cells. Based on amino acid sequences of light chain and heavy chain of Ab4M-18, information about nucleotide sequences optimized for mammalian cells were obtained from EnCor Biotechnology Inc. homepage (http://www.encorbio.com/protocols/Codon.htm), and genes of light chain and heavy chain were synthesized by IDT (USA).

Both ends of the codon-optimized gene of the heavy chain constant region were digested with ApaI and NotI, and cloned into ApaI-NotI sites of pdCMV-dhfrC-Ab4M, and both ends of the codon-optimized VH gene were digested with EcoRI and ApaI and cloned into the vector including the codon-optimized heavy chain constant region. Both ends of the codon-optimized gene of light chain constant region were digested with BsiWI and XbaI, and subcloned into BsiWI-XbaI sites of the resulting vector. Both ends of the codon-optimized VK gene were digested with HindIII and BsiWI, and subcloned into HindIII-BsiWI sites of the resulting vector. The resulting expression vector including the codon-optimized heavy chain gene and light chain gene was designated as pdCMV-dhfrC-Ab417.

The final pdCMV-dhfrC-Ab417 vector was transfected to HEK293T cells in the same manner as in Example 2, and then cultured in serum-free medium. Only the supernatant was collected to examine the expression level using human IgG as standard by sandwich ELISA. As a result, about 20% increase in the expression level was observed. IgG expressed from the pdCMV-dhfrC-Ab417 vector was designated as 'Ab417' antibody.

Example 5. Analysis of Affinity, Specificity and Efficacy of Ab417 Antibody (Example 5-1) Production and Purification of Ab417 Antibody A large amount of pdCMV-dhfrC-Ab417 plasmid DNA was isolated and purified using a kit (HiSpeed Plasmid Maxi Kit, QIAGEN). 10 µg of the obtained plasmid DNA and 40 µg of PEI (polyethyleneimine) were diluted with 500 it of 150 mM NaCl (pH 5.4) solution, respectively and then two solutions were mixed with each other and left at room temperature for 15 minutes. This mixture was uniformly sprayed onto HEK293T cells (70 to 80% density) which were cultured at a density of $2\times10^5$ cells/ml in a 100 mm²-plate, and incubated in a 37° C., 5.0% $CO_2$ incubator for 6 hours. After 6 hours, the culture medium was completely removed, and the cells were cultured in 10 ml of serum-free medium. After 3 and 6 days, only the supernatants were collected. Antibodies were purified from the collected supernatant in the same manner as in Example 2. Purity of the purified antibodies was analyzed by Bioanalyzer.

(Example 5-2) Measurement of Affinity of Ab417 Antibody

Affinity of the purified Ab417 antibody for human L1CAM was measured by competitive ELISA in the same manner as in Example 3-2. As shown in FIG. 2b, affinity of the purified Ab417 antibody for human L1CAM was $1.2\times10^{-9}$ M, indicating that its affinity was about 2.4-folds higher than affinity of Ab4M ($2.9\times10^{-9}$ M), and about 92-folds higher than affinity of Ab4 ($1.3\times10^{-7}$ M).

As shown in FIG. 2c, affinity of the Ab417 antibody for mouse L1CAM was $2.1\times10^{-10}$ M, indicating that its affinity was similar to affinity of Ab4M for mouse L1CAM ($2.2\times10^{-10}$ M), and about 8 times higher than affinity of Ab4 ($1.7\times10^{-9}$ M). These results suggest that the Ab417 antibody of the present invention has very excellent binding capacity to both human and mouse L1CAM, compared to the Ab4 antibody.

In addition to the competitive ELISA, SPR (surface plasma resonance) was measured using Octet RED (ForteBio, USA) according to the manufacturer's protocol to determine the affinities of Ab417 antibody and Ab4M antibody for human and mouse L1CAM. The antibodies were diluted with PBS at a concentration of 2 µg/ml, and then human L1CAM was serially diluted with PBS at a concentration of 100, 50, 25, 12.5, 6.25 and 0 nM, and mouse L1CAM was serially diluted with PBS at a concentration of 30, 10, 3.3, 1.1, 0.37, 0.12, 0.04 and 0 nM and each 200 µl thereof was added to opaque 96-well plate to prevent light transmission. AHC (anti-human IgG Fc capture) sensor chip was used to analyze binding kinetics of the antibodies to antigens by examining changes in refractive index which occurs upon association and dissociation of antibody and antigen while transferring the sensor chip to PBS solution, antibody, PBS solution, antigen, and PBS solution in this order. The results are shown in FIG. 6.

As a result, affinity ($K_D$) of Ab417 antibody for human L1CAM was 0.18 nM ($K_{on}=1.27\times10^5$/Ms; $K_{dis}=2.33\times10^{-5}$/s), and affinity ($K_D$) of Ab4M antibody for human L1CAM was 0.33 nM ($K_{on}=1.30\times10^5$/Ms; $K_a=4.30\times10^{-5}$/s). Further, affinity ($K_D$) of Ab417 antibody for mouse L1CAM was 34.8 pM ($K_{on}=2.33\times10^5$/Ms; $K_{dis}=8.10\times10^{-6}$/s), and affinity ($K_D$) of Ab4M antibody for mouse L1CAM was 89.3 pM ($K_{on}=2.49\times10^5$/Ms; $K_{dis}=2.22\times10^{-5}$/s). These results indicate that affinity of Ab417 antibody is about 2 times higher than that of Ab4M.

(Example 5-3) Analysis of Specificity of Ab417 Antibody

Specificity of Ab417 antibody to antigen was analyzed by flow cytometry in the same manner as in Example 3-2, and the results are shown in FIGS. 3a and 3b.

As a result, Ab417 antibody also has specificity to human and mouse L1CAM, similar to Ab4M antibody, indicating that Ab417 antibody can be used as an antibody binding to both human and mouse L1CAM.

(Example 5-4) Analysis of Tumor
Growth-Inhibitory Effect of Ab417

To investigate anti-tumor effect of the Ab417 antibody, cholangiocarcinoma models were prepared as in Example 3-5, and each 10 mice were administered with human IgG Fc (control group, 3.3 mg/ml) or Ab417 antibody (experimental group, 10 mg/kg) three times a week total 9 times to examine anti-tumor effect. The results are shown in FIG. 7.

As shown in FIG. 7a, the group administered with Ab417 antibody of the preset invention showed significant inhibitory effect on tumor growth, compared to the group administered with the negative control human IgG Fc. Further, after completion of the administration, tumors were excised from the nude mouse models and weighed. As a result, the weight of the tumor was about 63% smaller than that of the control group (FIG. 7b). In addition, no body weight loss was observed in the mice during administration and no toxicity by administration of the antibody was observed (FIG. 7c).

Therefore, these results indicate that the antibody of the present invention has high binding capacity to L1CAM, thereby being very effectively used for the prevention and treatment of cancer.

Example 6. Preparation and Characterization of Ab417 Antibody Mutants (Example 6-1) Preparation of Ab417-H6L2 and Ab417-H6L6 Mutants To increase productivity of the Ab417 antibody, physicochemical properties of the variable region of Ab417 antibody were improved by replacement of several amino acid residues of the surface of antibody variable region by other amino acid residues, and improvement of productivity was examined. The substituted amino acid residues and cloning procedure are as follows.

Arginine at position 16, lysine at position 76 and proline at position 88 of VH of Ab417 antibody were replaced by glycine (R16G), alanine (K76A), and alanine (P88A), respectively, and aspartic acid at position 54 in which posttranslational modification may occur was replaced by glutamic acid (D54E). VH DNA containing R16G, D54E, K76A and P88A was synthesized and ligated with human heavy chain constant region (CH) by polymerase chain reaction. This reaction product was electrophoresed in 1.0% agarose gel and then a band containing the synthesized DNA was cut out and purified using a Zymo gel extraction kit. Both ends of the purified heavy chain DNA was digested with restriction enzymes, EcoRI and NotI, and subcloned into the EcoRI-NotI sites of a cloning vector pcDNA™ 3.4 (Life technologies), which was designated as pcDNA™ 3.4-Ab417-H6. The nucleotide sequences of pcDNA™ 3.4-Ab417-H6 that were introduced into $E.$ $coli$ DH5α were analyzed, and substitutions of the above amino acid residue were confirmed.

I31S mutant prepared by substitution of serine for isoleucine at position 31 of Vκ of Ab417 antibody was ligated with light chain constant region (Cκ) by polymerase chain reaction. This reaction product was electrophoresed in 1.0% agarose gel and then a band containing the synthesized DNA was cut out and purified using a Zymo gel extraction kit. Both ends of the purified light chain DNA was digested with restriction enzymes, HindIII and XbaI, and subcloned into the HindIII-XbaI sites of a cloning vector pcDNA™ 3.4, which was designated as pcDNA™ 3.4-Ab417-L2.

To reduce pI value of Ab417, a mutant was prepared by substitution of serine for isoleucine at position (I31S), substitution of glutamine for arginine at position 37 (R37Q), substitution of lysine for arginine at position 39 (R39K), and substitution of glutamine for lysine at position 42 (K42Q) of Vκ of Ab417 antibody, and then ligated with human light chain constant region by polymerase chain reaction. This reaction product was electrophoresed in 1.0% agarose gel and then a band containing the synthesized DNA was cut out and purified using a Zymo gel extraction kit. Both ends of the purified heavy chain DNA was digested with restriction enzymes, HindIII and XbaI, and subcloned into the HindIII-XbaI sites of a cloning vector pcDNA™ 3.4, which was designated as pcDNA™ 3.4-Ab417-L6.

The nucleotide sequences of pcDNA™ 3.4-Ab417-L2 and pcDNA™ 3.4-Ab417-L6 that were introduced into $E.$ $coli$ DH5α were analyzed, and substitutions of the above amino acid residue were confirmed.

(Example 6-2) Analysis of Productivity of Ab417-H6L2 and Ab417-H6L6 Mutants

Productivity of Ab417-H6L2 and Ab417-H6L6 as the Ab417 mutants were compared to that of Ab417. To express the Ab417-H6L2 mutant, pcDNA™ 3.4-Ab417-H6 and pcDNA™ 3.4-Ab417-L2 plasmid DNAs were isolated and purified in a large amount using a PureYield™ Plasmid Maxiprep System (Promega), and co-transfected to HEK293T cells in the same manner as in Example 5-1. To express the Ab417-H6L6 mutant, pcDNA™ 3.4-Ab417-H6 and pcDNA™ 3.4-Ab417-L6 plasmid DNAs were isolated and co-transfected to HEK293T cells. In this regard, to express Ab417 antibody as a control group, pcDNA™ 3.4-Ab417-H and pcDNA™ 3.4-Ab417-L were isolated and co-transfected to HEK293T cells The transfected cells were cultured for 3 days or 6 days, and then supernatants were obtained and antibodies were purified in the same manner as in Example 2. The amounts of the purified antibodies were measured by Nanodrop.

As a result, the productivity of Ab417-H6L6 antibody was not increased, compared to that of Ab417, whereas the productivity of Ab417-H6L2 antibody was increased about 2.5 times, compared to that of Ab417. The purity of the purified antibodies was analyzed using a Bioanalyzer.

(Example 6-3) Analysis of Affinities of Ab417-H6L2 and Ab417-H6L6 Mutants

To compare antigen binding capacities of Ab417-H6L2 and Ab417-H6L6 mutants with that of Ab417, ELISA was performed using human L1CAM as an antigen.

As a result, antigen binding capacities of Ab417-H6L2 and Ab417-H6L6 mutants were similar to that of Ab417.

In conclusion, the Ab417-H6L2 mutant showed higher productivity and lower pI value than Ab417 antibody, and the Ab417-H6L6 mutant showed lower pI value than Ab417 antibody, but showed human L1CAM binding capacity similar to Ab417.

Example 7. Pharmacokinetic (PK) Analysis of Ab417 Antibody (Example 7-1) Antibody Administration Sprague-Dawley rats (male, 9-week old) widely used in pharmacokinetics and safety test of drugs for PK analysis were administered with Ab417 antibody. Total 6 rats were divided into 2 groups of 3 rats each, and single intravenous administration of Ab417 antibody was performed at a dose of 3 and 10 mg/kg. During antibody administration, general symptoms were observed once daily.

(Example 7-2) Collection of Blood and Isolation of Serum from Collected Blood Sample About 500 ml of blood was collected from the jugular vein of each rat using a heparin-treated disposable syringe before administration (blank), and at 1 hr, 6, 12, 24 hrs and 2, 3, 5, 7 and 10 days after administration. The collected blood was centrifuged at 12000 rpm, 4° C. for 3 minutes to isolate serum, which was stored at −80° C. until experiment.

(Example 7-3) Measurement of Serum Antibody Level by Sandwich ELISA

Sandwich ELISA was performed using the prepared serum samples in plates which had been coated with human L1CAM in advance, and the results are shown in the following Table 1. The amount of antibody was calculated using a standard curve, and as a result, it was found that the amount of antibody was reduced over time (FIG. 9).

TABLE 1 concentration of antibody in rat serum (μg/ml)

| time (hr) | 3 mg/kg | | 10 mg/kg | |
| --- | --- | --- | --- | --- |
| | mean | Standard deviation | mean | Standard deviation |
| 0 | 0 | 0 | 0 | 0 |
| 1 | 90 | 6 | 204 | 41 |
| 6 | 47 | 7 | 137 | 35 |
| 12 | 43 | 9 | 115 | 21 |
| 24 | 38 | 4 | 69 | 9 |
| 48 | 19 | 3 | 39 | 6 |
| 72 | 16 | 3 | 30 | 4 |
| 120 | 10 | 1 | 28 | 3 |
| 168 | 5 | 2 | 19 | 2 |
| 240 | 2 | 2 | 13 | 1 |

Pharmacokinetic parameters calculated based on the measured blood concentrations are shown in the following Table 2.

TABLE 2

| Group Dose (mg/kg) | | $AUC_{last}$ (μg · hr/mL) | $C_{max}$ (μg/mL) | $T_{max}$ (hr) | $t_{1/2}$ (hr) | $CL_t$ (mL/hr/kg) | $V_d$ (mL/kg) | MRT (hr) |
| --- | --- | --- | --- | --- | --- | --- | --- | --- |
| G1 | Mean | 3484.50 | 90.00 | 1.00 | 65.05 | 0.81 | 73.73 | 60.11 |
| 3 | S.D. | 674.44 | 6.08 | 0.00 | 18.71 | 0.16 | 15.07 | 10.51 |
| | N | 3 | 3 | 3 | 3 | 3 | 3 | 3 |
| G2 | Mean | 8604.50 | 204.00 | 1.00 | 114.49 | 0.94 | 155.26 | 73.76 |
| 10 | S.D. | 1111.35 | 40.51 | 0.00 | 10.23 | 0.11 | 18.69 | 4.32 |
| | N | 3 | 3 | 3 | 3 | 3 | 3 | 3 |

G1: Ab417 (3 mg/kg), Ab417 (10 mg/kg)
S.D.: Standard deviation
N: Number of animals/Group As shown in Table 2, a group administered with the test material at a dose of 3 mg/kg showed $AUC_{last}$ (area under the blood concentration-time curve) of 3484.50±674.44 (μg·hr/mL), $C_{max}$ (maximum blood concentration) of 90.00±6.08 (μg/mL), $T_{max}$ (time to reach maximum blood concentration) of 1.00±0.00 (hr), $t_{1/2}$ (elimination half-life) of 65.05±18.71 (hr), $CL_t$ (systemic clearance) of 0.81±0.16 (mL/hr/kg), $V_d$ (volume of distribution) of 73.73±15.07 (mL/kg), and MRT (mean residence time) of 60.11±10.51 (hr).

Further, a group administered with the test material at a dose of 10 mg/kg showed $AUC_{last}$ of 8604.50±1111.35 (μg·hr/mL), $C_{max}$ of 204.00±40.51 (μg/mL), $T_{max}$ of 1.00±0.00 (hr), $t_{1/2}$ of 114.49±10.23 (hr), $CL_t$ of 0.94±0.11 (mL/hr/kg), $V_d$ of 155.26±18.69 (mL/kg) and MRT of 73.76±4.32 (hr).

Further, Ab417 antibody reached the maximum blood concentration at about 1.00 hr after administration, and the concentration of parent drug was reduced by about 10% of $C_{max}$ at 240 hours. All parameters except $T_{max}$ increased in a dose-dependent manner, and the time to reach maximum blood concentration did not depend on the dose. Further, as the dose was increased, half-life and residence time increased.

Furthermore, general signs were observed after administration until the last blood collection. As a result, no abnormal signs were observed in all animals, and no significant abnormalities that may influence the test result were observed at each step of administration and blood collection. The body weight was measured before administration on the day of administration, and no reduction in body weight was observed.

Example 8. Toxicity Test of Ab417 Antibody in Normal Mouse (Example 8-1) Binding of Ab417 Antibody to Normal Mouse Tissue and Analysis of L1CAM Expression Since Ab417 antibody has high affinity for mouse L1CAM ($K_D$, 0.1 nM) as well as for human L1CAM ($K_D$, 0.2 nM), it was thought that toxicity in a patient can be predicted by a toxicity test in a normal mouse. However, because the antibody is a human antibody, it causes immune responses in normal mice upon repeated administration, and thus single administration was performed in the toxicity test. The respective tissues of normal mice were prepared as frozen sections, and immunohistochemistry was performed to examine binding of Ab417 antibody in tissues, in which L1CAM is known to be expressed. The respective tissue frozen sections were treated with 2.5 μg/ml of Ab417 antibody, and human Ig Fc-specific antibody (Pierce) was treated at a concentration of 5 μg/ml as a secondary antibody to examine antibody binding by staining.

As shown in FIG. 10, binding of Ab417 antibody was observed in the central nerve cells such as cerebrum, cerebellum, and spinal cord, and peripheral nerve cells present in various organs and tissues including the digestive system.

Further, the binding was also observed in some tubular epithelial cells of the kidney, but no binding of Ab417 antibody was observed in other organs. These results suggest that L1CAM expression patterns in normal mouse tissues are similar to L1CAM expression patterns in the human tissues, and thus toxicity to patients can be predicted by the toxicity test in normal mice.

(Example 8-2) Toxicity and Safety Pharmacology Evaluation of Ab417 Antibody

Since it was confirmed that Ab417 antibody is widely distributed throughout the body when administered to normal mice, toxicity was examined while the antibody was administered by varying the concentration. To this end, each 6 of normal ICR female and male mice were subjected to single intravenous administration using Ab417 antibody at a concentration of 10, 30 or 50 mg/kg. Thereafter, signs of toxicity and neurological signs were examined in accordance with Irwin Test, and autopsy was performed 10 days after administration to perform histopathological examination of all organs including the nerve system and electron microscopy of the sciatic nerve. Irwin's test parameters are shown in Table 3 below.

TABLE 3

Irwin's test parameters

| No. | Parameter | Rating scale |
|---|---|---|
| 1 | Animal eats | 0, 1 |
| 2 | Animal drinks | 0, 1 |
| 3 | Animal sleeps | 0, 1 |
| 4 | Awake, no motor activity | 0, 1 |
| 5 | Moving around in cage | 0, 1 |
| 6 | Piloerection (in cage) | 0, 1 |
| 7 | Aggressiveness towards cage mate | 0, 1 |
| 8 | Vocalization (in cage) | 0, 1 |
| 9 | Grooming (in cage) | 0, 1 |
| 10 | Arousal | −3, −2, −1, 0, 1, 2, 3 |
| 11 | Finger approach | −2, −1, 0, 1, 2 |
| 12 | Head touch | −2, −1, 0 1, 2 |
| 13 | Fear | −2, −1, 0, 1, 2 |
| 14 | Body position | −3, −2, −1, 0, 1, 2, 3 |
| 15 | Spontaneous locomotor activity | −2, −1, 0, 1, 2 |
| 16 | Ataxic gait | 0, 1, 2, n.a. |
| 17 | Hypotonic gait | 0, 1, 2, n.a. |
| 18 | Twitches | 0, 1, 2, 3, 4 |
| 19 | Seizures | 0, 1, 2, 3, 4 |
| 20 | Writhing symptom | 0, 1, 2, 3, 4 |
| 21 | Bizarre behaviour | 0, 1, 2, 3, 4 |
| 22 | Tail position | 0, 1, 2, 3, 4 |
| 23 | Piloerection | 0, 1, 2 |
| 24 | Grooming | 0, 1, 2 |
| 25 | Rearing | −1, −2, 0, 1, 2 |
| 26 | Urination | −1, −2, 0, 1, 2 |
| 27 | Defecation | −1, −2, 0, 1, 2 |
| 28 | Respiration | −3, −2, −1, 0, 1 |
| 29 | Tremors | 0, 1, 2, 3, 4 |
| 30 | Startle response | −1, −2, 0, 1, 2 |
| 31 | Positional passivity | −2, −1, 0, 1, 2, 3 |
| 32 | Catalepsy | 0, 1, 2, 3, 4 |
| 33 | Visual placing | −3, −2, −1, 0, 1 |
| 34 | Grip strength | −2, −1, 0, 1, 2 |
| 35 | Corneal reflex | −2, −1, 0, 1, 2 |
| 36 | Pinna reflex | −2, −1, 0, 1, 2 |
| 37 | Body tone | −2, −1, 0, 1, 2 |
| 38 | Abdominal tone | −2, −1, 0, 1, 2 |
| 39 | Hindlimb tone | −3, −2, −1, 0, 1, 2 |
| 40 | Hindlimb (plantar) reflex | −2, −1, 0, 1, 2 |
| 41 | Skin color | −2, −1, 0, 1, 2 |
| 42 | Cyanosis | 0, 1, 2 |
| 43 | Eyes opening | 0, 1, 2 |
| 44 | Exophthalmos | 0, 1, 2 |
| 45 | Pupil diameter | −1, 0, 1, 2 |
| 46 | Lacrimation | −2, −1, 0, 1, 2 |
| 47 | Chromodacryorrhea | 0, 1, 2, 3, 4 |
| 48 | Salivation | −1, 0, 1, 2 |
| 49 | Sensitivity to pinching of tail | −2, −1, 0, 1, 2 |
| 50 | Righting reflex | 0, 1, 2, 3, 4 |
| 51 | Aggressiveness | 0, 1, 2 |
| 52 | Abnormal vocalization | 0, 1, 2 |
| 53 | Consistency of feces | −2, −1, 0, 1, n.a. |
| 54 | Urine color | 0, 1, 2, n.a. |
| 55 | Death | 0, 1 |

Clinical symptoms of animals were examined every day after administration of the test material, and no abnormal behaviors were observed. During the test period, there were no significant changes in body weight, feeding and drinking between the groups.

Further, female and male mice were subjected to autopsy 10 days after administration of Ab417 antibody. During the autopsy, the organs were weighed and visual inspection was performed. As a result, no significant changes were observed in the administration groups, compared to the control group.

Further, no findings which were thought to be attributed to administration of Ab417 antibody were observed in histological examination of the organs. No nerve fiber degeneration was observed in the sciatic nerve. Each 1 of female and male mice was subjected to electron microscopy of the sciatic nerve, and as a result, there were no morphological changes in diameter of myelin sheath and axon. The blood test result also showed a red blood cell count within a normal range.

As a result of single administration of ICR mice with Ab417 antibody at a dose of 10, 30, or 50 mg/kg, no neuronal toxicity was caused by the Ab417 antibody administered.

Example 9. Analysis of Anti-Cancer Efficacy of Ab417 Antibody Against Extrahepatic Bile Duct Cancer To examine anti-cancer efficacy of Ab417 antibody against extrahepatic bile duct cancer, human-derived extrahepatic bile duct cancer cell line TFK-1 was used. First, male NOD/SCID mice were transplanted with the extrahepatic bile duct cancer cell line TFK-1. When mean tumor volume reached 130 mm$^3$, Ab417 antibody or control hFc (human Fc) was intravenously administered twice/week for 4 weeks total 8 times to evaluate inhibitory effects on tumor growth. During observation period, general signs were observed once a day, and the body weight of the animal and the tumor volume were measured twice a week. After termination of the observation, tumors were excised and weighed.

As a result, when Ab417 antibody of 10 mg/kg was administered, the volume (FIG. 11a) and weight (FIG. 11b) of the tumor were very small, compared to hFc administration. It can be seen that tumor growth was remarkably inhibited and the tumor weight was very low in the group administered with Ab417 antibody of 10 mg/kg, compared to the negative control group. Further, the group administered with Ab417 antibody of 10 mg/kg showed IR (tumor growth inhibition rate) of 64.7%. Furthermore, general signs and body weight were examined (FIG. 13c), and as a result, no abnormal findings and deaths due to administration were observed in all administration groups.

These results suggest that Ab417 antibody remarkably inhibits growth of extrahepatic bile duct cancer, thereby showing very excellent anti-cancer effect on extrahepatic bile duct cancer.

Further, these results suggest that the antibody of the present invention having high binding affinity for L1CAM can be used very effectively for the prevention and treatment of cancer.

Example 10. Characterization of Ab417-H6L2 and Ab417-H6L6 Mutants (Example 10-1) Isoelectric Point (pI) Analysis of Ab417, Ab417-H6L2 Mutant, and Ab417-H6L6 Mutant The CE Plus 800 (Beckman Coulter) system was used to perform cIEF of Ab417 and mutants thereof. pI values of respective materials were determined using 32 Karat program.

As a result, it was found that pI value of Ab417 antibody was 9.59, pI value of H6L2 mutant was 9.22, and pI value of H6L6 mutant was 8.83 (FIGS. 12a, 12b, and 12c).

(Example 10-2) Analysis of Affinity of Ab417, Ab417-H6L2 Mutant, and Ab417-H6L6 Mutant for Human and Mouse L1CAM Affinities of Ab417, Ab417-H6L2 mutant, and Ab417-H6L6 mutant for human and mouse L1CAM were examined using Octet RED (fortebio). For affinity analysis, the antibodies were diluted with a PBA solution prepared by adding 0.1% BSA to PBS at a concentration of 2 µg/ml. Human L1CAM was serially diluted with PBA at a concentration of 100, 50, 25, 12.5, 6.25, 0 nM, and mouse L1CAM was serially diluted with PBA at a concentration of 30, 10, 3.3, 1.1, 0.37, 0 nM. Each 200 it thereof was added to opaque 96-well plate to prevent light transmission. AHC (anti-human IgG Fc capture) sensor chip was used to analyze binding kinetics of the antibodies to antigens by examining changes in refractive index which occurs upon association and dissociation of antibody and antigen while transferring the sensor chip to PBS solution, antibody, PBS solution, antigen, and PBS solution in this order.

As a result, affinity ($K_D$) of Ab417, Ab417-H6L2 mutant, and Ab417-H6L6 mutant for human L1CAM was about 0.2 nM. Despite amino acid substitution, there were no changes in the affinities of these antibodies (Table 4), and there were also no changes in the affinities of these antibodies for mouse L1CAM (Table 5).

TABLE 4

Analysis of affinity for human L1CAM

| Antibody | $K_D$ (M) | Kon (1/Ms) | Kdis (1/s) | Full $R^2$ |
|---|---|---|---|---|
| Ab417 | 2.39E−10 | 1.89E+05 | 4.51E−05 | 0.974016 |
| Ab417-H6L2 | 2.20E−10 | 1.46E+05 | 3.22E−05 | 0.979832 |
| Ab417-H6L6 | 2.46E−10 | 1.48E+05 | 3.64E−05 | 0.989637 |

TABLE 5

Analysis of affinity for mouse L1CAM

| Antibody | $K_D$ (M) | Kon (1/Ms) | Kdis (1/s) | Full $R^2$ |
|---|---|---|---|---|
| Ab417 | 1.08E−10 | 2.44E+05 | 2.64E−05 | 0.995464 |
| Ab417-H6L2 | 1.31E−10 | 2.04E+05 | 2.67E−05 | 0.996635 |
| Ab417-H6L6 | 9.84E−11 | 2.14E+05 | 2.11E−05 | 0.996065 |

(Example 10-3) Comparison of Anti-Cancer Efficacy Between Ab417 and Ab417-H6L2 Mutant Ab417-H6L2 mutant which shows higher productivity than Ab417 antibody and maintains affinity for L1CAM was selected and its anti-cancer efficacy was compared to that of Ab417 antibody. First, to produce Ab417 and Ab417-H6L2 mutant, Expi293™ Expression System (Gibco) was used. When Expi293F cells showed growth rate of 95% or more, cells were suspended in 25.5 ml of Expi293™ Expression Media at a density of $3 \times 10^6$ cell/ml, and put in a 125 ml-Erlenmeyer flask, followed by suspension culture at 37° C., 8% $CO_2$, and 125 rpm. Next day, 30 µg of plasmid DNA in Opti-MEM® I medium was mixed with 80 it of Expi-Fectamine™ 293 Reagent, and the mixture was added to the cells under suspension culture for transfection. 16 hours later, 150 µl of ExpiFectamine™ 293 Transfection Enhancer 1 and 1.5 ml of ExpiFectamine™ 293 Transfection Enhancer 2 were added thereto, followed by suspension culture for 3 days. 3 days later, the culture broth was centrifuged at 3500 rpm for 20 minutes (twice) and purified under the same conditions as Ab417. Male Balb/c nude mice were transplanted with human-derived intrahepatic bile duct cancer cell line Choi-CK. When the mean tumor volume reached 100 $mm^3$, each 10 mg/kg of the produced Ab417 and Ab417-H6L2 mutant was injected to the caudal vein of mouse twice/week for 3 weeks total 6 times. In this regard, 3.3 mg/kg of human Fc control antibody which is an isotype control of the antibody was injected as a negative control of the antibody at the same frequency. After administration, general signs were observed once a day, and the body weight and tumor volume of the animal were measured twice a week. After termination of the observation, tumors were excised and weighed. The body weight of the animal and the tumor volume and weight thus measured were analyzed using SAS program.

As a result, administration of Ab417 antibody and Ab417-H6L2 antibody showed similar tumor volume growth, which was much lower than administration of human Fc antibody (FIG. 13a). Further, administration of Ab417 antibody and Ab417-H6L2 antibody showed similar tumor weight, which was much lower than administration of human Fc antibody (FIG. 13b). Furthermore, administration of Ab417 antibody and Ab417-H6L2 antibody showed similar body weight of Choi-CK xenograft model, which was much lower than administration of human Fc antibody (FIG. 13c).

These results indicate that there is no difference in anti-cancer efficacy between Ab417 antibody and Ab417-H6L2 antibody.

Based on the above description, it will be understood by those skilled in the art that the present invention may be implemented in a different specific form without changing the technical spirit or essential characteristics thereof.

Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

EFFECT OF THE INVENTION

The antibody of the present invention binds to both human and mouse L1CAM proteins with high affinity, and thus it may be effectively used in the fields requiring the antibody, for example, diagnosis and treatment of diseases associated with L1CAM overexpression, such as cancer.

What is claimed is:

1. An antibody binding to human L1 cell adhesion molecule (L1CAM) protein, comprising:
a heavy-chain variable region comprising (i) a heavy chain CDR1 of SEQ ID NO. 2; (ii) a heavy chain CDR2 of SEQ ID NO. 9 or a heavy chain CDR2 of SEQ ID NO. 9 except for a substitution of glutamic acid for aspartic acid as an amino acid at position 5; and (iii) a heavy chain CDR3 of SEQ ID NO. 10; and
a light-chain variable region comprising (iv) a light chain CDR1 of SEQ ID NO. 6 or a light chain CDR1 of SEQ ID NO. 6 except for a substitution of serine for isoleucine as an amino acid at position 8; (v) a light chain CDR2 of SEQ ID NO. 7; and (vi) a light chain CDR3 of SEQ ID NO. 11 or a light chain CDR3 of SEQ ID NO. 15.

2. The antibody of claim 1, wherein the antibody comprises a heavy-chain variable region comprising a heavy chain CDR1 of SEQ ID NO. 2, a heavy chain CDR2 of SEQ ID NO. 9, and a heavy chain CDR3 of SEQ ID NO. 10; and
a light-chain variable region comprising a light chain CDR1 of SEQ ID NO. 6, a light chain CDR2 of SEQ ID NO. 7, and a light chain CDR3 of SEQ ID NO. 11.

3. The antibody of claim 2, wherein the antibody comprises a heavy-chain variable region of SEQ ID NO. 12 and a light-chain variable region of SEQ ID NO. 13.

4. The antibody of claim 1, wherein the antibody comprises a heavy-chain variable region comprising a heavy chain CDR1 of SEQ ID NO. 2, a heavy chain CDR2 of SEQ ID NO. 9, and a heavy chain CDR3 of SEQ ID NO. 10; and
a light-chain variable region comprising a light chain CDR1 of SEQ ID NO. 6, a light chain CDR2 of SEQ ID NO. 7, and a light chain CDR3 of SEQ ID NO. 15.

5. The antibody of claim 4, wherein the antibody comprises a heavy-chain variable region of SEQ ID NO. 12 and a light-chain variable region of SEQ ID NO. 14.

6. The antibody of claim 1, wherein the antibody comprises a heavy-chain variable region comprising a heavy chain CDR1 of SEQ ID NO. 2, a heavy chain CDR2 of SEQ ID NO. 16, and a heavy chain CDR3 of SEQ ID NO. 10; and
a light-chain variable region comprising a light chain CDR1 of SEQ ID NO. 17, a light chain CDR2 of SEQ ID NO. 7, and a light chain CDR3 of SEQ ID NO. 15.

7. The antibody of claim 6, wherein the antibody comprises a heavy-chain variable region of SEQ ID NO. 18 and a light-chain variable region of SEQ ID NO. 19.

8. The antibody of claim 6, wherein the antibody comprises a heavy-chain variable region of SEQ ID NO. 18 and a light-chain variable region of SEQ ID NO. 34.

9. The antibody of claim 1, wherein the antibody comprises a heavy-chain variable region of SEQ ID NO. 12 or 18, and a light-chain variable region of SEQ ID NO. 14, 19, or 34.

10. The antibody of claim 1, wherein the heavy-chain variable region of the antibody comprises (i) a heavy chain framework region 1 (FR1) of SEQ ID NO. 22 or a heavy chain FR1 of SEQ ID NO. 22 except for a substitution of glycine for arginine as an amino acid at position 16; (ii) FR2 of SEQ ID NO. 23; (iii) a heavy chain FR3 of SEQ ID NO. 24 or a heavy chain FR3 of SEQ ID NO. 24 except for a substitution of alanine for lysine as an amino acid at position 10 and a substitution of alanine for proline as an amino acid at position 22; and (iv) FR4 of SEQ ID NO. 25, and the light-chain variable region thereof comprises (v) FR1 of SEQ ID NO. 28; (vi) a light chain FR2 of SEQ ID NO. 29 or a light chain FR2 of SEQ ID NO. 29 except for a substitution of glutamine for arginine as an amino acid at position 3, a substitution of lysine for arginine as an amino acid at position 5, and a substitution of glutamine for lysine as an amino acid at position 8; (vii) a light chain FR3 of SEQ ID NO. 30 or SEQ ID NO. 33, or a light chain FR3 of SEQ ID NO. 30 except for a substitution of isoleucine for valine as an amino acid at position 19 and a substitution of alanine for glycine as an amino acid at position 28; and (viii) a light chain FR4 of SEQ ID NO. 31.

11. An antibody binding to human L1 cell adhesion molecule (L1CAM) protein, comprising:

a heavy-chain variable region comprising (i) a heavy chain CDR1 of SEQ ID NO. 2; (ii) a heavy chain CDR2 selected from the group consisting of a heavy chain CDR2 of SEQ ID NO. 3, a heavy chain CDR2 of SEQ ID NO. 3 except for a substitution of phenylalanine for valine as an amino acid at position 1, and a heavy chain CDR2 of SEQ ID NO. 3 except for a substitution of phenylalanine for valine as an amino acid at position 1 and a substitution of glutamic acid for aspartic acid at position 5; and (iii) a heavy chain CDR3 of SEQ ID NO. 4 or a heavy chain CDR3 of SEQ ID NO. 4 except for a substitution of alanine for histidine as an amino acid at position 3; and a light-chain variable region comprising (iv) a light chain CDR1 of SEQ ID NO. 6 or a light chain CDR1 of SEQ ID NO. 6 except for a substitution of serine for isoleucine as an amino acid at position 8; (v) a light chain CDR2 of SEQ ID NO. 7; and (vi) a light chain CDR3 selected from the group consisting of a light chain CDR3 of SEQ ID NO. 8, a light chain CDR3 of SEQ ID NO. 8 except for a substitution of alanine for aspartic acid as an amino acid at position 5, and a light chain CDR3 of SEQ ID NO. 15.

12. A polynucleotide encoding the antibody of claim 1.

13. An expression vector comprising the polynucleotide of claim 12.

14. A transformant comprising the expression vector of claim 13.

15. A composition comprising the antibody of claim 1.

16. The composition of claim 15, wherein the composition is used for diagnosing cancer.

17. A method for diagnosing an L1CAM-expressing cancer, the method comprising: contacting a biological sample separated from an individual suspected of having an L1CAM-expressing cancer with the antibody of claim 1; and detecting formation of an antigen-antibody complex.

18. A kit for diagnosing cancer, comprising the composition of claim 15.

19. An antibody-drug conjugate, wherein the drug is conjugated to the antibody of claim 1.

20. A method for treating an L1CAM-expressing cancer, the method comprising administering the antibody of claim 1 to a subject in need thereof.

* * * * *

SEQUENCE LISTING

```
<160> NUMBER OF SEQ ID NOS: 34

<210> SEQ ID NO 1
<211> LENGTH: 121
<212> TYPE: PRT
<213> ORGANISM: Artificial Sequence
<220> FEATURE:
<223> OTHER INFORMATION: a heavy chain variable region of Ab4

<400> SEQUENCE: 1

Glu Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Arg Phe
                 20                  25                  30

Gly Met His Trp Val Arg Gln Ala Pro Gly Lys Gly Leu Glu Trp Val
             35                  40                  45

Ala Val Ile Ser Asn Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Arg Gly Arg His Tyr Gly Ser Gly Ser Leu Phe Asp Pro Trp Gly
            100                 105                 110

Gln Gly Thr Leu Val Thr Val Ser Ser
        115                 120

<210> SEQ ID NO 2
<211> LENGTH: 5
<212> TYPE: PRT
<213> ORGANISM: Artificial Sequence
<220> FEATURE:
<223> OTHER INFORMATION: CDR1 of a heavy chain variable region of Ab4

<400> SEQUENCE: 2

Arg Phe Gly Met His
  1               5

<210> SEQ ID NO 3
<211> LENGTH: 17
<212> TYPE: PRT
<213> ORGANISM: Artificial Sequence
<220> FEATURE:
<223> OTHER INFORMATION: CDR2 of a heavy chain variable region of Ab4

<400> SEQUENCE: 3

Val Ile Ser Asn Asp Gly Ser Asn Lys Tyr Tyr Ala Asp Ser Val Lys
  1               5                  10                  15

Gly

<210> SEQ ID NO 4
<211> LENGTH: 12
<212> TYPE: PRT
<213> ORGANISM: Artificial Sequence
```

```
<220> FEATURE:
<223> OTHER INFORMATION: CDR3 of a heavy chain variable region of Ab4

<400> SEQUENCE: 4

Gly Arg His Tyr Gly Ser Gly Ser Leu Phe Asp Pro
 1               5                  10

<210> SEQ ID NO 5
<211> LENGTH: 108
<212> TYPE: PRT
<213> ORGANISM: Artificial Sequence
<220> FEATURE:
<223> OTHER INFORMATION: a light chain variable region of Ab4

<400> SEQUENCE: 5

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Arg Thr Ile Ser Ile Tyr
                20                  25                  30

Val Asn Trp Tyr Arg Gln Arg Pro Gly Lys Ala Pro Glu Ser Leu Ile
            35                  40                  45

Tyr Ala Ala Ser Asn Leu His Ser Gly Val Pro Ser Arg Phe Ser Gly
        50                  55                  60

Ser Gly Ser Gly Thr Asp Phe Thr Leu Thr Val Ser Ser Leu Gln Pro
 65                 70                  75                  80

Glu Asp Phe Gly Thr Tyr Tyr Cys Gln Gln Thr His Asp Thr Arg Gln
                85                  90                  95

Tyr Thr Phe Gly Gln Gly Thr Lys Leu Glu Ile Lys
            100                 105

<210> SEQ ID NO 6
<211> LENGTH: 11
<212> TYPE: PRT
<213> ORGANISM: Artificial Sequence
<220> FEATURE:
<223> OTHER INFORMATION: CDR1 of a light chain variable region of Ab4

<400> SEQUENCE: 6

Arg Ala Ser Arg Thr Ile Ser Ile Tyr Val Asn
 1               5                  10

<210> SEQ ID NO 7
<211> LENGTH: 7
<212> TYPE: PRT
<213> ORGANISM: Artificial Sequence
<220> FEATURE:
<223> OTHER INFORMATION: CDR2 of a light chain variable region of Ab4

<400> SEQUENCE: 7

Ala Ala Ser Asn Leu His Ser
 1               5

<210> SEQ ID NO 8
<211> LENGTH: 10
<212> TYPE: PRT
<213> ORGANISM: Artificial Sequence
<220> FEATURE:
<223> OTHER INFORMATION: CDR3 of a light chain variable region of Ab4

<400> SEQUENCE: 8

Gln Gln Thr His Asp Thr Arg Gln Tyr Thr
 1               5                  10
```

```
<210> SEQ ID NO 9
<211> LENGTH: 17
<212> TYPE: PRT
<213> ORGANISM: Artificial Sequence
<220> FEATURE:
<223> OTHER INFORMATION: CDR2 of a heavy chain variable region of V50F

<400> SEQUENCE: 9

Phe Ile Ser Asn Asp Gly Ser Asn Lys Tyr Tyr Ala Asp Ser Val Lys
 1               5                  10                  15
Gly

<210> SEQ ID NO 10
<211> LENGTH: 12
<212> TYPE: PRT
<213> ORGANISM: Artificial Sequence
<220> FEATURE:
<223> OTHER INFORMATION: CDR3 of a heavy chain variable region of H97A

<400> SEQUENCE: 10

Gly Arg Ala Tyr Gly Ser Gly Ser Leu Phe Asp Pro
 1               5                  10

<210> SEQ ID NO 11
<211> LENGTH: 10
<212> TYPE: PRT
<213> ORGANISM: Artificial Sequence
<220> FEATURE:
<223> OTHER INFORMATION: CDR3 of a light chain variable region of D93A

<400> SEQUENCE: 11

Gln Gln Thr His Ala Thr Arg Gln Tyr Thr
 1               5                  10

<210> SEQ ID NO 12
<211> LENGTH: 121
<212> TYPE: PRT
<213> ORGANISM: Artificial Sequence
<220> FEATURE:
<223> OTHER INFORMATION: a heavy chain variable region of Ab4M and Ab417

<400> SEQUENCE: 12

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Arg Phe
                20                  25                  30

Gly Met His Trp Val Arg Gln Ala Pro Gly Lys Gly Leu Glu Trp Val
            35                  40                  45

Ala Phe Ile Ser Asn Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                85                  90                  95

Ala Arg Gly Arg Ala Tyr Gly Ser Gly Ser Leu Phe Asp Pro Trp Gly
            100                 105                 110

Gln Gly Thr Leu Val Thr Val Ser Ser
        115                 120

<210> SEQ ID NO 13
<211> LENGTH: 108
<212> TYPE: PRT
<213> ORGANISM: Artificial Sequence
```

-continued

```
<220> FEATURE:
<223> OTHER INFORMATION: a light chain variable region of Ab4M

<400> SEQUENCE: 13

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Arg Thr Ile Ser Ile Tyr
            20                  25                  30

Val Asn Trp Tyr Arg Gln Arg Pro Gly Lys Ala Pro Glu Ser Leu Ile
        35                  40                  45

Tyr Ala Ala Ser Asn Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr His Ala Thr Arg Gln
                85                  90                  95

Tyr Thr Phe Gly Gln Gly Thr Lys Leu Glu Ile Lys
            100                 105

<210> SEQ ID NO 14
<211> LENGTH: 108
<212> TYPE: PRT
<213> ORGANISM: Artificial Sequence
<220> FEATURE:
<223> OTHER INFORMATION: a light chain variable region of Ab417

<400> SEQUENCE: 14

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Arg Thr Ile Ser Ile Tyr
            20                  25                  30

Val Asn Trp Tyr Arg Gln Arg Pro Gly Lys Ala Pro Glu Ser Leu Ile
        35                  40                  45

Tyr Ala Ala Ser Asn Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Gly Arg Gly Val
                85                  90                  95

Val Thr Phe Gly Gln Gly Thr Lys Leu Glu Ile Lys
            100                 105

<210> SEQ ID NO 15
<211> LENGTH: 10
<212> TYPE: PRT
<213> ORGANISM: Artificial Sequence
<220> FEATURE:
<223> OTHER INFORMATION: LCDR3 of Ab417

<400> SEQUENCE: 15

Gln Gln Ser Ile Gly Arg Gly Val Val Thr
 1               5                  10

<210> SEQ ID NO 16
<211> LENGTH: 17
<212> TYPE: PRT
<213> ORGANISM: Artificial Sequence
<220> FEATURE:
<223> OTHER INFORMATION: HCDR2 (H6)

<400> SEQUENCE: 16
```

Phe Ile Ser Asn Glu Gly Ser Asn Lys Tyr Tyr Ala Asp Ser Val Lys
1               5                   10                  15

Gly

<210> SEQ ID NO 17
<211> LENGTH: 11
<212> TYPE: PRT
<213> ORGANISM: Artificial Sequence
<220> FEATURE:
<223> OTHER INFORMATION: LCDR1 (L2)

<400> SEQUENCE: 17

Arg Ala Ser Arg Thr Ile Ser Ser Tyr Val Asn
1               5                   10

<210> SEQ ID NO 18
<211> LENGTH: 121
<212> TYPE: PRT
<213> ORGANISM: Artificial Sequence
<220> FEATURE:
<223> OTHER INFORMATION: Heavy chain variable region (H6)

<400> SEQUENCE: 18

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Arg Phe
            20                  25                  30

Gly Met His Trp Val Arg Gln Ala Pro Gly Lys Gly Leu Glu Trp Val
        35                  40                  45

Ala Phe Ile Ser Asn Glu Gly Ser Asn Lys Tyr Tyr Ala Asp Ser Val
    50                  55                  60

Lys Gly Arg Phe Thr Ile Ser Arg Asp Asn Ser Ala Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ala Tyr Gly Ser Gly Ser Leu Phe Asp Pro Trp Gly
            100                 105                 110

Gln Gly Thr Leu Val Thr Val Ser Ser
        115                 120

<210> SEQ ID NO 19
<211> LENGTH: 108
<212> TYPE: PRT
<213> ORGANISM: Artificial Sequence
<220> FEATURE:
<223> OTHER INFORMATION: Light chain variable region (L2)

<400> SEQUENCE: 19

Asp Ile Gln Leu Thr Gln Ser Pro Ser Ser Leu Ser Ala Ser Val Gly
1               5                   10                  15

Asp Arg Val Thr Ile Thr Cys Arg Ala Ser Arg Thr Ile Ser Ser Tyr
            20                  25                  30

Val Asn Trp Tyr Arg Gln Arg Pro Gly Lys Ala Pro Glu Ser Leu Ile
        35                  40                  45

Tyr Ala Ala Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Gly Arg Gly Val

```
                        85                   90                    95
Val Thr Phe Gly Gln Gly Thr Lys Leu Glu Ile Lys
                100                 105

<210> SEQ ID NO 20
<211> LENGTH: 121
<212> TYPE: PRT
<213> ORGANISM: Artificial Sequence
<220> FEATURE:
<223> OTHER INFORMATION: Heavy chain variable region (H5)

<400> SEQUENCE: 20

Glu Val Gln Leu Val Glu Ser Gly Gly Val Val Gln Pro Gly Gly
  1               5                  10                  15

Ser Leu Arg Leu Ser Cys Ala Ala Ser Gly Phe Thr Phe Ser Arg Phe
             20                  25                  30

Gly Met His Trp Val Arg Gln Ala Pro Gly Lys Gly Leu Glu Trp Val
         35                  40                  45

Ala Phe Ile Ser Asn Asp Gly Ser Asn Lys Tyr Tyr Ala Asp Ser Val
     50                  55                  60

Lys Gly Arg Phe Thr Ile Ser Arg Asp Asn Ser Ala Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Arg Ala Tyr Gly Ser Gly Ser Leu Phe Asp Pro Trp Gly
            100                 105                 110

Gln Gly Thr Leu Val Thr Val Ser Ser
        115                 120

<210> SEQ ID NO 21
<211> LENGTH: 108
<212> TYPE: PRT
<213> ORGANISM: Artificial Sequence
<220> FEATURE:
<223> OTHER INFORMATION: Light chain variable region (L1)

<400> SEQUENCE: 21

Asp Ile Gln Leu Thr Gln Ser Pro Ser Ser Leu Ser Ala Ser Val Gly
  1               5                  10                  15

Asp Arg Val Thr Ile Thr Cys Arg Ala Ser Arg Thr Ile Ser Ile Tyr
             20                  25                  30

Val Asn Trp Tyr Gln Gln Lys Pro Gly Gln Ala Pro Glu Ser Leu Ile
         35                  40                  45

Tyr Ala Ala Ser Asn Leu His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Ile Gly Arg Gly Val
                 85                  90                  95

Val Thr Phe Gly Gln Gly Thr Lys Leu Glu Ile Lys
            100                 105

<210> SEQ ID NO 22
<211> LENGTH: 30
<212> TYPE: PRT
<213> ORGANISM: Artificial Sequence
<220> FEATURE:
<223> OTHER INFORMATION: HFR1

<400> SEQUENCE: 22
```

```
Glu Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser
             20                  25                  30

<210> SEQ ID NO 23
<211> LENGTH: 14
<212> TYPE: PRT
<213> ORGANISM: Artificial Sequence
<220> FEATURE:
<223> OTHER INFORMATION: HFR2

<400> SEQUENCE: 23

Trp Val Arg Gln Ala Pro Gly Lys Gly Leu Glu Trp Val Ala
  1               5                  10

<210> SEQ ID NO 24
<211> LENGTH: 32
<212> TYPE: PRT
<213> ORGANISM: Artificial Sequence
<220> FEATURE:
<223> OTHER INFORMATION: HFR3

<400> SEQUENCE: 24

Arg Phe Thr Ile Ser Arg Asp Asn Ser Lys Asn Thr Leu Tyr Leu Gln
  1               5                  10                  15

Met Asn Ser Leu Arg Pro Glu Asp Thr Ala Val Tyr Tyr Cys Ala Arg
             20                  25                  30

<210> SEQ ID NO 25
<211> LENGTH: 11
<212> TYPE: PRT
<213> ORGANISM: Artificial Sequence
<220> FEATURE:
<223> OTHER INFORMATION: HFR4

<400> SEQUENCE: 25

Trp Gly Gln Gly Thr Leu Val Thr Val Ser Ser
  1               5                  10

<210> SEQ ID NO 26
<211> LENGTH: 30
<212> TYPE: PRT
<213> ORGANISM: Artificial Sequence
<220> FEATURE:
<223> OTHER INFORMATION: HFR1 (H6)

<400> SEQUENCE: 26

Glu Val Gln Leu Val Glu Ser Gly Gly Gly Val Val Gln Pro Gly Gly
  1               5                  10                  15

Ser Leu Arg Leu Ser Cys Ala Ala Ser Gly Phe Thr Phe Ser
             20                  25                  30

<210> SEQ ID NO 27
<211> LENGTH: 32
<212> TYPE: PRT
<213> ORGANISM: Artificial Sequence
<220> FEATURE:
<223> OTHER INFORMATION: HFR3 (H6)

<400> SEQUENCE: 27

Arg Phe Thr Ile Ser Arg Asp Asn Ser Ala Asn Thr Leu Tyr Leu Gln
  1               5                  10                  15

Met Asn Ser Leu Arg Ala Glu Asp Thr Ala Val Tyr Tyr Cys Ala Arg
```

```
                    20                  25                  30

<210> SEQ ID NO 28
<211> LENGTH: 23
<212> TYPE: PRT
<213> ORGANISM: Artificial Sequence
<220> FEATURE:
<223> OTHER INFORMATION: LFR1

<400> SEQUENCE: 28

Asp Ile Gln Leu Thr Gln Ser Pro Ser Ser Leu Ser Ala Ser Val Gly
  1               5                  10                  15

Asp Arg Val Thr Ile Thr Cys
            20

<210> SEQ ID NO 29
<211> LENGTH: 15
<212> TYPE: PRT
<213> ORGANISM: Artificial Sequence
<220> FEATURE:
<223> OTHER INFORMATION: LFR2

<400> SEQUENCE: 29

Trp Tyr Arg Gln Arg Pro Gly Lys Ala Pro Glu Ser Leu Ile Tyr
  1               5                  10                  15

<210> SEQ ID NO 30
<211> LENGTH: 32
<212> TYPE: PRT
<213> ORGANISM: Artificial Sequence
<220> FEATURE:
<223> OTHER INFORMATION: LFR3

<400> SEQUENCE: 30

Gly Val Pro Ser Arg Phe Ser Gly Ser Gly Ser Gly Thr Asp Phe Thr
  1               5                  10                  15

Leu Thr Val Ser Ser Leu Gln Pro Glu Asp Phe Gly Thr Tyr Tyr Cys
                20                  25                  30

<210> SEQ ID NO 31
<211> LENGTH: 10
<212> TYPE: PRT
<213> ORGANISM: Artificial Sequence
<220> FEATURE:
<223> OTHER INFORMATION: LFR4

<400> SEQUENCE: 31

Phe Gly Gln Gly Thr Lys Leu Glu Ile Lys
  1               5                  10

<210> SEQ ID NO 32
<211> LENGTH: 15
<212> TYPE: PRT
<213> ORGANISM: Artificial Sequence
<220> FEATURE:
<223> OTHER INFORMATION: LFR2 (L1, L6)

<400> SEQUENCE: 32

Trp Tyr Gln Gln Lys Pro Gly Gln Ala Pro Glu Ser Leu Ile Tyr
  1               5                  10                  15

<210> SEQ ID NO 33
<211> LENGTH: 32
<212> TYPE: PRT
<213> ORGANISM: Artificial Sequence
<220> FEATURE:
```

```
<223> OTHER INFORMATION: LFR3 (Ab4M)

<400> SEQUENCE: 33

Gly Val Pro Ser Arg Phe Ser Gly Ser Gly Ser Gly Thr Asp Phe Thr
 1               5                  10                  15

Leu Thr Ile Ser Ser Leu Gln Pro Glu Asp Phe Ala Thr Tyr Tyr Cys
                20                  25                  30

<210> SEQ ID NO 34
<211> LENGTH: 108
<212> TYPE: PRT
<213> ORGANISM: Artificial Sequence
<220> FEATURE:
<223> OTHER INFORMATION: Light chain variable region L6

<400> SEQUENCE: 34

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Arg Thr Ile Ser Ser Tyr
                20                  25                  30

Val Asn Trp Tyr Gln Gln Lys Pro Gly Gln Ala Pro Glu Ser Leu Ile
            35                  40                  45

Tyr Ala Ala Ser Asn Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Gly Arg Gly Val
                85                  90                  95

Val Thr Phe Gly Gln Gly Thr Lys Leu Glu Ile Lys
                100                 105
```